US012673095B2

(12) United States Patent
Aurisicchio et al.

(10) Patent No.: US 12,673,095 B2
(45) Date of Patent: Jul. 7, 2026

(54) POLYNUCLEOTIDES ENCODING SARS-COV-2 ANTIGENS AND USE THEREOF IN THE MEDICAL FIELD AS VACCINES

(71) Applicant: TAKIS S.R.L., Rome (IT)

(72) Inventors: Luigi Aurisicchio, Rome (IT); Emanuele Marra, Rome (IT); Giuseppe Roscilli, Rome (IT); Fabio Palombo, Rome (IT); Mariano Maffei, Rome (IT); Alessia Muzi, Rome (IT)

(73) Assignee: TAKIS S.R.L., Rome (IT)

( * ) Notice: Subject to any disclaimer, the term of this patent is extended or adjusted under 35 U.S.C. 154(b) by 817 days.

(21) Appl. No.: 17/997,527

(22) PCT Filed: Apr. 30, 2021

(86) PCT No.: PCT/IT2021/050130

§ 371 (c)(1),
(2) Date: Oct. 28, 2022

(87) PCT Pub. No.: WO2021/220319

PCT Pub. Date: Nov. 4, 2021

(65) Prior Publication Data

US 2023/0285540 A1 Sep. 14, 2023

(30) Foreign Application Priority Data

Apr. 30, 2020 (IT) ........................ 102020000009625

(51) Int. Cl.
*A61K 39/215* (2006.01)
*A61P 31/14* (2006.01)
*A61K 39/00* (2006.01)

(52) U.S. Cl.
CPC ............ *A61K 39/215* (2013.01); *A61P 31/14* (2018.01); *A61K 2039/53* (2013.01); *A61K 2039/552* (2013.01)

(58) Field of Classification Search
None
See application file for complete search history.

(56) References Cited

U.S. PATENT DOCUMENTS

2009/0104226 A1* 4/2009 Perri ....................... A61P 11/00
424/202.1
2023/0285540 A1* 9/2023 Aurisicchio ......... C07K 14/005

FOREIGN PATENT DOCUMENTS

CN 110951756 A 4/2020
CN 110974950 A 4/2020
CN 112592928 A 4/2021
EP 3809137 A1 4/2021
(Continued)

OTHER PUBLICATIONS

WIPO machine translation of Liang et al. (CN 110951756) published Apr. 3, 2020.*
(Continued)

*Primary Examiner* — Shanon A. Foley
(74) *Attorney, Agent, or Firm* — KNOBBE, MARTENS, OLSON & BEAR, LLP

(57) ABSTRACT

The present invention relates to polynucleotides encoding antigens of the SARS-CoV-2 coronavirus spike protein and use thereof in the medical field as vaccines for the prevention and treatment of COVID-19 infection.

12 Claims, 40 Drawing Sheets

Specification includes a Sequence Listing.

(56) References Cited

FOREIGN PATENT DOCUMENTS

WO WO-2005120565 A2 * 12/2005 .......... C07K 14/005

OTHER PUBLICATIONS

Fonseca et al. (Vaccine. 2018; 36 (20): 2799-2808).*
Wang et al. (Frontiers in Microbiology. Feb. 28, 2020; 11: 298).*
Ren et al. (Vaccine. Jun. 24, 2020; 38: 5653-5658).*
Andre et al., "DNA electrotransfer: its principles and an updated review of its therapeutic applications," Gene Therapy (2004) 11, S33-S42.
Aurisicchio et al. "Safety, tolerability and immunogenicity of V934/V935 hTERT vaccination in cancer patients with selected solid tumors: a phase I study," J Transl Med (2020) 18:39.
Buchholz et al., "Contributions of the structural proteins of severe acute respiratory syndrome coronavirus to protective immunity," PNAS (2004), vol. 101, No. 26, pp. 9804-9809.
Chan et al. "Middle East Respiratory Syndrome Coronavirus: Another Zoonotic Betacoronavirus Causing SARS-Like Disease," Clinical Microbiology Reviews (2015), vol. 28, No. 2, pp. 465-522.
Cheng et al., "Severe Acute Respiratory Syndrome Coronavirus as an Agent of Emerging and Reemerging Infection," Clinical Microbiology Reviews, Oct. 2007, p. 660-694.
Corti et al., "Prophylactic and postexposure efficacy of a potent human monoclonal antibody against MERS coronavirus," PNAS (2015), vol. 112, No. 33, pp. 10473-10478.
Diaz et al., "Phase 1 studies of the safety and immunogenicity of electroporated HER2/CEA DNA vaccine followed by adenoviral boost immunization in patients with solid tumors," Journal of Translational Medicine 2013, 11:62.
Durieux et al., "In vivo gene electrotransfer into skeletal muscle: effects of plasmid DNA on the occurrence and extent of muscle damage," J Gene Med 2004; 6: 809-816.
Forni et al., "Molecular Evolution of Human Coronavirus Genomes," Trends in Microbiology, Jan. 2017, vol. 25, No. 1, pp. 35-48.
Gothelf et al., "What you always needed to know about electroporation based DNA vaccines," Human Vaccines & Immunotherapeutics (2012), vol. 8, Iss 11, pp. 1694-1702.
Li et al., "Structure of SARS Coronavirus Spike Receptor-Binding Domain Complexed with Receptor," Science (2005), vol. 309, pp. 1864-1868.
Luo et al., "Evaluation of Antibody-Dependent Enhancement of SARS-CoV Infection in Rhesus Macaques Immunized with an Inactivated SARS-CoV Vaccine," Virologica Sinica (2018) 33:201-204.
Lurquin et al., "Gene Transfer by Electroporation," Molecular Biotechnology (1997), vol. 7, pp. 5-35.
Martina et al., "SARS virus infection of cats and ferrets," Nature (2005), vol. 425, pp. 915.
Mathiesen et al., "Electropermeabilization of skeletal muscle enhances gene transfer in vivo," Gene Therapy (1999), vol. 6, pp. 508-514.
Mir et al., "High-efficiency gene transfer into skeletal muscle mediated by electric pulses," Proc. Natl. Acad. Sci. (1999), vol. 99, pp. 4262-4267.
Neumann et al., "Fundamentals of electroporative delivery of drugs and genes," Bioelectrochemistry and Bioenergetics (1999), vol. 48, pp. 3-16.
Rizzuto et al., "Gene Electrotransfer Results in a High-Level Transduction of Rat Skeletal Muscle and Corrects Anemia of Renal Failure," Human Gene Therapy (2000), vol. 11, pp. 1891-1900.
Shi et al., "Susceptibility of ferrets, cats, dogs, and other domesticated animals to SARS-coronavirus 2," Science (2020), vol. 368, pp. 1016-1020.
Song et al., "Cryo-EMstructure of the SARS coronavirus spike glycoprotein in complex with its host cell receptor ACE2," PLOS Pathogens (2018), vol. 14, pp. 1-19.
Tai et al., "Characterization of the receptor-binding domain (RBD) of 2019 novel coronavirus: implication for development of RBD protein as a viral attachment inhibitor and vaccine," Cellular & Molecular Immunology (2020), vol. 17, pp. 613-620.
Tetro, "Is COVID-19 receiving ADE from other coronaviruses?," Microbes and Infection (2020), vol. 22, pp. 72-73.
Traggiai et al., "An efficient method to make human monoclonal antibodies from memory B cells: potent neutralization of SARS coronavirus," Nature Medicine (2004), vol. 10, No. 8, pp. 871-875.
Tseng et al., "Immunization with SARS Coronavirus Vaccines Leads to Pulmonary Immunopathology on Challenge with the SARS Virus," PLOS One (2012), vol. 7, Iss. 4, pp. 1-13.
Van Den Brand et al., "Pathology of Experimental SARS Coronavirus Infection in Cats and Ferrets," Vet Pathol. (2008), vol. 45, pp. 551-562.
Walls et al., "Unexpected Receptor Functional Mimicry Elucidates Activation of Coronavirus Fusion," Cell (2019), vol. 176, pp. 1026-1039.
Walls et al., "Structure, Function, and Antigenicity of the SARSCoV-2 Spike Glycoprotein," Cell (2020), vol. 180, pp. 281-292.
Wan et al., "Molecular Mechanism for Antibody-Dependent Enhancement of Coronavirus Entry," Journal of Virology (2020), vol. 94, Iss. 5, pp. 1-15.
Wang et al., "Antibody-dependent SARS coronavirus infection is mediated by antibodies against spike proteins," Biochemical and Biophysical Research Communications (2014), vol. 451, pp. 208-214.
Yang et al., "Evasion of antibody neutralization in emerging severe acute respiratory syndrome coronaviruses," PNAS (2005), vol. 102, No. 3, pp. 797-801.
Yao et al., "Patient-derived mutations impact pathogenicity 1 of SARS-CoV-2," Cell Discovery (2020), vol. 6, No. 76, pp. 1-46.
Yip et al., "Antibody-dependent infection of human macrophages by severe acute respiratory syndrome coronavirus," Virology Journal (2014), vol. 11, No. 82, pp. 1-11.
Zhang et al., "SARS-CoV-2 neutralizing serum antibodies in cats: a serological investigation," bioRxiv (2020).
Zumla et al., "Coronaviruses—drug discovery and therapeutic options," Nature Reviews (2016), vol. 15, pp. 327-347.
"UniProtKB—PODTC2 (SPIKE_SARS2)", UniProt, Apr. 22, 2020, XP002801761.
Wanbo Tai et al., "Characterization of the receptor-binding domain (RBD) of 2019 novel coronavirus: implication for development of RBD protein as a viral attachment inhibitor and vaccine", Cellular & Molecular Immunology, vol. 17, No. 6, Mar. 19, 2020, pp. 613-620, XP055727464, ISSN: 1672-7681, DOI: 10.1038/s41423-020-0400-4.
International Search Report and Written Opinion of the International Searching Authority in PCT/IT2021/050130 issued Apr. 11, 2021.

* cited by examiner

A) sp|P59594|SPIKE_CVHSA Spike glycoprotein OS=Human SARS coronavirus OX=694009 GN=S PE=1 SV=1

Sequence ID: Query_25681 Length: 1255 Number of Matches: 1

Range 1: 1 to 1255 Graphics

| NW Score | Identities | Positives | Gaps |
|---|---|---|---|
| 5204 | 971/1277(76%) | 1109/1277(86%) | 26/1277(2%) |

```
Query  1     MFVFLVLLPLVSSQCVNLTTRTQ---LPPAYTN---SFTRGVYYPDKVFRSSVLHSTQDLFL  56
Sbjct  1     ..I..LF.T.T.GSDLDRC.TFDDVQA.N..QHT.SM.......EI...DT.YL......  60

Query  57    PFFSNVTWFHAIHVSGTNGTKRFDNPVLPFNDGVYFASTEKSNIIRGWIFGTTLDSKTQS  116
Sbjct  61    ..Y....G..T.NHT-------.G...I..K..I...A.....VV...V..S.MNN.S..  113

Query  117   LLIVNNATNVVIKVCEFQFCNDPFLGVYYHKNNKSWMESEFRVYSSANNCTFEYVSQPFL  176
Sbjct  114   VI.I..S.....RA.N.EL.DN..FA.----SKPMGTQTHTMIFDN.F.....I.DA.S  169

Query  177   MDLEGKQGNFKNLREFVFKNIDGYFKIYSKHTPINLVRDLPQGFSALEPLVDLPIGINIT  236
Sbjct  170   L.VSE.S....H.......K..FLYV.KGYQ..DV.....S..NT.K.IFK..L.....  229

Query  237   RFQTLLALHRSYLTPGDSSSGWTAGAAAYYVGYLQPRTFLLKYNENGTITDAVDCALDPL  296
Sbjct  230   N.RAI.TA----FS.AQDI--.GTS....F....K.T..M...D...........SQN..  283

Query  297   SETKCTLKSFTVEKGIYQTSNFRVQPTESIVRFPNITNLCPFGEVFNATRFASVYAWNRK  356
Sbjct  284   A.L..SV...EID...........V.SGDV..................K.F.....E..  343

Query  357   RISNCVADYSVLYNSASFSTFKCYGVSPTKLNDLCFTNVYADSFVIRGDEVRQIAPGQTG  416
Sbjct  344   K.............TF..........A........S........VK..D..........  403

Query  417   KIADYNYKLPDDFTGCVIAWNSNNLDSKVGGNYNYLYRLFRKSNLKPFERDISTEIYQAG  476
Sbjct  404   V...........M...L...TR.I.ATST.....K..YL.HGK.R.......NVPFSPD  463

Query  477   STPCNGVEGFNCYFPLQSYGFQPTNGVGYQPYRVVVLSFELLHAPATVCGPKKSTNLVKN  536
Sbjct  464   GK..TP-PAL...W..ND...YT.T.I...............N........L..D.I..  522

Query  537   KCVNFNFNGLTGTGVLTESNKKFLPFQQFGRDIADTTDAVRDPQTLEILDITPCSFGGVS  596
Sbjct  523   Q................P.S.R.Q........VS.F..S....K.S.....S........  582

Query  597   VITPGTNTSNQVAVLYQDVNCTEVPVAIHADQLTPTWRVYSTGSNVFQTRAGCLIGAEHV  656
Sbjct  583   .......A.SE...........D.ST.........A..I....N.....Q..........  642

Query  657   NNSYECDIPIGAGICASYQTQTNSPRRARSVASQSIIAYTMSLGAENSVAYSNNSIAIPT  716
Sbjct  643   DT................H.VS----LL..TSQK..V........DS.I.....T.....  698

Query  717   NFTISVTTEILPVSMTKTSVDCTMYICGDSTECSNLLLQYGSFCTQLNRALTGIAVEQDK  776
Sbjct  699   ..S..I...VM....A......N...........A..................S...A...R  758

Query  777   NTQEVFAQVKQIYKTPPIKDFGGFNFSQILPDPSKPSKRSFIEDLLFNKVTLADAGFIKQ  836
Sbjct  759   ..R........M....TL.Y.............L..T....................M..  818

Query  837   YGDCLGDIAARDLICAQKFNGLTVLPPLLTDEMIAQYTSALLAGTITSGWTFGAGAALQI  896
Sbjct  819   ..E.....N.......................D...A..A..VS..A.A............  878

Query  897   PFAMQMAYRFNGIGVTQNVLYENQKLIANQFNSAIGKIQDSLSSTASALGKLQDVVNQNA  956
Sbjct  879   ..........................Q......K..SQ..E..TT.ST.............  938

Query  957   QALNTLVKQLSSNFGAISSVLNDILSRLDKVEAEVQIDRLITGRLQSLQTYVTQQLIRAA  1016
Sbjct  939   ............................................................  998

Query  1017  EIRASANLAATKMSECVLGQSKRVDFCGKGYHLMSFPQSAPHGVVFLHVTYVPAQEKNFT  1076
Sbjct  999   ....................................A..............S..R...  1058

Query  1077  TAPAICHDGKAHFPREGVFVSNGTHWFVTQRNFYEPQIITTDNTFVSGNCDVVIGIVNNT  1136
Sbjct  1059  .......E...Y.........F...S..I.....FS.......................I...  1118

Query  1137  VYDPLQPELDSFKEELDKYFKNHTSPDVDLGDISGINASVVNIQKEIDRLNEVAKNLNES  1196
Sbjct  1119  ............................................................  1178

Query  1197  LIDLQELGKYEQYIKWPWYIWLGFIAGLIAIVMVTIMLCCMTSCCSCLKGCCSCGSCCKF  1256
Sbjct  1179  ....................V.................L..............A.........  1238

Query  1257  DEDDSEPVLKGVKLHYT  1273
Sbjct  1239  .................  1255
```

Query = SEQ ID NO:19

Sbjct = SEQ ID NO:18

```
mfvflvllplvssqcvnlttrtqlppaytnsftrgvyypdkvfrssvlhstqdlf
1        10        20        30        40        50

lpffsnvtwfhaihvsgtngtkrfdnpvlpfndgvyfasteksniirgwifgttl
    60        70        80        90        100       110

dsktqslliivnnatnvvikvcefqfcndpflgvyyhknnkswmesefrvyssann
         120       130       140       150       160

ctfeyvsqpflmdlegkqgnfknlrefvfknidgyfkiyskhtpinlvrdlpqgf
    170       180       190       200       210       220

saleplvdlpiginitrfqtllalhrsyltpgdsssgwtagaaayyvgylqprtf
         230       240       250       260       270

llkynengtitdavdcaldplsetkctlksftvekgiyqtsnfrvqptesivrfP
    280       290       300       310       320       330

          I                         FFFFFF
NITNLCPFGEVFNATRFASVYAWNRKRISNCVADYSVLYNSASFSTFKCYGVSPT
         340       350       360       370       380

                                                     S
KLNDLCFTNVYADSFVIRGDEVRQIAPGQTGKIADYNYKLPDDFTGCVIAWNSNN
    390       400       410       420       430       440

         Y
     K Y   F     R R         I     S G G         F   F P
LDSKVGGNYNYLYRLFRKSNLKPFERDISTEIYQAGSTPCNGVEGFNCYFPLQSY
         450       460       470       480       490

        Q Y  H       Q  P S
GFQPTNGVGYQPYRVVVLSFELLHAPatvcgpkkstnlvknkcvnfnfngltgtg
    500       510       520       530       540       550

vltesnkkflpfqqfgrdiadttdavrdpqtleilditpcsfggvsvitpgtnts
         560       570       580       590       600

nqvavlyqdvnctevpvaihadqltptwrvystgsnvfqtragcligaehvnnsy
    610       620       630       640       650       660

ecdipigagicasyqtqtnsprrarsvasqsiiaytmslgaensvaysnnsiaip
         670       680       690       700       710

tnftisvtteilpvsmtktsvdctmyicgdstecsnlllqygsfctqlnraltgi
    720       730       740       750       760       770

aveqdkntqevfaqvkqiyktppikdfggfnfsqilpdpskpskrsfiedllfnk
         780       790       800       810       820
```

SEQ ID NO:20

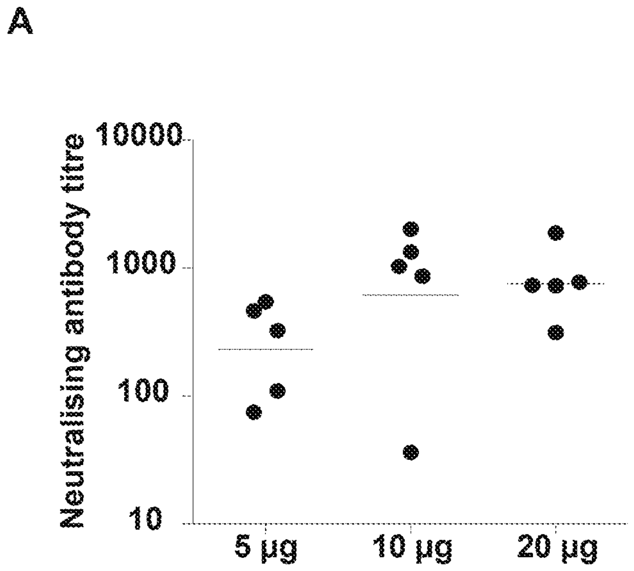
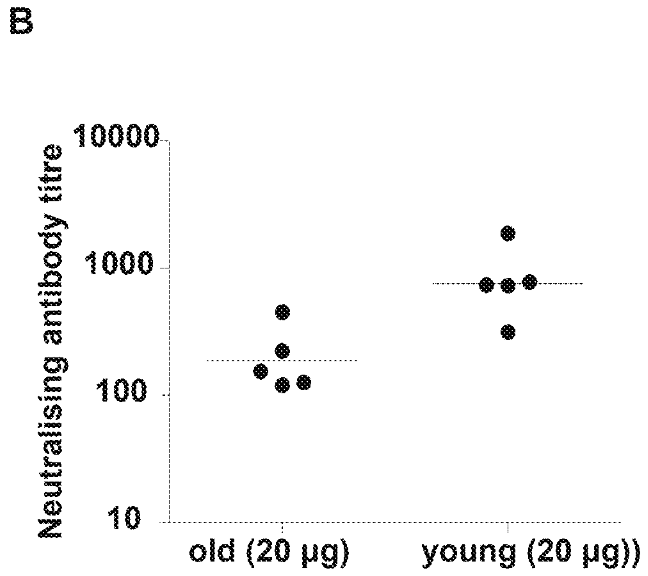
Fig. 17

POLYNUCLEOTIDES ENCODING SARS-COV-2 ANTIGENS AND USE THEREOF IN THE MEDICAL FIELD AS VACCINES

CROSS-REFERENCE TO RELATED APPLICATIONS

This application is the U.S. National Phase under 35 U.S.C. § 371 of International Application PCT/IT2021/050130, filed Apr. 30, 2021, and published as WO 2021/220319A1 on Nov. 4, 2021, which claims the benefit of Italian Application No. 102020000009625, filed Apr. 30, 2020. Any and all applications for which a foreign or a domestic priority is claimed is/are identified in the Application Data Sheet filed herewith and is/are hereby incorporated by reference in their entireties under 37 C.F.R. § 1.57.

REFERENCE TO ELECTRONIC SEQUENCE LISTING

The present application is filed along with an Electronic Sequence Listing. The Electronic Sequence Listing is provided as a file entitled BARZ068.001APCSEQLIST.TXT which is 94,032 bytes in size, created on Apr. 30, 2023. The information in the Electronic Sequence Listing is incorporated herein by reference in its entirety.

FIELD

The present invention relates to polynucleotides encoding SARS-CoV-2 antigens and use thereof in the medical field as vaccines. In particular, the invention relates to polynucleotides encoding antigens of the SARS-CoV-2 coronavirus spike protein and use thereof in the medical field as vaccines in the prevention and treatment of COVID-19 infection.

The spread of the new coronavirus disease called COVID-19, caused by the SARS-CoV-2 coronavirus and correlated to acute respiratory syndrome, has rapidly progressed into a pandemic. In a few months, from December 2019, COVID-19 spread throughout the world with over 2,959,929 cases and over 202,733 deaths confirmed as of 29 Apr. 2020, 10.00 am (WHO website).

This situation requires, with utmost urgency, the development of preventive agents and safe, effective therapies against SARS-CoV-2 infection. To date, no therapy or vaccine has been approved against the coronaviruses capable of infecting humans.

SUMMARY

The strategies currently in place to trigger an effective immune response in humans against SARS-CoV-2 are exploiting previous experiences with other coronaviruses such as SARS-CoV and MERS-CoV (1, 2). Since the SARS-CoV-2 virus shares an important similarity with these two lethal coronaviruses in terms of structure and sequence preservation, the immunisation strategies exploited against the SARS and MERS viruses have been adopted to guide the design of new SARS-CoV-2 vaccines (3).

Immunisation with one or more antigens of SARS-CoV-2 subunits, administered as purified proteins or expressed by viral vectors, an RNA or a DNA, is one of the possible approaches for the design of a vaccine.

The structural proteins decorating the surface of SARS-CoV-2 are among most important targets for vaccination. They include the spike (S) protein of the shell, the small envelope (E) protein, the matrix (M) protein and the nucleocapsid (N) protein (4).

An initial study on a recombinant vector that expresses the SARS-CoV S protein indicated that this protein is highly immunogenic and protective against SARS-CoV in hamsters, whereas the N, M and E proteins, by contrast, did not provide a significant contribution to a neutralising antibody response or protective immunity (5).

In light of the foregoing and given that the coronavirus S protein is a glycoprotein exposed on the surface and mediates the entry into host cells by interacting with the angiotensin-converting enzyme 2 (ACE2), it has rapidly become the main molecular target to be neutralised with antibodies and the focus of therapeutic and vaccine design (6).

Evidence of the S protein's key role in the fight against coronavirus infection has emerged from studies on the neutralising antibodies in humans from rare memory B cells of individuals infected by SARS-CoV (7) or MERS-CoV (8). In these studies, the antibodies directed against the SARS-CoV S protein showed to be effective in inhibiting the entry of the virus into host cells. More recently, it was discovered that the SARS-CoV S protein induces polyclonal antibody responses and powerfully neutralises the entry of SARS-CoV-2 into cells—mediated precisely by the S protein—thus further encouraging the use of this molecular target for vaccination and immunotherapies (9).

Structural studies on antibodies in complex with the S proteins of SARS-CoV and MERS-CoV have provided information on the mechanism of competitive inhibition on the receptor (10). The receptor binding domain (RBD) in the SARS-CoV-2 S protein has been identified and it has been discovered that it binds strongly to the ACE2 receptor. The antibodies specific for the SARS-CoV RBD can cross-react with the SARS-CoV-2 RBD protein and the SARS-CoV-2 virus is neutralised by SARS-CoV-2 RBD-induced antisera, providing further evidence that a vaccine having this domain of the S protein as a target could be effective (11).

The molecular heterogeneity and evolution of SARS-CoV-2 have aroused concerns about the scope and effectiveness of protection with specific types of vaccines and the possible escape of the virus from the selective pressure exerted by the immune system.

A new study has discovered that the ability of the new coronavirus to mutate has been largely underestimated and different strains can explain the different impacts of the disease in various parts of the world (12). Sars-CoV-2 has acquired mutations capable of substantially changing its pathogenicity, providing the first concrete evidence that the mutation could influence the severity of the disease or the damage in the host. The viral strains isolated from 11 randomly selected Covid-19 patients in Hangzhou, in the eastern province of Zhejiang, were tested for their ability to infect and kill cells. These viral isolates showed a significant variation in cytopathic effects and viral load, up to 270 times, when Vero-E6 cells were infected, an intrapersonal variation and 6 different mutations in the S protein, including 2 different SNVs which led to the same missense mutation. Therefore, direct evidence was provided that SARS-CoV-2 has acquired mutations capable of substantially changing its pathogenicity. The most deadly mutations in the patients in Zhejiang were found in the majority of the patients across Europe, whereas the milder strains were the predominant varieties found in some parts of the United States, such as the state of Washington. This discovery could shed light on the differences in regional mortality. The pandemic infection and mortality rate vary from country to country and many explanations have been proposed, such as age, health conditions or even blood group. In hospitals, Covid-19 has been treated as one disease and patients have received the same treatment irrespective of the infectious strain. The development of drugs and vaccines must thus necessarily take account of the impact of these accumulating mutations. However, the observation that a heterotypical response blocks the entry into host cells mediated by the SARS-CoV-2 S protein and the analysis of the sequence and structural conservation of the SARS-CoV-2 and SARS-CoV S protein suggest that immunity against one virus can potentially provide protection against related viruses.

In a recent study, it was discovered that ferrets and cats are highly sensitive to SARS-CoV-2, whereas dogs have low susceptibility and livestock, including pigs, chickens and ducks, is not sensitive to the virus (13).

Among preclinical models, in fact, ferrets have often been used as an animal model for the study of human respiratory viruses (14, 15). Unlike flu viruses and other human SARS-coronaviruses, which replicate in the upper and lower respiratory tract, SARS-CoV-2 replicates only in the nasal turbinate, soft palate and tonsils of ferrets. It can also replicate in the digestive tract, as viral RNA was detected in rectal swabs of virus-infected ferrets, but the virus was not detected in the lung lobes, even after the ferrets were inoculated intratracheally with the virus. The fact that SARS-CoV-2 replicates efficiently in the upper respiratory tract of ferrets thus makes them a candidate animal model for the assessment of antiviral drugs or candidate vaccines against COVID-19.

Among domestic animals, SARS-CoV-2 efficiently replicates in cats and is transmitted to other cats. Ferrets and cats have only two differences in amino acids in the regions in contact between the SARS-CoV-2 spike protein and ACE2. It has in fact been reported that cats in Wuhan are seropositive for SARS-CoV-2 (16). SARS-CoV-2 monitoring in cats must thus be considered in addition to the elimination of COVID-19 in humans.

In Denmark, in the month of June 2020, 214 human cases of COVID-19 with SARS-CoV-2 variants associated with farmed mink were identified, including 12 cases with a single variant reported on 5 November. All 12 cases were identified in September 2020 in northern Jutland, in Denmark. The cases had an age comprised between 7 and 79 years and eight had a link with the mink farming industry and four cases came from the local community. The initial observations suggested that the clinical presentation, severity and transmission between infected persons are similar to those of other circulating SARS-CoV-2 viruses. However, this variant, called the “cluster 5” variant, showed a combination of mutations or changes that had not been previously observed. The implications of the changes identified in this variant are not yet well understood. The preliminary results indicated that this particular mink-associated variant identified both in mink and in the 12 human cases had a moderately reduced sensitivity to neutralising antibodies. The mink were thus infected following exposure to infected human beings. Mink can act as a reservoir of SARS-CoV-2, transmitting the virus among one another, and represent a risk of propagation of the virus from mink to humans. People can in turn transmit this virus within human population. Moreover, a return of the infection (transmission from humans to mink) can occur. When viruses move between human and animal populations, genetic modifications may take place in the virus. These changes can be identified by sequencing the entire genome and, once they are found, experiments can be conducted to study the possible implications of these changes on the disease in human beings. The Danish government thus decided in the month of November 2020 to cull 17 million mink to prevent a mass spread to humans, with considerable damage to the fur export industry.

One of the most important problems regarding the current COVID-19 coronavirus pandemic is the possible worsening of the disease by immunotherapies as a consequence of an antibody-dependent enhancement (ADE) of the infection with SARS-CoV-2 (17). The ADE effect has been one of the main concerns for epidemiology, the development of vaccines and antibody-based pharmacological therapy, when it was discovered that the virus' entry into the target cell might be mediated by the Fc receptor II and not by ACE2 as per conventional wisdom (18). It has been suggested that ADE might explain the geographical differences in the severity of COVID-19 due to previous exposure to similar antigenic epitopes (19). Another study demonstrated that the antibody against the SARS-CoV S protein mediates the enhanced infection of cells of monocytic origin. However, macrophages with ADE infection do not support productive replication of SARS-CoV and in fact no detectable release of the virus of the progeny was observed (20). In a mouse model of SARS-CoV vaccination with different approaches, including the inactivated virus, the protein vaccine based on the recombinant S protein led to pulmonary immunopathology. However, despite the worsening of the pulmonary histopathological profile of the vaccinated mice, all the SARS-CoV vaccines induced antibodies and protection against SARS-CoV infection (21). It was discovered that higher antisera concentrations are capable of neutralising SARS-CoV infection, whereas highly diluted antisera significantly increased SARS-CoV infection. The results of infectivity tests indicate that ADE is mainly mediated by diluted antibodies against the S protein (22). However, the relevance of ADE in coronavirus infection is not yet wholly clear, as no direct evidence was found in the vaccination model. In fact, it was demonstrated that the vaccination of Rhesus monkeys with attenuated SARS-CoV did not induce exacerbation of the infection even several weeks later, when the antibody concentration had significantly decreased (23).

In light of the foregoing, there is clearly a need to have a vaccine for the prevention and treatment of the disease caused by SARS-CoV-2.

The molecular design of a vaccine against SARS-CoV-2 should therefore follow a strategy that is highly specific for regions that can block the interaction of the virus with its natural receptor and minimise the risk of inducing an ADE effect. At the same time, a very efficient vaccine platform capable of inducing not only antibodies, but also a cell-mediated response, is highly desirable.

Various companies and research institutes have thus launched the development of vaccines targeting the SARS-CoV-2 S protein. The different vaccination strategies have a different capability to induce in the host both a humoral response mediated by antibodies and a cellular response mediated by CD4 or CD8 T lymphocytes in preclinical models. This objective has been guided by the previous preclinical history of proven effectiveness of immunotherapies against the homologous protein of SARS-CoV.

When the sequence of the S protein of the new coronavirus SARS-CoV-2 was aligned with the SARS-CoV spike protein, an overall degree of similarity of about 76% was observed (see FIG. 1). It should be noted that half of the dissimilarities (~56%) resides in the N-terminal domain (residues 14-294, ID UNIPROT SARS-CoV-1 P59594) and a good ~24% in the three C-terminal domains called CTD1, CTD2 and CTD3 (residues 320-666, ID UNIPROT P59594 SARS-CoV-1) of the S1 subunit.

The remaining ~20% of dissimilarities between the two analysed proteins instead involves the S2 C-terminal subunit (residues 667-1190, ID UNIPROT P59594 SARS-CoV), which is involved in the activity of viral fusion with the host membrane.

It is noted that in the new SARS-CoV-2 S protein the domains are not officially identified as CTD2 and CTD3. For example, in UNIPROT these domains are not associated with any nomenclature, whilst in a cryo-EM study in Science they are called SD1 and SD2. In this context said domains will be indicated as CTD2 and CTD3 on the basis of the domain nomenclature used for SARS-CoV-1.

CTD1 (residues 306-527, ID UNIPROT SARS-CoV-1 P59594), also called the "receptor-binding domain" (RBD), is responsible for the recognition of the ACE2 cell receptor. Although several sequence variations have been identified in the RBD of SARS-CoV-2 compared to the more ancestral counterpart SARS-CoV-1, the overall sequence similarity between the 2 domains is about 75%, thus giving rise to the hypothesis that both viruses share the same ACE2 receptor. A hypothesis by now confirmed by several published scientific papers. Previous structural studies identified 14 amino acids within the human SARS-CoV RBD which contact the ACE2 receptor (35). Of these, 8 are conserved whilst 6 are mutated in the RBD of the new coronavirus, including 2 critical residues in positions 479 and 487. However, recent analyses have suggested that these changes might not influence the ability of the recently identified coronavirus to recognise ACE2 (18).

According to the present invention, vaccines have now been developed which are based on a construct of plasmid DNA expressing specific domains of the SARS-CoV-2 virus S protein including the RBD region, for the prevention and treatment of the disease caused by the SARS-CoV-2 virus. The system is called COVID-eVax. During the experimental process described further below an attempt was made to understand which constructs were more immunogenic by means of a seroconversion assay in vaccinated mice and which were capable of inducing a greater antibody concentration.

In particular, example 1 describes the criterion with which the functionally relevant regions of the S protein were identified. The criterion also took account of the probability of a three-dimensional conformation closer to the physiological one.

Example 2 shows the analysis of the S protein of 1977 sequenced genomes of SARS-CoV-2, where it is highlighted that there is a total of 26 mutations and the frequency of mutations in the RBD region is thus very low (1.3%).

In example 3, nucleotide sequences optimised for codon usage were generated and they were inserted into a plasmid DNA vector, which was administered by electroporation (DNA-EP).

In example 4, groups of mice were vaccinated using DNA-EP technology. In particular, different electrical conditions were used to obtain a better gene expression and induction of the immune response.

Example 5 shows how the RBD-Fc and RBD-6His proteins were produced for the seroconversion assays and antibody titre. These proteins are also used for the generation of anti-spike monoclonal antibodies.

Example 6 shows the results obtained in the seroconversion of the animals and the level of the antibody titre obtained after the vaccination and using the recombinant RBD-6His protein.

Example 7 indicates that the antibodies generated are capable of binding to the S protein expressed on surface of cells, thus in the native conformation thereof.

Example 8 shows the data of a functional assay on the SARS-CoV-2 virus, where it is seen that the sera of vaccinated animals are capable of blocking the infectivity of the virus in vitro on cells.

Example 9 indicates how the COVID-eVax vaccine will be administered to the subject.

On the basis of the experimental results, it was observed that all of the optimised nucleotide sequences and the constructs comprising them are capable of generating antibodies against the RBD region. In particular, precisely the constructs containing a specific region of the S protein, and not the whole S protein, yielded the highest antibody titre and the greatest neutralising power against SARS-CoV-2 when comprising the RBD region.

This result is surprising as many studies have demonstrated that the full-length S protein of SARS and MERS gave higher antibody titres.

Examples 10 to 17 and example 19 regard a particular embodiment of the vaccine according to the invention, comprising an optimised nucleotide sequence encoding for the RBD fused to a specific leader sequence. In particular, the influence of the TPA secretion leader sequence on the expression and on the immunogenicity of the vaccine, the influence of the optimised nucleotide sequence of the invention on the expression of the RBD, the dose/immunological response to vaccination, the presence of neutralising antibodies in the serum of vaccinated mice, the cellular responses in the vaccinated mice, the presence of RBD-specific antibodies in the lungs and of T lymphocytes after intranasal inoculation of the RBD protein, the immunogenicity in rats and the ability of the sera to block the variants of concern (VOCs) of SARS-CoV-2, the binding competition between the protein produced by the vaccine and the virus with respect to the ACE-2 receptor and the effectiveness on mice transgenic for human ACE-2 were observed.

Example 18 concerns the effectiveness of the vaccine according to the present invention against the variants of SARS-CoV-2 using optimised nucleotide sequences of the wild-type RBD protein and the VOCs of SARS-CoV-2.

Examples 20 and 21 concern the treatment of mice and cats with one embodiment of the vaccine according to the present invention based on amplicons obtained by PCR.

In particular, the present invention proposes the use of a vaccine against SARS-CoV-2 in the form of a DNA vaccine to be administered by electroporation or other systems that may increase gene expression in vivo. In example 4 it is shown that the optimal gene expression of the transgene depends on an efficient transduction system such as in vivo electroporation and varies based on the method of use thereof. Alternatively, the vaccine according to the present invention can be administered for example in the form of liponanoparticles, also without electroporation.

The effectiveness of the vaccination system and of the immunological correlates such as, for example, the results of the analysis of the specific responses depends, in fact, on the electrical conditions used.

The vaccine of the present invention provides the important advantage of being able to be administered a number of times over time without inducing neutralising antibodies against the vaccine itself, as occurs, by contrast, in the case of viral vector-based vaccines.

According to the present invention, the virus sequences are selected from alignments of genomes isolated in China and in various countries around the world in order to generate a vaccine capable of neutralising SARS-CoV-2 both in specific geographic regions and at a global level.

The immune response mediated by T cells recognises the peptides of the virus as non-self and thus activates a cytotoxic response to kill the cells expressing them. The term non-self is used to indicate the responses against the viral epitopes which eliminate the cell containing the virus and hence the infection.

A further important aspect of the vaccine against COVID-19 according to the present invention is the possibility of striking a number of mutations accumulated by the virus over time. In particular, this approach is dependent on the biological function of the S protein and can be redesigned, following the mutational evolution of the coronavirus over time, i.e. it is possible to insert new sequences identified by epidemiological analysis into the vaccine, as shown in example 18.

The vaccine according to the present invention is capable of inducing in the patient a type B and type T cellular immune response against the SARS-CoV-2 S protein.

A further advantage of the present invention is the possibility of administration without the need for a complex formulation as in the case of lipid particles with peptides or RNA or in the case of nanoparticles of another nature loaded with a vaccine.

It is therefore specific object of the present invention a polynucleotide encoding for an amino acid sequence, an expression vector comprising said polynucleotide, or a pharmaceutical composition comprising said polynucleotide or expression vector in combination with one or more pharmaceutically acceptable excipients and/or adjuvants, wherein the polynucleotide comprises or consists of a sequence selected from SEQ ID NO:1 and a sequence having a percent identity greater than or equal to 80% compared to sequence SEQ ID NO:1, preferably greater than or equal to 81%, 82%, 83%, 84%, 85%, 86%, 87%, 88%, 89%, 90%, 91%, 92%, 93%, 94%, 95%, 96%, 97%, 98% or 99%, said sequence encoding for an amino acid sequence consisting of the RBD domain of the S1 subunit of the spike protein of the SARS-CoV-2 virus or of variants thereof (i.e. variants of the SARS-CoV-2 virus).

According to one embodiment of the present invention, said sequence having a percent identity greater than or equal to 80% compared to the sequence SEQ ID NO:1 can be selected from SEQ ID NO:14, SEQ ID NO:15, and SEQ ID NO:21, wherein the sequences SEQ ID NO:14, SEQ ID NO:15 and SEQ ID NO: 21, shown in example 18, are the optimised nucleotide sequences encoding respectively for the RBD of the British variant or lineage B.1.1.7 (SEQ ID NO:22), the RBD of the South African variant or lineage B.1.351 (SEQ ID NO:23) and the RBD of the Brazilian variant or Lineage P1 (SEQ ID NO:24).

According to one embodiment of the present invention, said polynucleotide can further comprise one or more sequences encoding for one, more than one or all of the domains selected from among NTD, CTD2 and CTD3 of the S1 subunit of the Spike protein of the SARS-CoV-2 virus or of variants thereof.

In particular, according to one embodiment of the present invention the polynucleotide can comprise or consist of the sequence SEQ ID NO:2 which encodes for an amino acid sequence consisting in the NTD and RBD domains, from the N-terminal end to the C-terminal end, of the S1 subunit of the spike protein of the SARS-CoV-2 virus.

According to a further embodiment of the invention, the polynucleotide can comprise or consist of the sequence SEQ ID NO:3 which encodes for an amino acid sequence consisting in the NTD, RBD, CTD2 and CTD3 domains, from the N-terminal end to the C-terminal end, of the S1 subunit of the spike protein of the SARS-CoV-2 virus.

According to another aspect of the invention, the polynucleotide can comprise or consist of the sequence SEQ ID NO:5 which encodes for an amino acid sequence consisting in the spike protein of the SARS-CoV-2 virus.

According to one embodiment of the invention, the polynucleotide can further comprise one or more sequences encoding for one or more leader sequences, such as, for example, the secretion leader sequence of the tissue plasminogen activator (TPA), of IgK, of growth hormone, of serum albumin or of alkaline phosphatase, preferably of the tissue plasminogen activator (TPA). The leader sequence is bound to the N-terminal end of the amino acid sequence.

In particular, said polynucleotide can comprise or consist of a sequence selected from SEQ ID NO:1, SEQ ID NO:14, SEQ ID NO:15 or SEQ ID NO:21, preferably SEQ ID NO:1, fused to the C-terminal of the secretion leader sequence of the tissue plasminogen activator (TPA).

According to one embodiment of the present invention, the polynucleotide can further comprise one or more sequences encoding for one or more immunomodulating amino acid sequences, such as, for example, the fragment crystallisable (Fc) region, profilin-like protein of *Toxoplasma gondii* (PFTG) or a functional fragment derived therefrom, the B subunit of heat-labile toxin of *Escherichia coli* (LTB) or the tetanus toxin (TT). The amino acid sequence can also comprise one or more linker sequences.

According to another aspect of the invention, the polynucleotide can comprise or consist in the sequence SEQ ID NO:4 which encodes for an amino acid sequence consisting in the RBD domain of the S1 subunit of the SARS-CoV-2 virus spike protein, said domain being fused at the N-terminal end to the leader sequence of IgK and at the C-terminal end to the Fc immunomodulating sequence.

According to a further aspect of the invention, the polynucleotide can further comprise one or more sequences encoding for one or more antigenic sequences of the SARS-CoV-2 virus other than those of the S1 subunit of the SARS-CoV-2 virus spike protein.

According to the present invention, the expression vector can be selected from the group consisting of a plasmid, for example bacterial plasmids, an RNA, a replicating RNA, amplicons obtained by PCR, a viral vector such as, for example, adenovirus, poxvirus, vaccinia virus, fowlpox, herpes virus, adeno-associated virus (AAV), alphavirus, lentivirus, lambda phage, lymphocytic choriomeningitis virus, *Listeria* sp, *Salmonella* sp, preferably a plasmid or amplicons. Said vectors, in particular the amplicons, can comprise a promoter, a Kozak sequence and a polyadenylation signal, in addition to the optimised sequence of SARS-CoV-2.

According to one embodiment of the present invention, the polynucleotide which encodes for an amino acid sequence, expression vector comprising said polynucleotide, or pharmaceutical composition are in the form of a DNA, RNA or protein-based vaccine.

It is a further object of the present invention a polynucleotide which encodes for an amino acid sequence, an expression vector comprising said polynucleotide, or a pharmaceutical composition as defined above for use in the medical field.

The present invention further concerns a polynucleotide which encodes for an amino acid sequence, an expression vector comprising said polynucleotide, an amino acid sequence encoded by said polynucleotide, or a pharmaceutical composition comprising said polynucleotide, vector or amino acid sequence in combination with one or more pharmaceutically acceptable excipients and/or adjuvants, wherein said amino acid sequence comprises or consists of the RBD domain of the S1 subunit of the spike protein of the SARS-CoV-2 virus or of variants thereof (or variants of SARS-CoV-2), for use in the prevention and treatment of the disease caused by the SARS-CoV-2 virus, such as, for example, interstitial pneumonia.

In one embodiment of the present invention, said amino acid sequence comprises the RBD domain of the S1 subunit of the spike protein of the SARS-CoV-2 virus or of variants thereof and does not comprise further amino acid sequences other than the RBD of SARS-CoV-2 or of variants thereof, for example it does not comprise domains of the S1 subunit of the SARS-CoV-2 virus spike protein, such as NTD, CTD2 or CTD3.

According to one aspect of the present invention, again in relation to the above-mentioned use, said amino acid sequence can further comprise one or more domains of the S1 subunit of the SARS-CoV-2 virus spike protein selected from the group consisting of NTD, CTD2 and CTD3. In particular, the amino acid sequence can comprise for example RBD (spike-A), or from the N-terminal to the C-terminal it can comprise NTD and RBD (spike-B), or NTD, RBD, CTD2 and CTD3 (spike-C), or the entire spike sequence (spike-FL).

In one embodiment of the present invention, said amino acid sequence comprises the RBD domain, one or more domains selected from among NTD, CTD2 and CTD3 of the S1 subunit of the spike protein of the SARS-CoV-2 virus or of variants thereof and does not comprise further amino acid sequences of SARS-CoV-2 (or of variants of SARS-CoV-2) other than RBD, NTD, CTD2 and/or CTD3.

According to a further aspect of the present invention, again in relation to the above-mentioned use, said amino acid sequence can further comprise one or more antigenic sequences of the SARS-CoV-2 virus other than those of the S1 subunit of the SARS-CoV-2 virus spike protein.

According to a further aspect of the present invention, again in relation to the above-mentioned use, said amino acid sequence can further comprise one or more leader sequences such as, for example, the secretion leader sequence of the tissue plasminogen activator (TPA), of IgK, of growth hormone, of serum albumin or of alkaline phosphatase, preferably of the tissue plasminogen activator (TPA). The leader sequence is bound at the N-terminal end of the amino acid sequence. The leader sequence has the function of transporting the antigens outside the cell of the organism transfected with the vector or plasmid, for example by electroporation.

According to a further aspect of the present invention, again in relation to the above-mentioned use, said amino acid sequence can further comprise one or more immunomodulating amino acid sequences, such as, for example, the fragment crystallisable (Fc) region, profilin-like protein of *Toxoplasma gondii* (PFTG) or a functional fragment derived therefrom, the B subunit of heat-labile toxin of *Escherichia coli* of *Escherichia coli* (LTB) or the tetanus toxin (TT). For example, the amino acid sequence can be IgK-RBD-Fc. The amino acid sequence can also comprise one or more linker sequences. The use of leader sequences and immunomodulating sequences provides the technical effect of improving the antibody titre. In particular, the leader sequence has the function of transporting the antigens outside the cell of the organism transfected with the vector or plasmid, for example by electroporation. The leader sequence increases the secretion of the protein, whilst the immunomodulating sequences stimulate the immune system to produce antibodies. Furthermore, the polynucleotide according to the present invention can be under the transcriptional control of a promoter and a transcriptional regulatory element.

According to one embodiment of the present invention for the above-mentioned use, the polynucleotide can be selected from a polynucleotide as defined above and in the claims.

According to one embodiment of the present invention, the amino acid sequence can be selected from the group consisting of SEQ ID NO:7, SEQ ID NO:8, SEQ ID NO:9, SEQ ID NO:10, SEQ ID NO:11, SEQ ID NO:22, SEQ ID NO:23, SEQ ID NO:24.

In one embodiment of the present invention, said amino acid sequence comprises a sequence selected from SEQ ID NO:7, SEQ ID NO:8, SEQ ID NO:9, SEQ ID NO:10, SEQ ID NO:11, SEQ ID NO:22, SEQ ID NO:23 and SEQ ID NO:24 and does not comprise further amino acid sequences of SARS-CoV-2 (or of variants of SARS-CoV-2). According to a further embodiment, said amino acid sequence further comprises the TPA secretion leader sequence, it preferably comprises or consists of the sequence SEQ ID NO:7 fused to the TPA secretion leader sequence.

According to one aspect of the present invention, again in relation to the above-mentioned use, the polynucleotide which encodes for an amino acid sequence, the expression vector comprising said polynucleotide, the amino acid sequence encoded by said polynucleotide, or the pharmaceutical composition according to the present invention are used as a DNA, RNA or protein-based vaccine or as gene therapy.

As shown in the examples, the polynucleotides according to the present invention can be used as vaccines, since they are capable of immunising subjects against SARS-CoV-2 and variants thereof or can be used in therapy against SARS-CoV-2, since they generate an RBD protein capable of competing with the virus itself, thus limiting the entry thereof into the airways.

In particular, when the vaccine is a DNA or RNA vaccine, said vaccine can be administered by electroporation, preferably under the following conditions: 8 pulses of 20 msec, each at 110V, 8 Hz, with an interval of 120 msec between each of them, or 4 pulses of 5 msec, each at 40V, with an interval of 5 msec between each of them.

Electroporation enables the effectiveness of the vaccine to be optimised. It is preferably administered into the muscle or subcutaneously. The electroporation treatment can comprise the use of depth or surface electrodes, flat electrodes and/or needles. The vaccine according to the present invention can be administered in a single site or in several sites. For example, different vaccines against mutated viruses can be administered in part in the quadriceps of the right leg, the next ones, different from the first, in the quadriceps of the left leg, the next ones in the deltoid of the right arm, and the next ones in the deltoid of the left arm.

The principles of electroporation are very simple. The lipid membrane of a cell can be considered as a dielectric element interposed between the extracellular and cytoplasmic environments, which are both conductive. An electric field applied to a cell induces a transmembrane potential: when the dielectric potential of the membrane is exceeded, transient pores appear in the membrane, a process called electroporation (24, 25). If the electric field is maintained long enough, the membrane becomes permeable (electropermeabilisation) because the transient pores are stabilised and become large enough to allow charged macro molecules, such as DNA, to access the cytoplasm. The cells remain in a porated state for a limited period of time and close rapidly after the electric treatment ends. The duration of the electric pulse must be sufficiently short to avoid irreversible damage of the cell membrane and cell death. The transmembrane potential increases linearly with the intensity of the electric field applied, but above a certain threshold (generally 0.5-2 V) it decreases, indicating that the conductivity of the membrane increases due to the formation of hydrophilic pores (26,27). As the molecules of nucleic acids such as DNA or RNA are too large to penetrate through the hydrophilic pores simply by diffusion, an electrophoretic field must be maintained for a sufficient time in order to allow the polyanions to move and enter the cell. The DNA must be in proximity to the cell membrane before the electric field is applied. The DNA molecules pass through the membrane pores by means of an electrodiffusive process. It is postulated that the progression of the DNA towards the nucleus takes place through a combination of classic electrophoresis and passive diffusion according to a concentration gradient. Therefore, the pulses must be optimised so as to obtain the best combination of cell permeabilisation followed by the desired electrophoretic effect. In general, the pulse parameters are arbitrarily divided into short high-voltage pulses, greater than 400V/cm with a duration in the gamma range of psec and low-voltage pulses, less than a 400 V/cm with a duration in the interval of msec. An efficient gene transfer has been demonstrated using either only a sequence of high-voltage pulses or only low-voltage pulses. However, in theory, the most effective strategy seems to be a combination of short initial high-voltage pulses followed by a sequence of longer lasting low-voltage pulses. Protein expression in muscle is usually improved 100-1000 times after DNA electroporation (DNA-EP) compared to the injection of naked DNA, thanks above all to greater cellular absorption (14-16). Various devices for DNA-EP exist. The most advanced technologies are the ones being developed by Inovio Pharmaceuticals, Ichor Medical Systems and IGEA.

Skeletal muscle is the most frequent target organ for DNA-EP. Skeletal muscles are easily accessible beneath the skin and are made up of post-mitotic cells capable of long-term expression of the transgene after transfection (28-31). Furthermore, the tissue damage is rapidly repaired, without signs of muscle degeneration (32). Muscle DNA-EP is an invasive procedure that requires needles for injection of the nucleic acid, followed by the electric discharge. In small animals this is achieved with flat electrodes positioned on the skin around the injected volume, whereas in larger species, including humans, it requires an array of needles inserted into the tissue. In clinical studies, these procedures have demonstrated to be well tolerated and not to cause severe pain (33, 34).

The method of administration of the vaccine is not limited solely to plasmid DNA, as it can be given in the form of peptides or viral vectors in a prime-boost sequence. The plasmid vaccine with EP can be used for maintaining the immune response over time after viral vaccines, which are neutralized by the immune response against the viral vector already after the first administration, i.e., adenovirus-derived vectors.

According to one embodiment of the present invention, when the vaccine is a DNA or RNA vaccine, said vaccine can be administered in the form of liponanoparticles, for example intramuscularly, wherein said liponanoparticles comprise said polynucleotide or vector according to the present invention.

According to the present invention, said expression vector can be selected from the group consisting of a plasmid, for example bacterial plasmids, an RNA, a replicating RNA, amplicons obtained by PCR, a viral vector such as, for example, adenovirus, poxvirus, vaccinia virus, fowlpox, herpes virus, adeno-associated virus (AAV), alphavirus, lentivirus, lambda phage, lymphocytic choriomeningitis virus, *Listeria* sp, *Salmonella* sp. Said vectors, in particular the amplicons, can comprise a promoter, a Kozak sequence and a polyadenylation signal, in addition to the optimised sequence of SARS-CoV-2.

The present invention can be advantageously used for mammals such as, for example, humans or animals such as, for example, a cat, mink, dog, horse, cow, mouse or rat. Therefore, the products according to the present invention can be used both in human medicine and in veterinary medicine. In particular, the vaccine based on the RBD sequence of SARS-CoV-2 and of variants thereof can be used to vaccinate pets, such as dogs, cats and mink, in particular cats, so that they do not represent a natural reservoir of the virus. At the same time, the vaccine can be used in large-sized animals, such as horses, to generate hyperimmune sera capable of neutralising the virus if administered in patients with the COVID-19 pathology.

It is a further object of the present invention further a kit for the prevention and treatment of the disease caused by the SARS-CoV-2 virus, said kit comprising or consisting of: a) a polynucleotide which encodes for an amino acid sequence, an expression vector comprising said polynucleotide, or a pharmaceutical composition as defined in the claims; and b) a system of administration by electroporation or another device for in vivo gene transduction.

The present invention further provides a method for treating or preventing the SARS-CoV-2 pathology in a patient who needs treatment, the method comprising the administration of a vaccine against the SARS-CoV-2 virus in the form of a vector or plasmid comprising nucleotide sequences encoding for portions or variants of the S protein of the virus, administered for example by means of the muscle electroporation technique.

The number of administrations can be one or two with biweekly, monthly, six-monthly and yearly frequencies.

The present invention can thus be advantageously employed in a method for preventing, treating or slowing SARS-CoV-2 infection in a mammal (such as, for example, a human or an animal, e.g. a cat or mink), which comprises the administration of said combination to a mammal for which such a prevention treatment and slowing is necessary or desirable. As a consequence of the administration, an immune response is then generated against said infection, which is thus prevented, cured or slowed. Following the administration of the combination according to the present invention immune responses of the antibody and cytotoxic T cell type will be generated which exhibit properties of inhibition of the proliferation of the virus and elimination of the cells infected by the virus.

The DNA vaccine according to the present invention can be prepared by means of a process that comprises a) preparing a nucleotide sequence encoding an antigen sequence that consists in or comprises one or more antigens of the SARS-CoV-2 virus; b) cloning the nucleotide sequence in an expression vector or plasmid for expression in cells of a mammal; and c) amplifying the plasmid vector in a suitable bacterial microorganism, and isolating the same from the microorganism or d) amplifying by PCR.

The sequences are extracted from the genome data of SARS-CoV-2 and members of the same family of RNA viruses. The sequences are designed in a laboratory using optimisation of codons for humans. The vaccine sequence is sent to an external provider, who provides for the synthesis and cloning in the pTK1A-TPA or pTK1A vector. The final vector, once sequenced to confirm the correctness of the synthesis, is sent to a GMP certified pharmaceutical manufacturer, who provides for the necessary production of plasmid which, in addition to the treatment of people, will be used to analyse the drug's release.

The vaccine, called "COVID-eVax", which encodes the soluble RBD portion of the spike protein according to the present invention can be prepared in the form of a sterile endotoxin-free solution, for example for parenteral use, to be administered by intramuscular injection, optionally followed by electroporation applied at the injection site. According to one embodiment of the vaccine according to the invention, the vaccine is supplied frozen, appears as a clear, colourless aqueous solution devoid of visible particles, formulated in Dulbecco's phosphate-buffered saline (D-PBS) solution at pH 7.4 and at a concentration of 4 mg/mL. Alternatively, the vaccine can be lyophilised and then resuspended in water for injection. Should a dilution be necessary, the injectable solution of the COVID-eVax vaccine can be diluted with a sterile saline solution (sodium chloride 0.9% w/v) to provide the appropriate concentration of the product. If it is intended for clinical studies, the vaccine can be supplied in sterile type I pyrogen-free transparent 2 mL glass vials with a filling volume of 1 mL, sealed with rubber stoppers and central pull-off aluminium caps with plastic caps.

BRIEF DESCRIPTION OF THE DRAWINGS

The present invention will now be described by an illustrative, but not limitative way, according to a preferred embodiment thereof, with particular reference to the examples and the figures in the appended drawings, wherein:

FIG. 2 shows the alignment of 1977 complete genomes for the genome region 20000-250000 by means of the MAFFT program in SnapGene®. In particular, it shows the amino acid mutations mapped in the RBD region of all European sequences available on the GISAID website as of 12 Apr. 2020. 1977 complete genomes of SARS-CoV-2 were imported in SnapGene® and the regions encoding for the spike protein were selected for a first alignment with the MAFFT software. They were then exported in the FASTA format and realigned with Jalview, which calculates the frequencies of the amino acid changes. The information was graphed with SnapGene®.

FIG. 17 shows the neutralising antibody titre against SARS-CoV-2 infection in VeRo cells, in C57Bl/6 mice. A. Dose-response curve in young mice after a prime/boost vaccination scheme with COVID-eVax; geometric mean in red. B Neutralising titre in young and old animals vaccinated with a fixed dose of COVID-eVax (20 μg).

DETAILED DESCRIPTION

Figure 1:
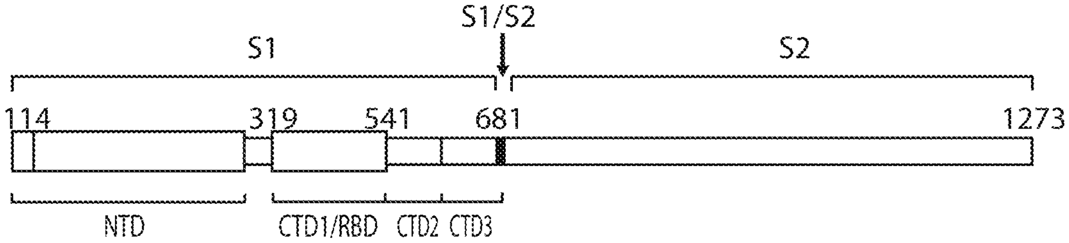
FIG. 1 shows A) Alignment of the amino acid sequence of the SARS-CoV-2 S protein (Query) with the SARS-CoV-1 S protein (Sbjct, ID UNIPROT SARS-CoV-1 P59594) obtained using the BLAST tool, Global Align. B) Schematic representation of the primary sequence of the S protein of SARS-CoV-2 with domains.

Example 1. Molecular Design of the Antigens

Six different constructs were designed (Table 1), including the full-length protein, which were subjected to screening in the vaccination studies.

TABLE 1

| Construct | Residues | Regions/Domains |
|---|---|---|
| Spike-FL | Full Length | Full Length |
| Spike-A | 319-541 | CTD1 (RBD) |
| Spike-B | 14-541 | NTD + CTD1 (RBD) |
| Spike-C | 14-681 | S1 subunit |
| IgK-RBD-Fc | 319-541 | RBD fused to human Fc and to the IgK secretion leader sequence |

The Spike-A construct comprises the RBD only. The Spike B construct comprises the RBD domain and the highly variable domain located at the N-terminal (NTD), whereas the C construct comprises the whole S1 subunit.

The first construct (A) was selected as the main candidate for the recognition of the receptor. It has emerged from structural biology studies that in solution and in the presence of ACE2 the RBD domain maintains a folding that enables it to interact with its partner.

The NTD was inserted into the Spike-B construct; its role, though not entirely clear, could be important in the conformational changes for the recognition of the ACE2 receptor.

The third construct (Spike-C) comprises the whole subunit 1, which is the one most exposed in the extracellular environment and it has been seen that the majority of the antibodies produced by the immune system target precisely this subunit (in SARS-CoV).

Example 2. Comparison Study Between the Sequences of SARS-CoV-2 Known in Europe as of 12 Apr. 2020

The study of the SARS-CoV-2 virus genome provides information that is important for the design of the vaccine. Unlike SARS, which infected a limited number of individuals (about 8000) and was then blocked by social isolation, Covid-19 is a disease that has become pandemic, with over 2×10^6 of confirmed cases and a number of positive serum samples estimated to be at least 100×10^6 (WHO website). This level of spread suggests that the virus can circulate globally and manifest itself in new outbreaks originating in countries entering the cold season in a similar way to the flu virus. Although these are only hypotheses, the vaccine should be aimed against not only the immunogenic regions, but also those that are most conserved in the structure of the S protein. In the previous SARS epidemic it was seen that the neutralising antibodies were mainly directed towards the RBD region. For this purpose, the sequences submitted by European laboratories to the GISAID site as of 12 Apr. 2020 were analysed.

1977 complete genomes were downloaded locally and the genome region 20000-250000 aligned with the program MAFFT in SnapGene®. The sequences were then realigned taking into account only the regions encoding for the S protein. In order to establish the frequency of the mutations at the protein level, the 1977 sequences were translated into proteins and reanalysed with Jalview. The mutations were graphed with SnapGene® (FIG. 2) and are shown below in table 2:

TABLE 2

| Amino acid changes | Number of Events |
|---|---|
| G341V | 1 |
| V367F | 5 |
| A435S | 1 |
| G447K | 1 |
| N448Y | 1 |
| N450Y | 1 |
| Y451F | 1 |
| K458R | 2 |
| T470I | 1 |
| G576S | 1 |
| S477G | 1 |
| P479G | 1 |
| Y489F | 1 |
| Q493F | 1 |
| S494P | 1 |
| Y505Q | 1 |
| Q506Y | 1 |
| Y508H | 1 |
| E516Q | 1 |
| H519P | 1 |
| P521S | 1 |

As may be seen from the figure, there are 21 amino acid residues that show a variation, only two of them with a frequency of two times (K458R) and five times (K356F), for a total of 26 mutations. The frequency of mutations in the RBD region which is the target of our vaccines is thus very low (26/1977=1.3%). As expected, these mutations were not found among the 28 Italian genomes deposited as of 12 April.

Example 3. Design and Construction of the DNA Vectors

The design of a cDNA optimised so as to increase the levels of antigen expression or the optimisation of cDNA consists in replacing the original codons with nucleotide triplets recognised by the tRNAs that are most frequent and efficient in the cells of the organism of interest and was based on the original sequence of spike genes of the Wuhan-Hu-1 strain (GenBank: MN908947). Specific mutations are introduced to silence potential toxic activities or inhibit the formation of secondary structures.

Figure 3:
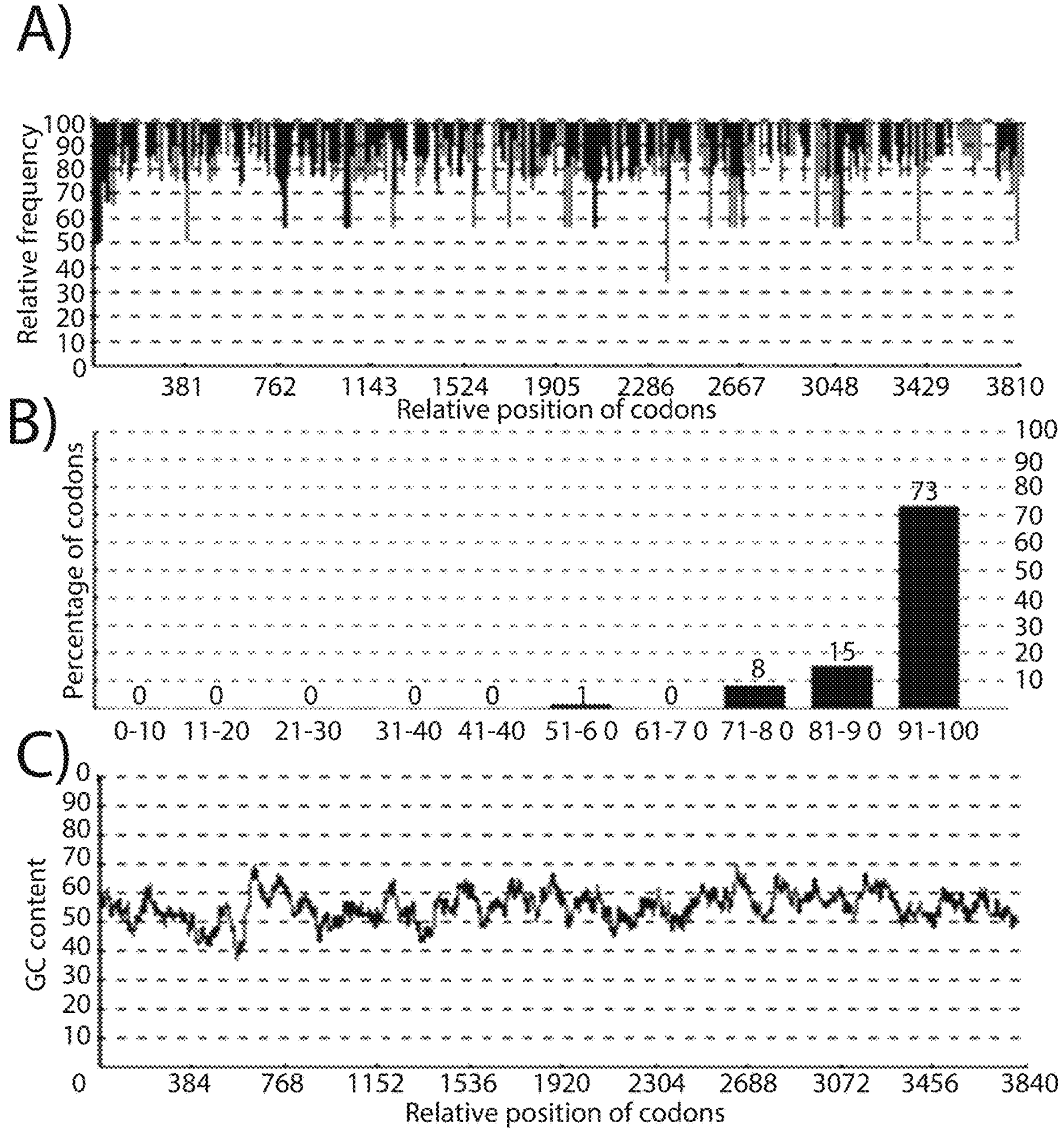
FIG. 3 shows the codon optimisation analysis for a cDNA which codes for the SARS-CoV-2 S protein. A) Adjustment of the codon bias. The distribution of the frequency of use of the codon along the length of the gene sequence. A CAI of 1.0 is considered perfect in the desired organism of expression and a CAI >0.8 is considered good in terms of high level of gene expression. B) Frequency of optimal codons (FOP). The percentage distribution of the codons in the calculated codon quality groups. A value of 100 is set for the codon with the highest usage frequency for a given amino acid in the desired organism of expression. C) Adjustment of the GC content. The ideal percentage interval of the GC content is comprised between 30 and 70%. The % peaks of GC content in a 60 bp window were removed.

The variants of the S protein optimised for codon usage took account of the mixed use of the codon, the GC content, the content of CpG dinucleotides, the secondary structure of the mRNA, the cryptic splice sites, the premature PolyA sites, the internal chi sites and the ribosomal sites, the negative CpG islands, the reason for RNA instability (ARE), sequence repeats (direct repeat, inverted repeat and dyad repeat) and restriction sites that can interfere with cloning. Furthermore, in order to improve the initiation and protein translation, synthetic Kozak and Shine-Dalgarno sequences were inserted into the genes. In order to increase the efficiency of the termination of the translation, two consecutive stop codons were inserted at the end of the cDNA. An example of the analysis of a cDNA that encodes the optimised full-length S protein is shown in FIG. 3. In this case, the native gene uses rare codons in tandem which can reduce the efficiency of translation or even disengage the translation machinery. The tendency toward codon usage in Human was increased by updating the CAI to 0.94. The GC content and unfavourable peaks were optimised to prolong the half-life of the mRNA. The Stem-Loop structures, which influence ribosome binding and mRNA stability, were eliminated. Furthermore, our optimisation process examined and successfully modified the negative cis-acting sites.

The resulting nucleotide sequences are the following, in which RBD is highlighted in bold:

SPIKE A SEQUENCE

SEQ ID NO: 1

AGGGTGCAGCCAACCGAGTCTATCGTGCGCTTTCCTAATATCACAA

ACCTGTGCCCATTTGGCGAGGTGTTCAACGCAACCAGGTTCGCAAG

CGTGTACGCATGGAATAGGAAGCGCATCTCTAACTGCGTGGCCGAC

TATAGCGTGCTGTACAACTCCGCCTCTTTCAGCACCTTTAAGTGCTA

TGGCGTGTCCCCCACAAAGCTGAATGACCTGTGCTTTACCAACGTG

TACGCCGATTCTTTCGTGATCAGGGGCGACGAGGTGCGCCAGATCG

CACCTGGACAGACAGGCAAGATCGCCGACTACAATTATAAGCTGCC

AGACGATTTCACCGGCTGCGTGATCGCCTGGAACAGCAACAATCTG

GATTCCAAAGTGGGCGGCAACTACAATTATCTGTACCGGCTGTTTA

GAAAGAGCAATCTGAAGCCCTTCGAGAGGGACATCTCTACAGAAAT

CTACCAGGCCGGCAGCACCCCTTGCAATGGCGTGGAGGGCTTTAA

CTGTTATTTCCCACTGCAGTCCTACGGCTTCCAGCCCACAAACGGC

GTGGGCTATCAGCCTTACCGCGTGGTGGTGCTGAGCTTTGAGCTGC

TGCACGCACCAGCAACAGTGTGCGGACCCAAGAAGTCCACCAATC

TGGTGAAGAACAAGTGCGTGAACTTC

SPIKE B SEQUENCE

SEQ ID NO: 2

GTGAACCTGACTACTAGAACTCAGCTGCCTCCCGCTTACACCAATTC

CTTCACCCGGGGCGTGTACTATCCTGACAAGGTGTTTAGAAGCTCCG

TGCTGCACTCTACACAGGATCTGTTTCTGCCATTCTTTAGCAACGTGA

CCTGGTTCCACGCCATCCACGTGAGCGGCACCAATGGCACAAAGCG

GTTCGACAATCCCGTGCTGCCTTTTAACGATGGCGTGTACTTCGCCT

CTACCGAGAAGAGCAACATCATCAGAGGCTGGATCTTTGGCACCACA

CTGGACTCCAAGACACAGTCTCTGCTGATCGTGAACAATGCCACCAA

CGTGGTCATCAAGGTGTGCGAGTTCCAGTTTTGTAATGATCCCTTCCT

GGGCGTGTACTATCACAAGAACAATAAGAGCTGGATGGAGTCCGAGT

TTAGAGTGTATTCTAGCGCCAACAATTGCACATTTGAGTACGTGTCCC

AGCCTTTCCTGATGGACCTGGAGGGCAAGCAGGGCAATTTCAAGAAC

CTGAGGGAGTTCGTGTTTAAGAATATCGATGGCTACTTCAAAATCTAC

TCTAAGCACACCCCCATCAACCTGGTGCGCGACCTGCCTCAGGGCTT

CAGCGCCCTGGAGCCACTGGTGGATCTGCCTATCGGCATCAACATCA

CCCGGTTTCAGACACTGCTGGCCCTGCACAGAAGCTACCTGACACCC

GGCGACTCCTCTAGCGGATGGACCGCAGGAGCAGCAGCCTACTATG

TGGGCTATCTGCAGCCTAGGACCTTCCTGCTGAAGTACAACGAGAAT

GGCACCATCACAGACGCCGTGGATTGCGCCCTGGATCCTCTGAGCG

AGACAAAGTGTACACTGAAGTCCTTTACCGTGGAGAAGGGCATCTAT

CAGACATCCAATTTCAGGGTGCAGCCAACCGAGTCTATCGTGCGCTT

TCCTAATATCACAAACCTGTGCCCATTTGGCGAGGTGTTCAACGCA

ACCAGGTTCGCAAGCGTGTACGCATGGAATAGGAAGCGCATCTCTA

-continued

ACTGCGTGGCCGACTATAGCGTGCTGTACAACTCCGCCTCTTTCAG

CACCTTTAAGTGCTATGGCGTGTCCCCCACAAAGCTGAATGACCTG

TGCTTTACCAACGTGTACGCCGATTCTTTCGTGATCAGGGGCGACG

AGGTGCGCCAGATCGCACCTGGACAGACAGGCAAGATCGCCGACT

ACAATTATAAGCTGCCAGACGATTTCACCGGCTGCGTGATCGCCTG

GAACAGCAACAATCTGGATTCCAAAGTGGGCGGCAACTACAATTAT

CTGTACCGGCTGTTTAGAAAGAGCAATCTGAAGCCCTTCGAGAGGG

ACATCTCTACAGAAATCTACCAGGCCGGCAGCACCCCTTGCAATGG

CGTGGAGGGCTTTAACTGTTATTTCCCACTGCAGTCCTACGGCTTCC

AGCCCACAAACGGCGTGGGCTATCAGCCTTACCGCGTGGTGGTGCT

GAGCTTTGAGCTGCTGCACGCACCAGCAACAGTGTGCGGACCCAA

GAAGTCCACCAATCTGGTGAAGAACAAGTGCGTGAACTTC

SPIKE C SEQUENCE

SEQ ID NO: 3

GTGAACCTGACTACTAGAACTCAGCTGCCTCCCGCTTACACCAATTC

CTTCACCCGGGGCGTGTACTATCCTGACAAGGTGTTTAGAAGCTCCG

TGCTGCACTCTACACAGGATCTGTTTCTGCCATTCTTTAGCAACGTGA

CCTGGTTCCACGCCATCCACGTGAGCGGCACCAATGGCACAAAGCG

GTTCGACAATCCCGTGCTGCCTTTTAACGATGGCGTGTACTTCGCCT

CTACCGAGAAGAGCAACATCATCAGAGGCTGGATCTTTGGCACCACA

CTGGACTCCAAGACACAGTCTCTGCTGATCGTGAACAATGCCACCAA

CGTGGTCATCAAGGTGTGCGAGTTCCAGTTTTGTAATGATCCCTTCCT

GGGCGTGTACTATCACAAGAACAATAAGAGCTGGATGGAGTCCGAGT

TTAGAGTGTATTCTAGCGCCAACAATTGCACATTTGAGTACGTGTCCC

AGCCTTTCCTGATGGACCTGGAGGGCAAGCAGGGCAATTTCAAGAAC

CTGAGGGAGTTCGTGTTTAAGAATATCGATGGCTACTTCAAAATCTAC

TCTAAGCACACCCCCATCAACCTGGTGCGCGACCTGCCTCAGGGCTT

CAGCGCCCTGGAGCCACTGGTGGATCTGCCTATCGGCATCAACATCA

CCCGGTTTCAGACACTGCTGGCCCTGCACAGAAGCTACCTGACACCC

GGCGACTCCTCTAGCGGATGGACCGCAGGAGCAGCAGCCTACTATG

TGGGCTATCTGCAGCCTAGGACCTTCCTGCTGAAGTACAACGAGAAT

GGCACCATCACAGACGCCGTGGATTGCGCCCTGGATCCTCTGAGCG

AGACAAAGTGTACACTGAAGTCCTTTACCGTGGAGAAGGGCATCTAT

CAGACATCCAATTTCAGGGTGCAGCCAACCGAGTCTATCGTGCGCTT

TCCTAATATCACAAACCTGTGCCCATTTGGCGAGGTGTTCAACGCA

ACCAGGTTCGCAAGCGTGTACGCATGGAATAGGAAGCGCATCTCTA

ACTGCGTGGCCGACTATAGCGTGCTGTACAACTCCGCCTCTTTCAG

CACCTTTAAGTGCTATGGCGTGTCCCCCACAAAGCTGAATGACCTG

TGCTTTACCAACGTGTACGCCGATTCTTTCGTGATCAGGGGCGACG

AGGTGCGCCAGATCGCACCTGGACAGACAGGCAAGATCGCCGACT

ACAATTATAAGCTGCCAGACGATTTCACCGGCTGCGTGATCGCCTG

-continued

GAACAGCAACAATCTGGATTCCAAAGTGGGCGGCAACTACAATTAT
CTGTACCGGCTGTTTAGAAAGAGCAATCTGAAGCCCTTCGAGAGGG
ACATCTCTACAGAAATCTACCAGGCCGGCAGCACCCCTTGCAATGG
CGTGGAGGGCTTTAACTGTTATTTCCCACTGCAGTCCTACGGCTTCC
AGCCCACAAACGGCGTGGGCTATCAGCCTTACCGCGTGGTGGTGCT
GAGCTTTGAGCTGCTGCACGCACCAGCAACAGTGTGCGGACCCAA
GAAGTCCACCAATCTGGTGAAGAACAAGTGCGTGAACTTCAACTTC
AACGGCCTGACCGGAACAGGCGTGCTGACCGAGTCCAACAAGAAGT
TCCTGCCATTTCAGCAGTTCGGCAGGGACATCGCAGATACCACAGAC
GCCGTGCGCGACCCACAGACCCTGGAGATCCTGGATATCACACCCT
GCTCTTTCGGCGGCGTGAGCGTGATCACACCAGGAACCAATACAAG
CAACCAGGTGGCCGTGCTGTATCAGGACGTGAATTGTACCGAGGTG
CCTGTGGCCATCCACGCCGATCAGCTGACCCCAACATGGCGGGTGT
ACAGCACCGGCTCCAACGTGTTCCAGACAAGAGCAGGATGTCTGATC
GGAGCAGAGCACGTGAACAATTCCTATGAGTGCGACATCCCAATCGG
CGCCGGCATCTGTGCCTCTTACCAGACCCAGACAAACTCTCCA

SPIKE IgK-RBD-Fc SEQUENCE

SEQ ID NO: 4

ATGGAGACAGACACACTCCTGCTATGGGTACTGCTGCTCTGGGTTCC
AGGATCCACAGGAAGGGTGCAGCCAACCGAGTCTATCGTGCGCTTT
CCTAATATCACAAACCTGTGCCCATTTGGCGAGGTGTTCAACGCAA
CCAGGTTCGCAAGCGTGTACGCATGGAATAGGAAGCGCATCTCTAA
CTGCGTGGCCGACTATAGCGTGCTGTACAACTCCGCCTCTTTCAGC
ACCTTTAAGTGCTATGGCGTGTCCCCCACAAAGCTGAATGACCTGT
GCTTTACCAACGTGTACGCCGATTCTTTCGTGATCAGGGGCGACGA
GGTGCGCCAGATCGCACCTGGACAGACAGGCAAGATCGCCGACTA
CAATTATAAGCTGCCAGACGATTTCACCGGCTGCGTGATCGCCTGG
AACAGCAACAATCTGGATTCCAAAGTGGGCGGCAACTACAATTATC
TGTACCGGCTGTTTAGAAAGAGCAATCTGAAGCCCTTCGAGAGGGA
CATCTCTACAGAAATCTACCAGGCCGGCAGCACCCCTTGCAATGGC
GTGGAGGGCTTTAACTGTTATTTCCCACTGCAGTCCTACGGCTTCCA
GCCCACAAACGGCGTGGGCTATCAGCCTTACCGCGTGGTGGTGCT
GAGCTTTGAGCTGCTGCACGCACCAGCAACAGTGTGCGGACCCAA
GAAGTCCACCAATCTGGTGAAGAACAAGTGCGTGAACTTCGTCGAC
AAAACTCACACATGCCCACCGTGCCCAGCACCTGAACTCCTGGGGG
GACCGTCAGTCTTCCTCTTCCCCCCAAAACCCAAGGACACCCTCATG
ATCTCCCGGACCCCTGAGGTCACATGCGTGGTGGTGGACGTGAGCC
ACGAAGACCCTGAGGTCAAGTTCAACTGGTACGTGGACGGCGTGGA
GGTGCATAATGCCAAGACAAAGCCGCGGGAGGAGCAGTACAACAGC
ACGTACCGTGTGGTCAGCGTCCTCACCGTCCTGCACCAGGACTGGC
TGAATGGCAAGGAGTACAAGTGCAAGGTCTCCAACAAAGCCCTCCCA
GCCCCCATCGAGAAAACCATCTCCAAAGCCAAAGGGCAGCCCCGAG

-continued

AACCACAGGTGTACACCCTGCCCCCATCCCGGGAGGAGATGACCAA
GAACCAGGTCAGCCTGACCTGCCTGGTCAAAGGCTTCTATCCCAGCG
ACATCGCCGTGGAGTGGGAGAGCAATGGGCAGCCGGAGAACAACTA
CAAGACCACGCCTCCCGTGCTGGACTCCGACGGCTCCTTCTTCCTCT
ACAGCAAGCTCACCGTGGACAAGAGCAGGTGGCAGCAGGGGAACGT
CTTCTCATGCTCCGTGATGCATGAGGCTCTGCACAACCACTACACGC
AGAAGAGCCTCTCCCTGTCTCCGGGTAAA

Full-length SPIKE SEQUENCE

SEQ ID NO: 5

GATCTGCCACCATGTTTGTCTTCCTGGTCCTGCTGCCCCTGGTCTCC
TCTCAGTGCGTGAACCTGACTACTAGAACTCAGCTGCCTCCCGCTTA
CACCAATTCCTTCACCCGGGGCGTGTACTATCCTGACAAGGTGTTTA
GAAGCTCCGTGCTGCACTCTACACAGGATCTGTTTCTGCCATTCTTTA
GCAACGTGACCTGGTTCCACGCCATCCACGTGAGCGGCACCAATGG
CACAAAGCGGTTCGACAATCCCGTGCTGCCTTTTAACGATGGCGTGT
ACTTCGCCTCTACCGAGAAGAGCAACATCATCAGAGGCTGGATCTTT
GGCACCACACTGGACTCCAAGACACAGTCTCTGCTGATCGTGAACAA
TGCCACCAACGTGGTCATCAAGGTGTGCGAGTTCCAGTTTTGTAATG
ATCCCTTCCTGGGCGTGTACTATCACAAGAACAATAAGAGCTGGATG
GAGTCCGAGTTTAGAGTGTATTCTAGCGCCAACAATTGCACATTTGAG
TACGTGTCCCAGCCTTTCCTGATGGACCTGGAGGGCAAGCAGGGCA
ATTTCAAGAACCTGAGGGAGTTCGTGTTTAAGAATATCGATGGCTACT
TCAAAATCTACTCTAAGCACACCCCCATCAACCTGGTGCGCGACCTG
CCTCAGGGCTTCAGCGCCCTGGAGCCACTGGTGGATCTGCCTATCG
GCATCAACATCACCCGGTTTCAGACACTGCTGGCCCTGCACAGAAGC
TACCTGACACCCGGCGACTCCTCTAGCGGATGGACCGCAGGAGCAG
CAGCCTACTATGTGGGCTATCTGCAGCCTAGGACCTTCCTGCTGAAG
TACAACGAGAATGGCACCATCACAGACGCCGTGGATTGCGCCCTGG
ATCCTCTGAGCGAGACAAAGTGTACACTGAAGTCCTTTACCGTGGAG
AAGGGCATCTATCAGACATCCAATTTCAGGGTGCAGCCAACCGAGTC
TATCGTGCGCTTTCCTAATATCACAAACCTGTGCCCATTTGGCGAGG
TGTTCAACGCAACCAGGTTCGCAAGCGTGTACGCATGGAATAGGAA
GCGCATCTCTAACTGCGTGGCCGACTATAGCGTGCTGTACAACTCC
GCCTCTTTCAGCACCTTTAAGTGCTATGGCGTGTCCCCCACAAAGCT
GAATGACCTGTGCTTTACCAACGTGTACGCCGATTCTTTCGTGATCA
GGGGCGACGAGGTGCGCCAGATCGCACCTGGACAGACAGGCAAG
ATCGCCGACTACAATTATAAGCTGCCAGACGATTTCACCGGCTGCG
TGATCGCCTGGAACAGCAACAATCTGGATTCCAAAGTGGGCGGCAA
CTACAATTATCTGTACCGGCTGTTTAGAAAGAGCAATCTGAAGCCCT
TCGAGAGGGACATCTCTACAGAAATCTACCAGGCCGGCAGCACCC
CTTGCAATGGCGTGGAGGGCTTTAACTGTTATTTCCCACTGCAGTCC

-continued

TACGGCTTCCAGCCCACAAACGGCGTGGGCTATCAGCCTTACCGCG

TGGTGGTGCTGAGCTTTGAGCTGCTGCACGCACCAGCAACAGTGTG

CGGACCCAAGAAGTCCACCAATCTGGTGAAGAACAAGTGCGTGAA

CTTCAACTTCAACGGCCTGACCGGAACAGGCGTGCTGACCGAGTCC

AACAAGAAGTTCCTGCCATTTCAGCAGTTCGGCAGGGACATCGCAGA

TACCACAGACGCCGTGCGCGACCCACAGACCCTGGAGATCCTGGAT

ATCACACCCTGCTCTTTCGGCGGCGTGAGCGTGATCACACCAGGAAC

CAATACAAGCAACCAGGTGGCCGTGCTGTATCAGGACGTGAATTGTA

CCGAGGTGCCTGTGGCCATCCACGCCGATCAGCTGACCCCAACATG

GCGGGTGTACAGCACCGGCTCCAACGTGTTCCAGACAAGAGCAGGA

TGTCTGATCGGAGCAGAGCACGTGAACAATTCCTATGAGTGCGACAT

CCCAATCGGCGCCGGCATCTGTGCCTCTTACCAGACCCAGACAAACT

CTCCAAGGAGAGCACGGAGCGTGGCATCCCAGTCTATCATCGCCTAT

ACCATGTCCCTGGGCGCCGAGAATTCTGTGGCCTACTCTAACAATAG

CATCGCCATCCCAACCAACTTCACAATCTCTGTGACCACAGAGATCCT

GCCCGTGTCCATGACCAAGACATCTGTGGACTGCACAATGTATATCT

GTGGCGATTCTACCGAGTGCAGCAACCTGCTGCTGCAGTACGGCAG

CTTTTGTACCCAGCTGAATAGAGCCCTGACAGGCATCGCCGTGGAGC

AGGATAAGAACACACAGGAGGTGTTCGCCCAGGTGAAGCAAATCTAC

AAGACCCCCCCTATCAAGGACTTTGGCGGCTTCAATTTTTCCCAGATC

CTGCCTGATCCATCCAAGCCTTCTAAGCGGAGCTTTATCGAGGACCT

GCTGTTCAACAAGGTGACCCTGGCCGATGCCGGCTTCATCAAGCAGT

ATGGCGATTGCCTGGGCGACATCGCAGCACGGGACCTGATCTGTGC

CCAGAAGTTTAATGGCCTGACCGTGCTGCCACCCCTGCTGACAGATG

AGATGATCGCACAGTACACAAGCGCCCTGCTGGCAGGAACCATCACA

TCCGGATGGACCTTCGGCGCAGGAGCCGCCCTGCAGATCCCCTTTG

CCATGCAGATGGCCTATAGGTTCAACGGCATCGGCGTGACCCAGAAT

GTGCTGTACGAGAACCAGAAGCTGATCGCCAATCAGTTTAACTCCGC

CATCGGCAAGATCCAGGACAGCCTGTCCTCTACAGCCTCCGCCCTG

GGCAAGCTGCAGGATGTGGTGAATCAGAACGCCCAGGCCCTGAATA

CCCTGGTGAAGCAGCTGAGCTCCAACTTCGGCGCCATCTCTAGCGT

GCTGAATGATATCCTGAGCCGGCTGGACAAGGTGGAGGCAGAGGTG

CAGATCGACCGGCTGATCACAGGCAGACTGCAGTCTCTGCAGACCTA

TGTGACACAGCAGCTGATCAGGGCAGCAGAGATCAGGGCAAGCGCC

AATCTGGCAGCAACCAAGATGTCCGAGTGCGTGCTGGGCCAGTCTAA

GAGAGTGGACTTTTGTGGCAAGGGCTATCACCTGATGTCCTTCCCTC

AGTCTGCCCCACACGGCGTGGTGTTTCTGCACGTGACCTACGTGCC

CGCCCAGGAGAAGAACTTCACCACAGCCCCTGCCATCTGCCACGAT

GGCAAGGCCCACTTTCCAAGGGAGGGCGTGTTCGTGTCCAACGGCA

CCCACTGGTTTGTGACACAGCGCAATTTCTACGAGCCCCAGATCATC

ACCACAGACAATACCTTCGTGAGCGGCAACTGTGACGTGGTCATCGG

-continued

CATCGTGAACAATACCGTGTATGATCCACTGCAGCCCGAGCTGGACA

GCTTTAAGGAGGAGCTGGATAAGTACTTCAAGAATCACACCTCCCCT

GACGTGGATCTGGGCGACATCAGCGGCATCAATGCCTCCGTGGTGA

ACATCCAGAAGGAGATCGACCGCCTGAACGAGGTGGCCAAGAATCT

GAACGAGAGCCTGATCGATCTGCAGGAGCTGGGCAAGTATGAGCAG

TACATCAAGTGGCCATGGTACATCTGGCTGGGCTTCATCGCCGGCCT

GATCGCCATCGTGATGGTGACCATCATGCTGTGCTGTATGACATCCT

GCTGTTCTTGCCTGAAGGGCTGCTGTAGCTGCGGCTCCTGTTGTAAG

TTTGATGAAGACGATTCCGAGCCTGTCCTGAAGGGCGTGAAGCTGCA

CTATACCTCTAGATAATGAG

The polynucleotide sequences shown above encode for the following protein sequences:

SPIKE A SEQUENCE

SEQ ID NO: 7

RVQPTESIVRFPNITNLCPFGEVFNATRFASVYAWNRKRISNCVADYSV

LYNSASFSTFKCYGVSPTKLNDLCFTNVYADSFVIRGDEVRQIAPGQTG

KIADYNYKLPDDFTGCVIAWNSNNLDSKVGGNYNYLYRLFRKSNLKPF

ERDISTEIYQAGSTPCNGVEGFNCYFPLQSYGFQPTNGVGYQPYRVVVL

SFELLHAPATVCGPKKSTNLVKNKCVNF

SPIKE B SEQUENCE

SEQ ID NO: 8

VNLTTRTQLPPAYTNSFTRGVYYPDKVFRSSVLHSTQDLFLPFFSNVTW

FHAIHVSGTNGTKRFDNPVLPFNDGVYFASTEKSNIIRGWIFGTTLDSKT

QSLLIVNNATNVVIKVCEFQFCNDPFLGVYYHKNNKSWMESEFRVYSSA

NNCTFEYVSQPFLMDLEGKQGNFKNLREFVFKNIDGYFKIYSKHTPINLV

RDLPQGFSALEPLVDLPIGINITRFQTLLALHRSYLTPGDSSSGWTAGAA

AYYVGYLQPRTFLLKYNENGTITDAVDCALDPLSETKCTLKSFTVEKGIY

QTSNFRVQPTESIVRFPNITNLCPFGEVFNATRFASVYAWNRKRISNCV

ADYSVLYNSASFSTFKCYGVSPTKLNDLCFTNVYADSFVIRGDEVRQIA

PGQTGKIADYNYKLPDDFTGCVIAWNSNNLDSKVGGNYNYLYRLFRKS

NLKPFERDISTEIYQAGSTPCNGVEGFNCYFPLQSYGFQPTNGVGYQPY

RVVVLSFELLHAPATVCGPKKSTNLVKNKCVNF

SPIKE C SEQUENCE

SEQ ID NO: 9

VNLTTRTQLPPAYTNSFTRGVYYPDKVFRSSVLHSTQDLFLPFFSNVTW

FHAIHVSGTNGTKRFDNPVLPFNDGVYFASTEKSNIIRGWIFGTTLDSKT

QSLLIVNNATNVVIKVCEFQFCNDPFLGVYYHKNNKSWMESEFRVYSSA

NNCTFEYVSQPFLMDLEGKQGNFKNLREFVFKNIDGYFKIYSKHTPINLV

RDLPQGFSALEPLVDLPIGINITRFQTLLALHRSYLTPGDSSSGWTAGAA

AYYVGYLQPRTFLLKYNENGTITDAVDCALDPLSETKCTLKSFTVEKGIY

QTSNFRVQPTESIVRFPNITNLCPFGEVFNATRFASVYAWNRKRISNCV

ADYSVLYNSASFSTFKCYGVSPTKLNDLCFTNVYADSFVIRGDEVRQIA

PGQTGKIADYNYKLPDDFTGCVIAWNSNNLDSKVGGNYNYLYRLFRKS

-continued

NLKPFERDISTEIYQAGSTPCNGVEGFNCYFPLQSYGFQPTNGVGYQPY

RVVVLSFELLHAPATVCGPKKSTNLVKNKCVNFNFNGLTGTGVLTESNK

KFLPFQQFGRDIADTTDAVRDPQTLEILDITPCSFGGVSVITPGTNTSNQ

VAVLYQDVNCTEVPVAIHADQLTPTWRVYSTGSNVFQTRAGCLIGAEHV

NNSYECDIPIGAGICASYQTQTNSP

SPIKE IgK-RBD-Fc SEQUENCE

SEQ ID NO: 10

METDTLLLWVLLLWVPGSTGRVQPTESIVRFPNITNLCPFGEVFNATRFA

SVYAWNRKRISNCVADYSVLYNSASFSTFKCYGVSPTKLNDLCFTNVY

ADSFVIRGDEVRQIAPGQTGKIADYNYKLPDDFTGCVIAWNSNNLDSKV

GGNYNYLYRLFRKSNLKPFERDISTEIYQAGSTPCNGVEGFNCYFPLQS

YGFQPTNGVGYQPYRVVVLSFELLHAPATVCGPKKSTNLVKNKCVNFV

DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCL

VKGFYPSDIAVEWESNGQPENNYKTTPPVLDSDGSFFLYSKLTVDKSRW

QQGNVFSCSVMHEALHNHYTQKSLSLSPGK

Full-length SPIKE SEQUENCE

SEQ ID NO: 11

MFVFLVLLPLVSSQCVNLTTRTQLPPAYTNSFTRGVYYPDKVFRSSVLHS

TQDLFLPFFSNVTWFHAIHVSGTNGTKRFDNPVLPFNDGVYFASTEKSNI

IRGWIFGTTLDSKTQSLLIVNNATNVVIKVCEFQFCNDPFLGVYYHKNNK

SWMESEFRVYSSANNCTFEYVSQPFLMDLEGKQGNFKNLREFVFKNIDGY

FKIYSKHTPINLVRDLPQGFSALEPLVDLPIGINITRFQTLLALHRSYLT

PGDSSSGWTAGAAAYYVGYLQPRTFLLKYNENGTITDAVDCALDPLSETK

CTLKSFTVEKGIYQTSNFRVQPTESIVRFPNITNLCPFGEVFNATRFASV

YAWNRKRISNCVADYSVLYNSASFSTFKCYGVSPTKLNDLCFTNVYADSF

VIRGDEVRQIAPGQTGKIADYNYKLPDDFTGCVIAWNSNNLDSKVGGNY

NYLYRLFRKSNLKPFERDISTEIYQAGSTPCNGVEGFNCYFPLQSYGFQ

PTNGVGYQPYRVVVLSFELLHAPATVCGPKKSTNLVKNKCVNFNFNGL

TGTGVLTESNKKFLPFQQFGRDIADTTDAVRDPQTLEILDITPCSFGGVS

VITPGTNTSNQVAVLYQDVNCTEVPVAIHADQLTPTWRVYSTGSNVFQTR

AGCLIGAEHVNNSYECDIPIGAGICASYQTQTNSPRRARSVASQSIIAYT

MSLGAENSVAYSNNSIAIPTNFTISVTTEILPVSMTKTSVDCTMYICGDS

TECSNLLLQYGSFCTQLNRALTGIAVEQDKNTQEVFAQVKQIYKTPPIKD

FGGFNFSQILPDPSKPSKRSFIEDLLFNKVTLADAGFIKQYGDCLGDIAA

RDLICAQKFNGLTVLPPLLTDEMIAQYTSALLAGTITSGWTFGAGAALQI

PFAMQMAYRFNGIGVTQNVLYENQKLIANQFNSAIGKIQDSLSSTASALG

KLQDVVNQNAQALNTLVKQLSSNFGAISSVLNDILSRLDKVEAEVQIDRL

ITGRLQSLQTYVTQQLIRAAEIRASANLAATKMSECVLGQSKRVDFCGKG

YHLMSFPQSAPHGVVFLHVTYVPAQEKNFTTAPAICHDGKAHFPREGVFV

SNGTHWFVTQRNFYEPQIITTDNTFVSGNCDVVIGIVNNTVYDPLQPELD

-continued

SFKEELDKYFKNHTSPDVDLGDISGINASVVNIQKEIDRLNEVAKNLNES

LIDLQELGKYEQYIKWPWYIWLGFIAGLIAIVMVTIMLCCMTSCCSCLKG

CCSCGSCCKFDEDDSEPVLKGVKLHYTSR

The sequences were then incorporated into the expression vector pTK1A-TPA (Spike A, B, C) or pTK1A (Full-length Spike or IgK-RBD-Fc). Both vectors have the promoter and intron A of human cytomegalovirus (CMV), a polylinker site for the cloning and bovine growth hormone (bGH) as polyA for the termination of the transcription. The pTK1A-TPA vector, compared to pTK1A, also comprises the nucleotide sequence of the tissue plasminogen activator (tPA) secretion leader sequence SEQ ID NO:16 ATGGATGCAATGAAGAGAGGGCTCTGCTGTGTGCTGCTGCTGTGTGGAGCAGTCTTCGTTTCGCCCAGC which encodes for the amino acid sequence SEQ ID NO:17 MDAMKRGLCCVLLLCGAVFVSPS.

Example 4. Treatment of Mice with the Vaccine Against SARS-CoV-2

With reference to Article 170bis of the Italian Industrial Property Code, it is hereby declared that the studies on genetically modified organisms described below were conducted within a facility with containment level BSL2, with notification ID RM/IC/Imp2/04/001, Takis s.r.l. authorised on Sep. 4, 2015.

In order to obtain a B and T cell response against the antigens of interest identified above (Spike A, Spike B, Spike C, Full-Length Spike and IgK-RBD-Fc), a genetic vaccination based on the electroporation of DNA into the skeletal muscles was adopted. This technology enables the expression of a sequence of different antigens suitably engineered for the purpose of presenting them to the immune system and inducing an effector response against the virus. The plasmid vector used, pTK1A or pTK1-TPA, encodes for the S protein constructs expressed, whose amino acid sequences were described previously.

The vaccination protocol consisted in an injection in both quadricep muscles of female BALB/c or C57/B6 mice aged 6-7 weeks (Envigo, the Netherlands); the DNA was formulated in phosphate-buffered saline (PBS) at a concentration of 0.2 mg/ml. DNA-EP was performed with an electroporator of the IGEA Cliniporator type, using a needle electrode (electrode A-15-4B). For the DNA-EP in the muscle, the following electric conditions were applied:

EGT (Electro-Gene-Transfer) Conditions: low voltage, 8 pulses of 20 msec, each at 110V, 8 Hz, with an interval of 120 msec between each of them.

ECT (Electrochemotherapy) Conditions: high voltage, 8 pulses of 100 sec, each at 400V, 5000 Hz.

The EGT and ECT conditions were used to compare the level of gene expression and immunogenicity, considering an immediate application of the Cliniporator, which is already available throughout Europe in the ECT mode, whereas it needs to be adapted in order to convert it into the EGT mode.

As a gene expression control, use was made of a plasmid that expresses luciferase (pGL3-Luc, Promega).

As a negative control group, mice were injected with DNA but not electroporated.

At 72 hours after the treatment, as shown in the graph and in the instrument image, the results showed an almost total absence of expression when the DNA expressing luciferase was not electroporated (1.5×10^5 p/s), a mean expression of 1.4×10^7 p/s when the ECT conditions were used and an expression that was 4000 times greater when, finally, the EGT conditions were used (6×10^8 p/s).

Figure 4:
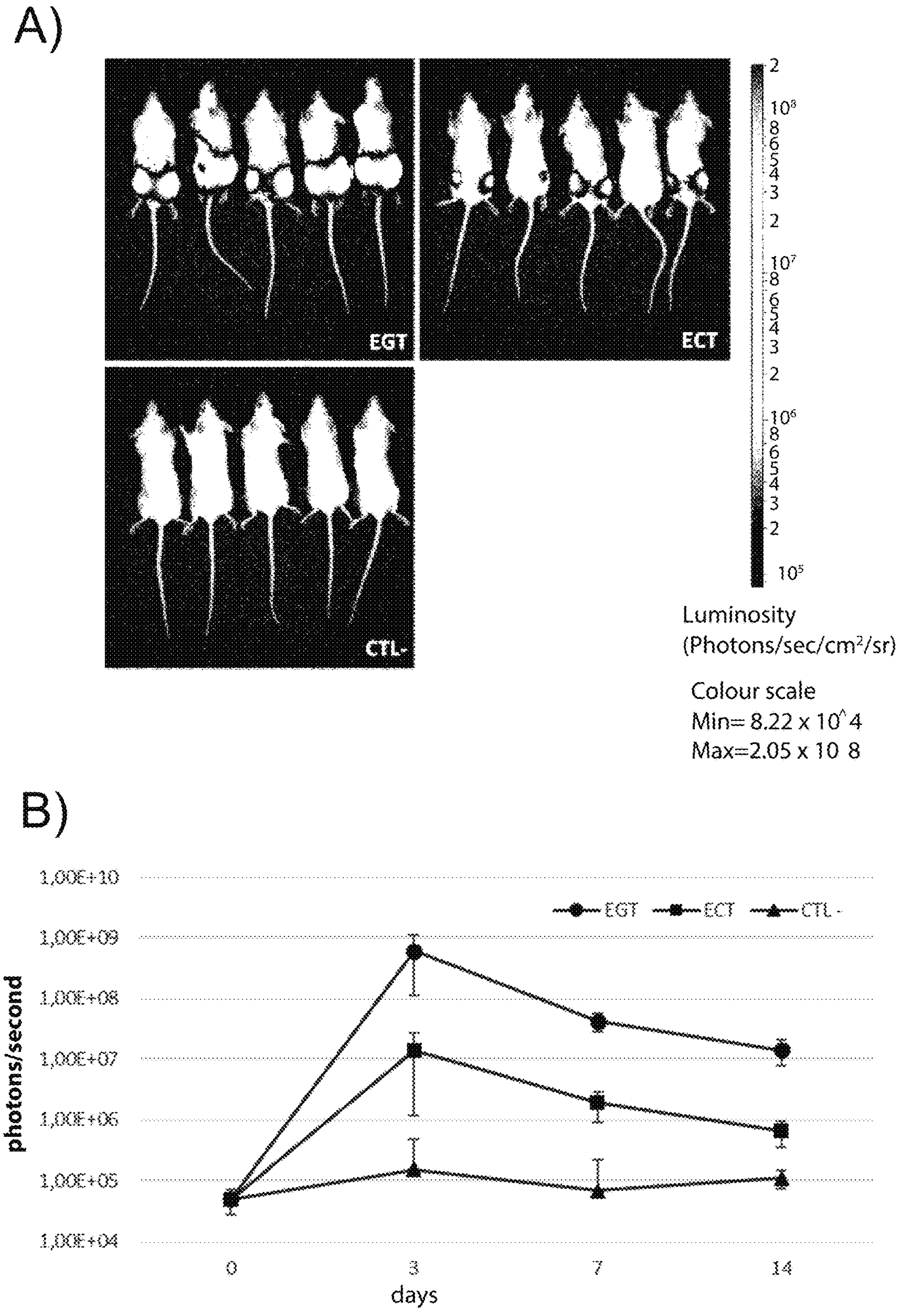
FIG. 4 shows the expression of luciferase in the muscle of mice injected with pGL3-Luc plasmid (Promega) using different electrical conditions (EGT, ECT, only DNA injection). In particular, the figure shows the expression of luciferase in mice treated under the following conditions: A) expression at 72 hours after EGT conditions, ECT conditions and no electroporation. B) kinetics of luciferase expression over time until day 14.

In the instrument (IVIS 200) image (see FIG. 4), there is an evident difference in the bioluminescence signal in the 3 groups of animals in which the plasmid expressing luciferase was injected: the negative control without electroporation (CTL−), electroporation with ECT conditions and electroporation with EGT conditions.

Example 5. Production of RBD-Fc and RBD-6His Proteins

The RBD-Fc and RBD-6×His proteins were produced by transient transfection of high-density Expi293F cells with the cationic lipid-based transfection reagent ExpiFectamine 293 (Thermo Fisher) according to the manufacturer's instructions. The supernatant containing the proteins was collected after a week and subjected to clarification by centrifugation and filtration for the subsequent purification steps. The RBD-Fc protein was purified by affinity chromatography using the AktaPure system with a protein column A (TOYOSCREEN AF-RPROTEIN A HC-650F; Tosoh Bioscience). Briefly, the column was equilibrated with binding buffer (Phosphate Buffer 0.1M pH8) and loaded with the supernatant diluted 1:1 with the same buffer. After washing of the column, the protein was recovered by acid elution in 0.1M pH3 citrate buffer, neutralised in Tris-HCl pH9 and subjected to dialysis in PBS1× with the slide-A-lyzer (Thermo Fisher) according to the indications in the product datasheet.

Figure 5:
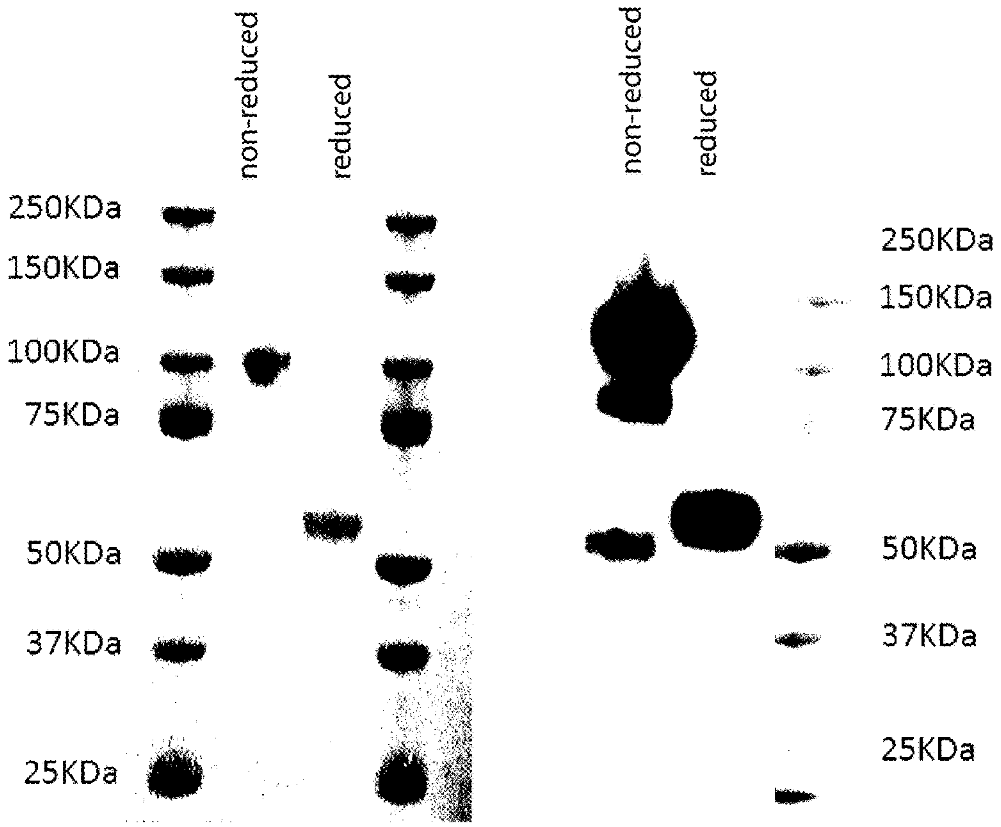
FIG. 5 and FIG. 6 show the IgK-RBD-Fc protein and purified RBD-6His, in particular the analysis of structural integrity by western blot and SDS-PAGE analysis of the RBD-Fc (upper panel) and RBD-6×His (lower panel) proteins under both denaturing and non-denaturing conditions.
Figure 6:
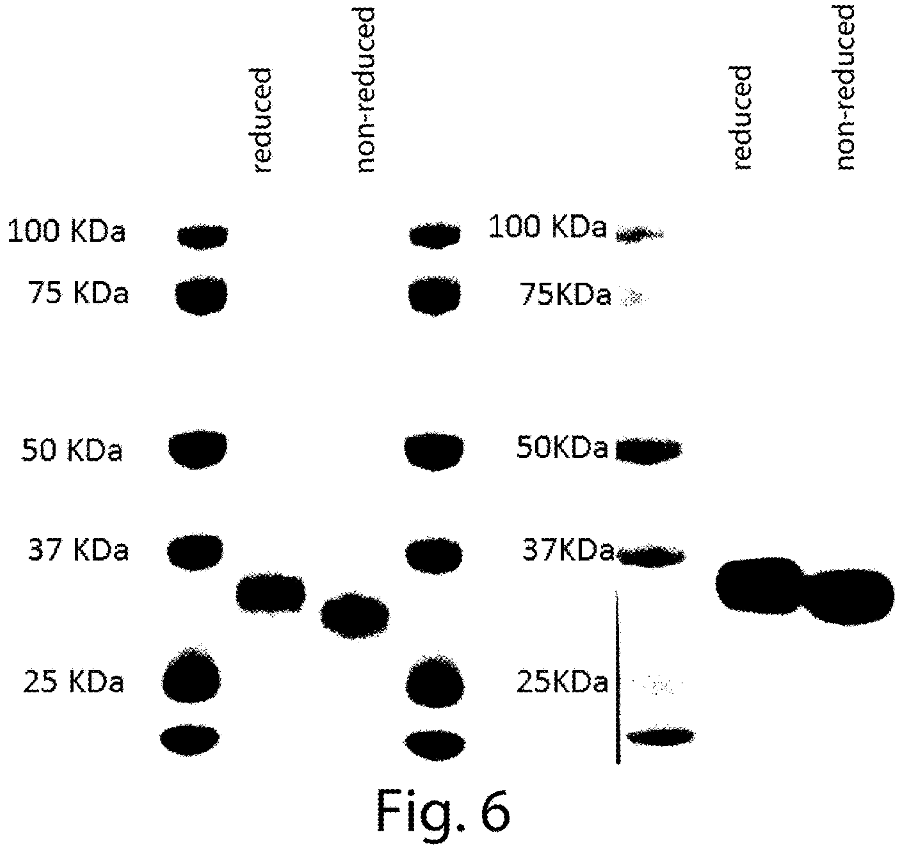

The RBD-6×HIS protein was purified by affinity chromatography of His Tag residues for immobilised metals using the AktaPure system with HisPur™ Ni-NTA Chromatography Cartridges (Thermo Fisher) according to the manufacturer's instructions. Briefly, the column was equilibrated in 5 mM PBS1×/Imidazole and loaded with the supernatant diluted 1:1 with the same buffer. After washing, the protein was eluted with 0.3M PBS1×/Imidazole, pH 7.4, and dialysed in PBS1× with the slide-A-lyzer (Thermo Fisher) according to the indications in the product datasheet. Once they had been recovered from dialysis the RBD-Fc and RBD-6×His proteins were quantified by spectrophotometry with absorbance at 280 nm (FIGS. 5 and 6).

The purity of the proteins was evaluated by SDS-PAGE and western blot analysis, conducted both under reduced and non-reduced conditions and using the standard methods.

Example 6. Measurement of the Titre of Antibodies Against the S Protein

Figure 7:
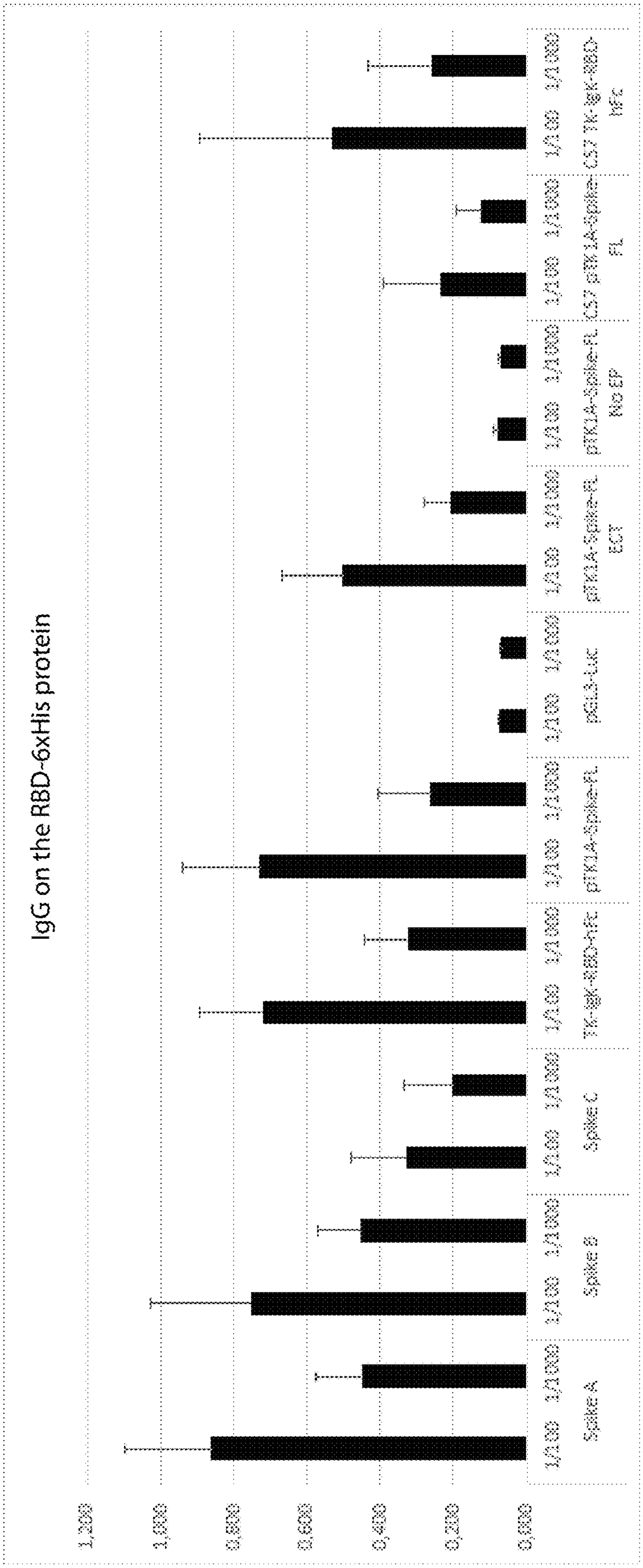
FIG. 7 shows the ELISA analysis of the IgM (A) and IgG (B) antibody response against the RBD portion of the S protein at day 14 after the first treatment.
Figure 7:
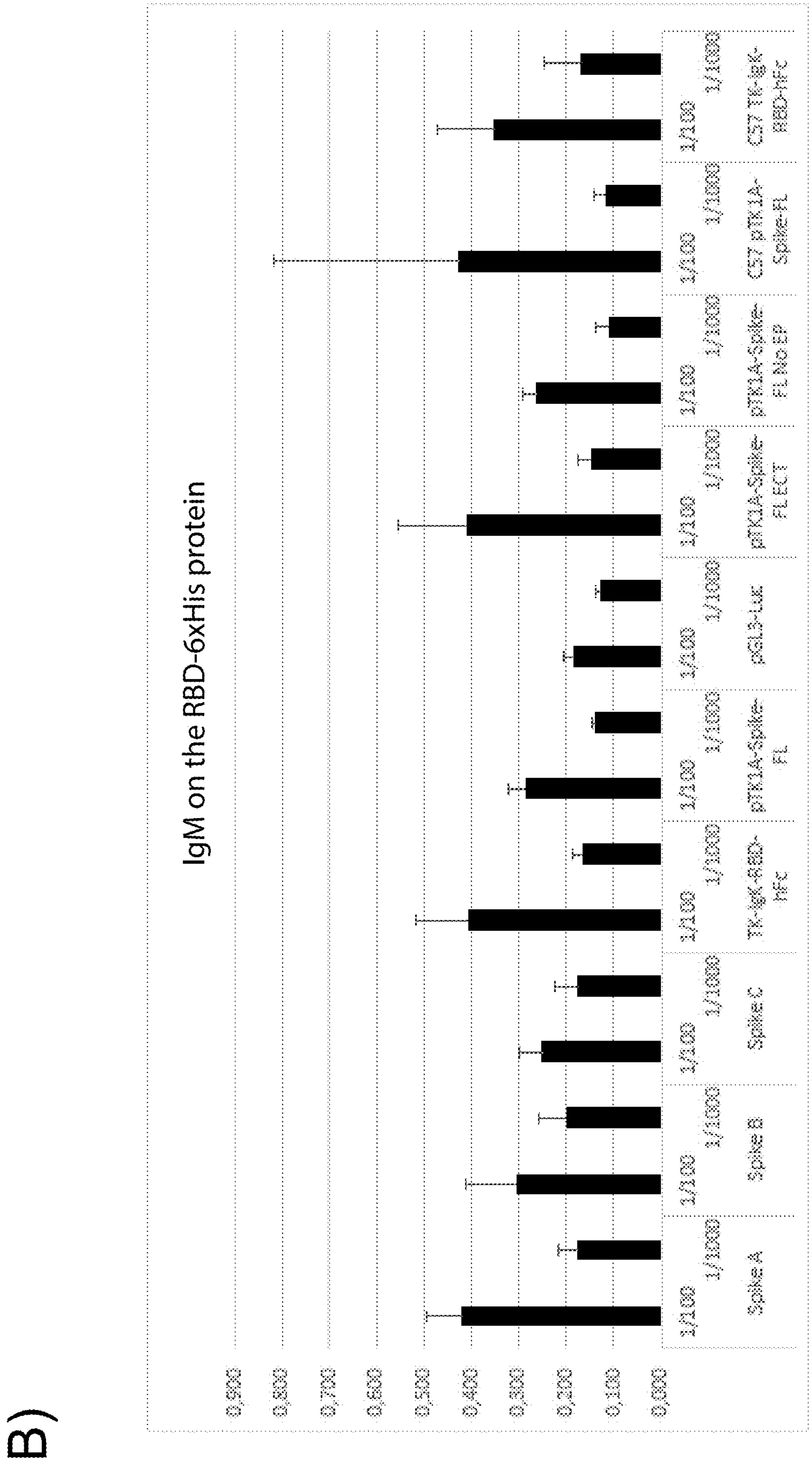
Figure 8:
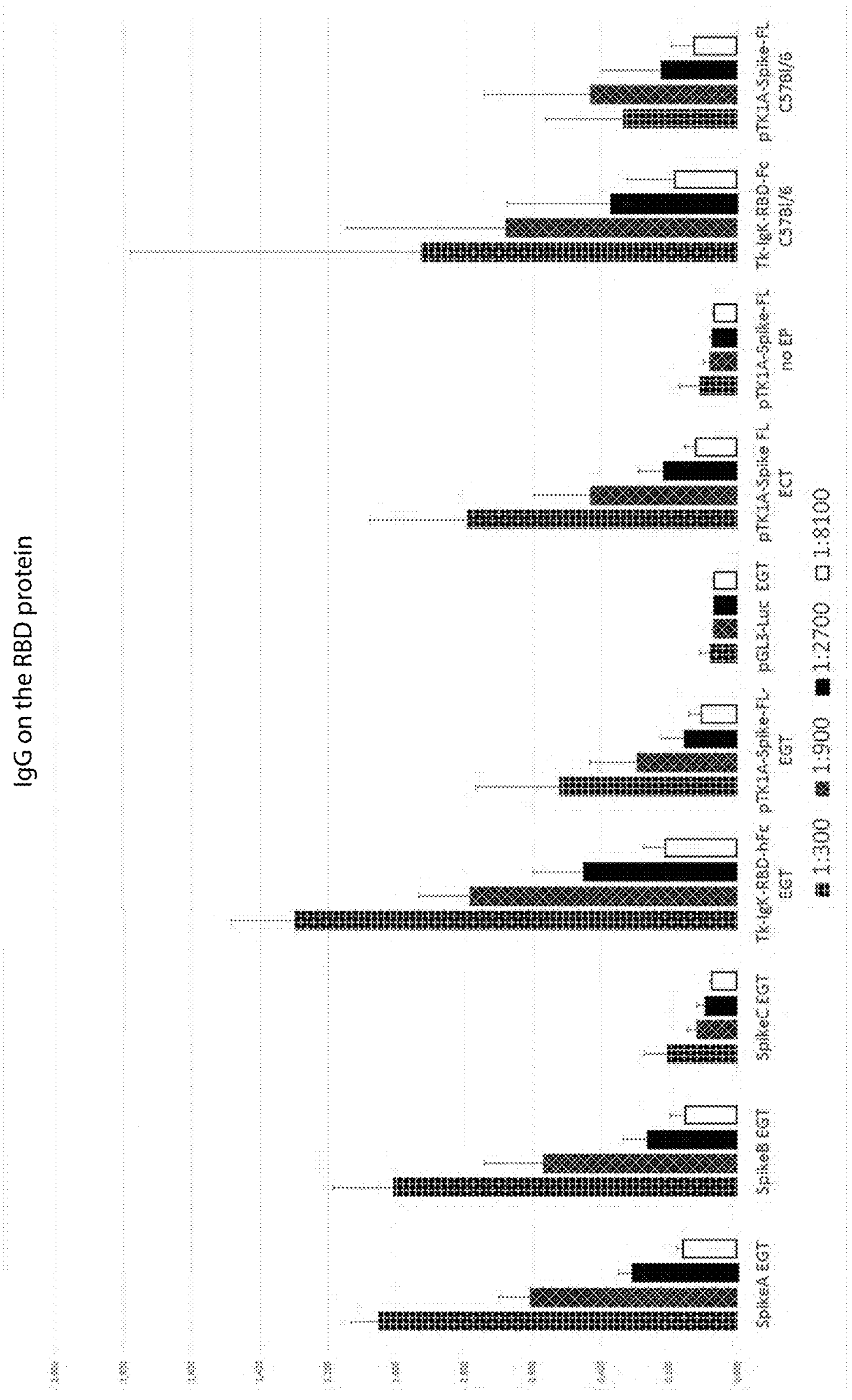
FIG. 8 shows the anti-RBD IgG antibody titre determined by ELISA at day 21 after the first treatment.

ELISA plates were functionalised by coating with the RBD-6×HIS protein at a concentration of 1 μg/ml and incubated for about 18 hours at 4 C. Subsequently, the plates were blocked with 3% BSA/0.05% Tween-20/PBS for 1 hour at room temperature and then the excess solution was eliminated by overturning. The sera of immunised mice were then added at a dilution of 1/100 and 1/100, in duplicate, and the plates incubated for 2 hours at room temperature. After double washing with 0.05% Tween-20/PBS, anti-mouse IgG or anti-mouse IgM secondary antibody conjugated with alkaline phosphatase was added and the plates were incubated for 1 hour at room temperature. After double washing with 0.05% Tween-20/PBS, the binding of the secondary antibody was determined by adding the substrate for alkaline phosphatase and measuring the absorbance at 405 nm by means of an ELISA reader after 2 hours of incubation. The IgM (A) and IgG (B) antibody response against the RBD portion of the S protein was assessed by ELISA at day 14 after the first treatment (FIG. 7). Furthermore, the anti-RBD IgG antibody titres were determined by ELISA at day 21 after the first treatment (FIG. 8).

Example 7. Quality of the Antibodies Against the S Protein Determined by FACS

Figure 9:
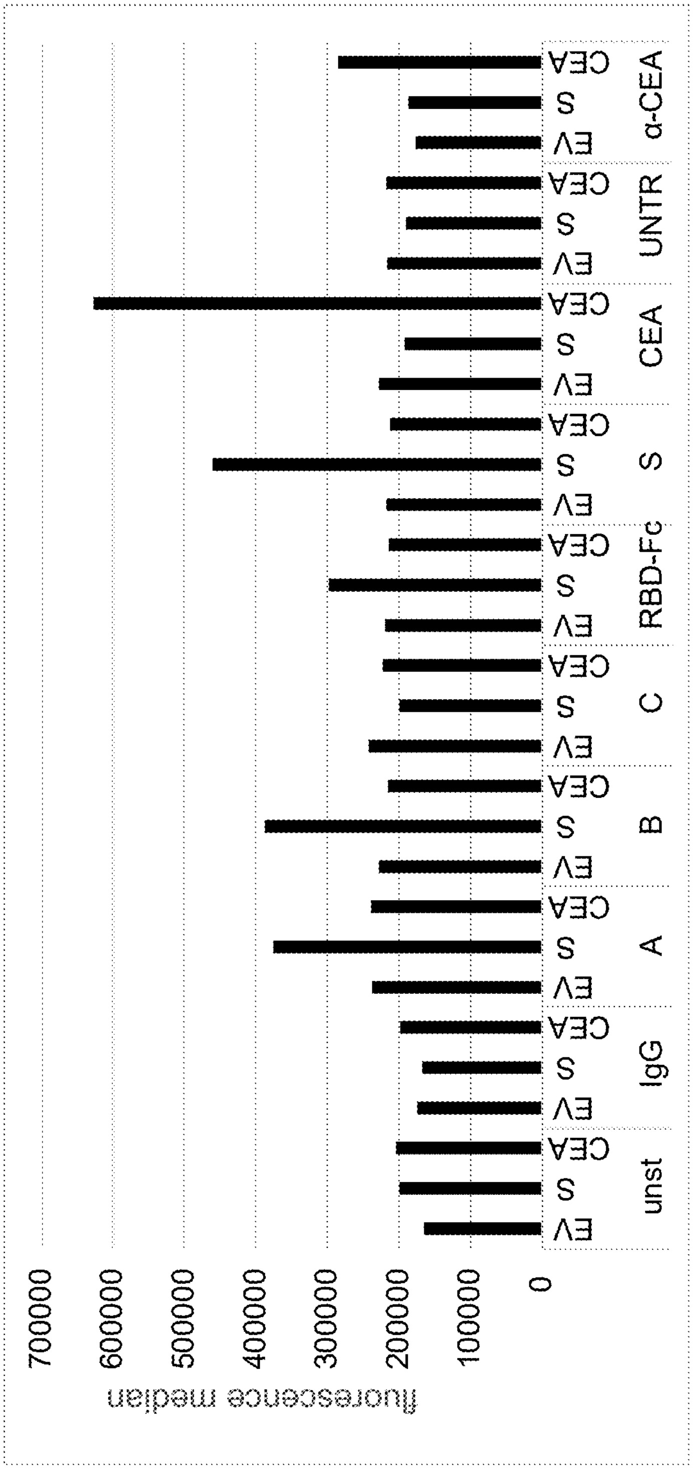
FIG. 9 shows the quality of the antibodies generated at day 14 by cytofluorimetry. HEK293 cells were transfected with a construct that expresses the full-length S protein and incubated with serum of the vaccinated mice and pooled by group. A) Median fluorescence of the transfected cells. B) binding percentage of the transfected cells. The analysis was carried out with a CytoFLEX (Beckman Coulter). EV, empty Vector, CEA, carcinoembryonic antigen.
Figure 9:
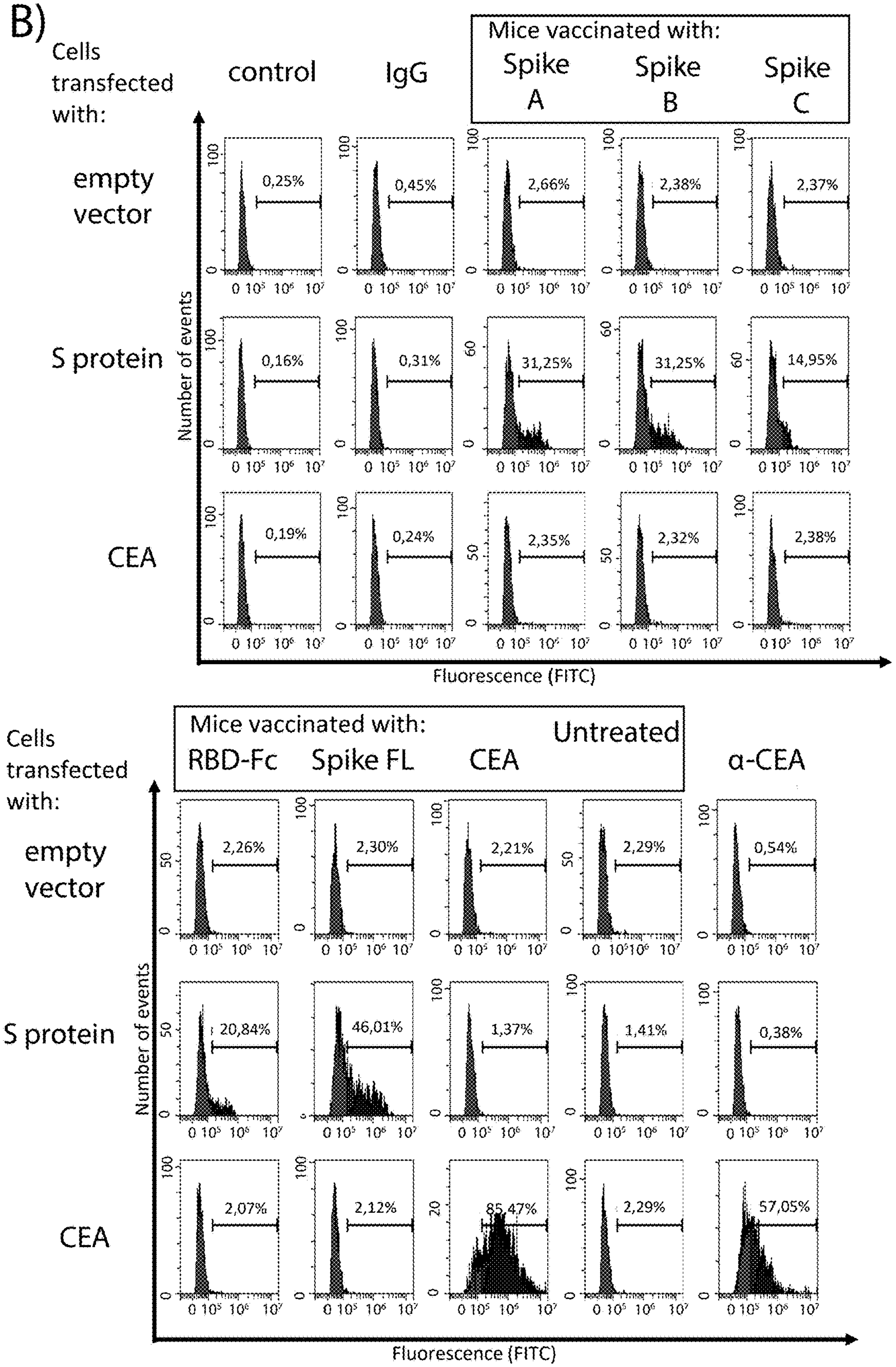

In order to confirm the validity of the vaccines, the ability of the antibodies to bind to the spike protein expressed on human cells was analysed. 293 cells were transfected with the pNEBAd6-Spike-FL construct, which, like the others, had the regulation elements of the human CMV promoter and bGH as the termination site and after 24 hours they were incubated with different dilutions of the mouse sera. A group of vaccinated mice with a construct expressing CEA (carcinoembryonic antigen) and transfected cells with the same construct were used as a positive control for the experiment. The results show that the antibodies recognise the S protein present on the surface of the cells to a significant degree in all of the cases analysed (FIG. 9)

Example 8. Neutralising Titre Against SARS-CoV-2

These studies were conducted in accordance with the current standards of the Spallanzani Institute in Rome, which was the first to isolate the SARS-CoV-2 virus in Italy and possesses BSL-3 and BSL-4 facilities authorised by the Ministry of Health to handle the virus, which was not genetically modified and thus does not represent a GMO.

In order to verify whether the sera of vaccinated animals can neutralise the infectivity of the SARS-CoV-2 virus, a neutralisation assay was performed. Vero cells (10,000 cells/well) were seeded 24 hours prior to infection in a 96-well plate (Costar). On the day of infection, the cells were washed twice. The mouse serum samples were incubated at 56° C. for 30 minutes and then diluted 2 times in cell culture medium. Aliquots (100 μL) of diluted (from 10 to 10240 times) serum samples were added to the cell culture medium containing 100 viral particles of nCoV/Italy-INM11 (virus isolated from the Spallanzani hospital in Rome, sequence deposited in GISAID and GenBank, accession numbers MT008022, MT008023, MT066156 and MT077125) in a 96-well plate and incubated at 37° C. for 30 minutes in CO2, 5% vol/vol. The mixture of virus antibodies was then added to the cells in 96-well plates and the plates were incubated at 37° C., with a microscopic examination for the cytopathic effect after 3 days of incubation. The maximum dilution of the serum which showed inhibition activity against SARS-CoV-2 was recorded as the neutralising antibody titre. The tests were performed in duplicate with negative control samples from unvaccinated mice and a positive control sample from a patient who overcame COVID-19 with a good neutralising titre.

The results of the experiment show that, after the second injection, all of the constructs except Spike C induced the production of mouse sera capable of neutralising SARS-CoV-2.

In particular, the most potent one, with an average of neutralising antibodies of 1:1383 proved to be pTK1A-TPA-Spike A, followed by pTK1A-IgK-RBD-Fc (1: 785), pTK1A-Spike-FL (1:737) and pTK1A-TPA-Spike B (1:189). The results are shown in table 3.

TABLE 3

| | Spike A | Spike B | Spike C | Full-Length Spike | IgK-RBD-Fc |
|---|---|---|---|---|---|
| | 3182 | 301 | 39.33 | 516.2 | 266.3 |
| | 976.5 | 80 | 0 | 604.7 | 918.2 |
| | 1288 | 64.93 | 20.8 | 405.7 | 818.7 |
| | 973.4 | 115.8 | 0 | 1729 | 310.2 |
| | 498.3 | 277.9 | 38.14 | 430.1 | 1614 |
| Mean | 1383.64 | 189.9075 | 19.654 | 737.14 | 785.48 |
| SD | 1044.166 | 117.1829 | 19.38266 | 559.9703 | 547.86 |

Example 9. Administration of a Vaccine According to the Present Invention

According to the sequence of the Coronavirus that causes an epidemic or a pandemic, a vaccine is designed based on plasmid DNA or DNA obtained by PCR. The vector is sent to a CDMO for large-scale production conforming to GMP quality standards. Once the release tests have been carried out, the COVID-eVax vaccine is sent to the hospital, which performs the vaccination using the Cliniporator® or another system of electroporation or administration of DNA. One treatment example: 1 mg of vaccine formulated in 1 ml of PBS or saline solution is injected into the patient's deltoid after local anaesthesia and subjected to EP with the Cliniporator® using an N-10-4-B electrode or one with variable geometry. For the DNA-EP in the muscle, the following low-voltage (LV) electric conditions are applied: 8 pulses of 20 msec, each at 110V, 8 Hz, 120 msec interval between each of them, or 4 pulses of 5 msec, each at 40V, 5 msec interval between each of them.

The patient is subjected to a vaccination and treatment after 4 weeks for the booster and after one year. Biomarkers of the acquired immunisation are seroconversion using the methods described in the previous examples.

Example 10. Impact of the TPA Leader Sequence on Expression and Immunogenicity of COVID-eVax Among the embodiments of the present invention, the vaccine consisting of the pTK1A-TPA vector comprising the RBD sequence (Spike-A) was tested. Therefore, in the examples from example 10 to example 20 the term "COVID-eVax" or "COVID-eVax (original version, Wuhan)" refers to the vaccine of the present invention consisting of the pTK1A-TPA vector comprising the RBD sequence (Spike-A; SEQ ID NO:1) fused to the C-terminal end of the TPA secretion leader sequence (SEQ ID NO:16).

Shown below is the portion of the sequence of the "COVID-eVax" vaccine which comprises the TPA secretion leader sequence (SEQ ID NO:16) fused to RBD (Spike-A, SEQ ID NO:1, in bold) by means of the PacI restriction site of sequence TTAATTAAG (underlined) and in which TAA at the end of the portion is a stop codon:

(SEQ ID NO: 6)

ATGGATGCAATGAAGAGAGGGCTCTGCTGTGTGCTGCTGCTG

TGTGGAGCAGTCTTCGTTTCGCCCAGCTTAATTAAGAGGGTGCAGCC

AACCGAGTCTATCGTGCGCTTTCCTAATATCACAAACCTGTGCCCAT

TTGGCGAGGTGTTCAACGCAACCAGGTTCGCAAGCGTGTACGCATG

-continued

GAATAGGAAGCGCATCTCTAACTGCGTGGCCGACTATAGCGTGCTG

TACAACTCCGCCTCTTTCAGCACCTTTAAGTGCTATGGCGTGTCCCC

CACAAAGCTGAATGACCTGTGCTTTACCAACGTGTACGCCGATTCTT

TCGTGATCAGGGGCGACGAGGTGCGCCAGATCGCACCTGGACAGA

CAGGCAAGATCGCCGACTACAATTATAAGCTGCCAGACGATTTCAC

CGGCTGCGTGATCGCCTGGAACAGCAACAATCTGGATTCCAAAGTG

GGCGGCAACTACAATTATCTGTACCGGCTGTTTAGAAAGAGCAATC

TGAAGCCCTTCGAGAGGGACATCTCTACAGAAATCTACCAGGCCGG

CAGCACCCCTTGCAATGGCGTGGAGGGCTTTAACTGTTATTTCCCA

CTGCAGTCCTACGGCTTCCAGCCCACAAACGGCGTGGGCTATCAGC

CTTACCGCGTGGTGGTGCTGAGCTTTGAGCTGCTGCACGCACCAGC

AACAGTGTGCGGACCCAAGAAGTCCACCAATCTGGTGAAGAACAA

GTGCGTGAACTTCTAA

For the purpose of evaluating the impact of RBD secretion on gene expression and immunogenicity, the construct pTK1A-RBD was generated, wherein the TPA secretion leader sequence was removed and the first amino acid was a methionine in position 318 relative to the full-length original Wuhan-Hu-1 spike protein deposited in the database. The sequence is indicated below; ATG and methionine (M) are underlined:

Nucleotide sequence (SEQ ID NO: 12)

ATGAGGGTGCAGCCAACCGAGTCTATCGTGCGCTTTCCTAATA

TCACAAACCTGTGCCCATTTGGCGAGGTGTTCAACGCAACCAGGTTC

GCAAGCGTGTACGCATGGAATAGGAAGCGCATCTCTAACTGCGTGG

CCGACTATAGCGTGCTGTACAACTCCGCCTCTTTCAGCACCTTTAAGT

GCTATGGCGTGTCCCCCACAAAGCTGAATGACCTGTGCTTTACCAAC

GTGTACGCCGATTCTTTCGTGATCAGGGGCGACGAGGTGCGCCAGA

TCGCACCTGGACAGACAGGCAAGATCGCCGACTACAATTATAAGCTG

CCAGACGATTTCACCGGCTGCGTGATCGCCTGGAACAGCAACAATCT

GGATTCCAAAGTGGGCGGCAACTACAATTATCTGTACCGGCTGTTTA

GAAAGAGCAATCTGAAGCCCTTCGAGAGGGACATCTCTACAGAAATC

TACCAGGCCGGCAGCACCCCTTGCAATGGCGTGGAGGGCTTTAACT

GTTATTTCCCACTGCAGTCCTACGGCTTCCAGCCCACAAACGGCGTG

GGCTATCAGCCTTACCGCGTGGTGGTGCTGAGCTTTGAGCTGCTGCA

CGCACCAGCAACAGTGTGCGGACCCAAGAAGTCCACCAATCTGGTG

AAGAACAAGTGCGTGAACTTCTAA

Amino acid sequence (SEQ ID NO: 13)

MRVQPTESIVRFPNITNLCPFGEVFNATRFASVYAWNRKRISNCV

ADYSVLYNSASFSTFKCYGVSPTKLNDLCFTNVYADSFVIRGDEVRQIAP

GQTGKIADYNYKLPDDFTGCVIAWNSNNLDSKVGGNYNYLYRLFRKSNL

-continued

KPFERDISTEIYQAGSTPCNGVEGFNCYFPLQSYGFQPTNGVGYQPYRV

VVLSFELLHAPATVCGPKKSTNLVKNKCVNF*

The vectors, with or without an optimised Kozak sequence upstream of the ATG triplet of the start of translation (pTK1A-RBD and pTK1A-Kozak-RBD, respectively) were transfected into HEK-293F cells and compared with the vector expressing the TPA-RBD protein (pTK1A-TPA-Spike A or COVID-eVax). In detail, 500,000 cells, seeded onto a plate with a diameter of 60 mm, were transfected with 8 g of plasmid DNA using the Lipofectamine 2000 transfection kit (Thermofisher #11668019) in Opti-MEM culture medium. After 72 hours the intracellular expression and expression in the cell supernatant was evaluated by western blotting.

The cell extracts (20 g) and supernatants (60 µl) were loaded onto a NuPage 4-12% gel (Life Technologies NP0335BOX) for electrophoretic separation. This was followed by transfer onto a nitrocellulose membrane, which was incubated for 1 h at room temperature with 5% milk in PBS-0.05% Tween.

The membrane was subsequently incubated with the primary antibody specific for the S1 subunit of the spike protein of SARS-Cov 2 (Sino Biological #40150-T62), diluted 1:1000 in milk-PBS-0.05% Tween20, overnight at 4° C. Three washes in PBS-0.05% Tween were followed by incubation with the secondary anti-rabbit IgG antibody (Biorad, #170-6515) conjugated with the enzyme peroxidase, diluted 1:2000 in milk-PBS-0.05% Tween20. The reaction with the enzyme substrate (Sigma) enabled the detection, by means of the Chemidoc instrument (Biorad), of the chemiluminescence signal that had developed.

An identical electrophoresis run was conducted in parallel to show the normalisation of the extracts. In this case, the membrane, was incubated with the antibody directed against beta tubulin (ABCAM #ab21058) conjugated directly with the enzyme peroxidase, diluted 1:2000 in milk-PBS-0.05% Tween.

Figure 10:
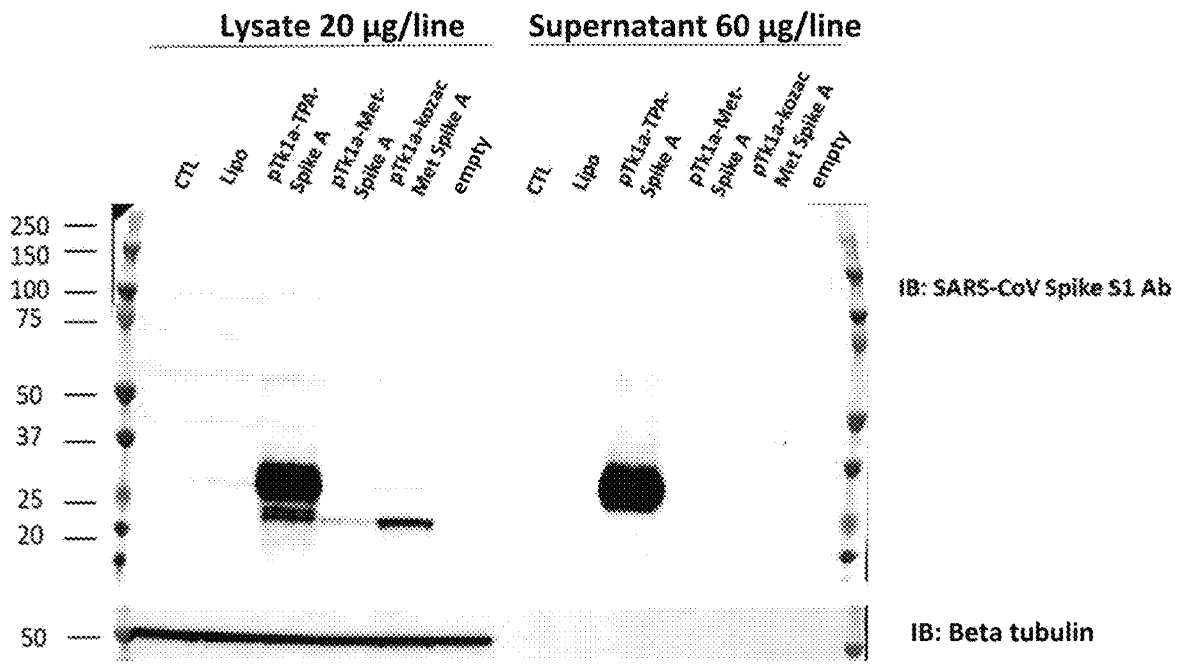
FIG. 10 shows the western blotting conducted on lysates (left) and supernatants (right) of cells transfected with the plasmids indicated at the top. The 27.8 KDa band shows the TPA-RBD protein. The 25.2 KDa band shows the RBD protein. Below, under the lysates, the beta tubulin band used to normalise the proteins present on the membrane.

Surprisingly, FIG. 10 shows a strong intracellular RBD expression by the COVID-eVax construct, whereas the expression by the pTK1A-RBD and pTK1A-Kozak-RBD constructs was much lower. Protein secretion was completely nil, by contrast, in the absence of the TPA secretion leader sequence.

Figure 11:
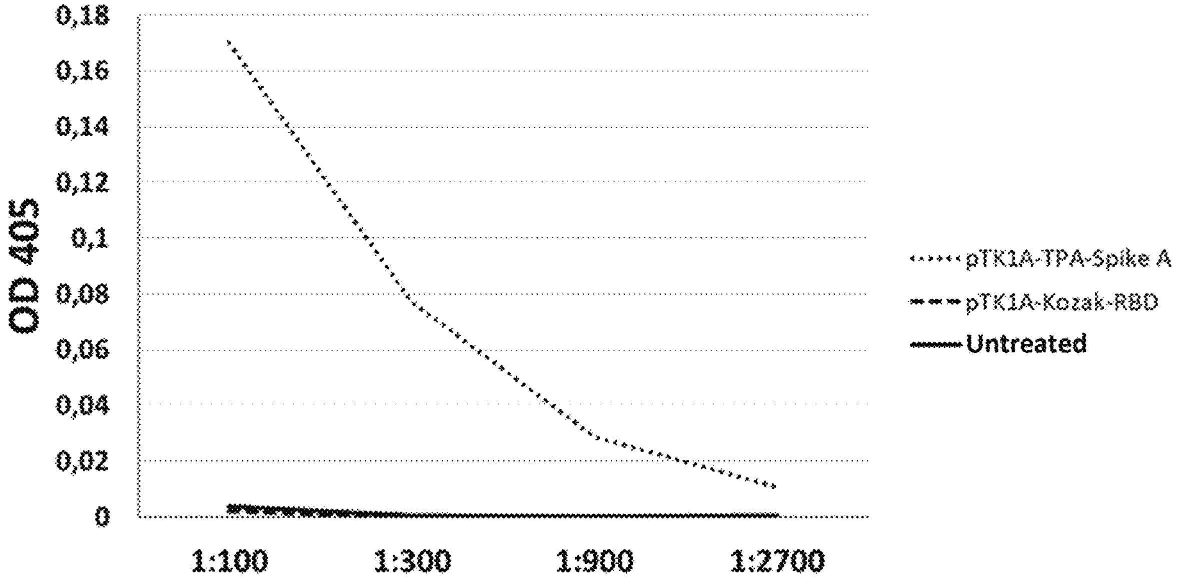
FIG. 11 shows the seroconversion of BALB/c mice (5 per group) 8 days after a single vaccination with 10 μg of pTK1A-TPA-RBD (COVID-eVax) or pTK1A-Kozak-RBD determined by ELISA. The dilutions of the sera range from 1:100 to 1:2700.

In order to assess the impact of the TPA secretion leader sequence on immunogenicity, 2 groups of BALB/c mice were vaccinated with 10 g each of pTK1A-Kozak-RBD or COVID-eVax. After 8 days the seroconversion of the animals was verified by ELISA. As shown in FIG. 11, the mice vaccinated with COVID-eVax showed the presence of antibodies as expected, whereas the mice treated with pTK1A-Kozak-RBD did not give any specific signal. These data demonstrate the advantage of the TPA leader sequence in the expression and secretion of the TPA-RBD antigen for the induction of an immune response.

Example 11. Impact of the Optimised Nucleotide Sequence of RBD (SEQ ID NO: 1) on the In Vitro Expression of RBD The aim of the experiment was to assess whether the sequence optimised for codon usage is capable of providing higher gene expression, which also translates into an enhanced immune response. The wild-type nucleotide sequence that encodes the RBD of the original sequence of the spike gene of the Wuhan-Hu-1 strain (GenBank: MN908947) was synthesised. The sequence was cloned in the pTK1A-TPA expression vector, obtaining the pTK1A-TPA-$RBD_{wt}$ construct. The $RBD_{wt}$ sequence is the following:

SEQ ID NO: 28

AGAGTCCAACCAACAGAATCTATTGTTAGATTTCCTAATATTA

CAAACTTGTGCCCTTTTGGTGAAGTTTTTAACGCCACCAGATTTGCA

TCTGTTTATGCTTGGAACAGGAAGAGAATCAGCAACTGTGTTGCTG

ATTATTCTGTCCTATATAATTCCGCATCATTTTCCACTTTTAAGTGTT

ATGGAGTGTCTCCTACTAAATTAAATGATCTCTGCTTTACTAATGTCT

ATGCAGATTCATTTGTAATTAGAGGTGATGAAGTCAGACAAATCGCT

CCAGGGCAAACTGGAAAGATTGCTGATTATAATTATAAATTACCAG

ATGATTTTACAGGCTGCGTTATAGCTTGGAATTCTAACAATCTTGAT

TCTAAGGTTGGTGGTAATTATAATTACCTGTATAGATTGTTTAGGAA

GTCTAATCTCAAACCTTTTGAGAGAGATATTTCAACTGAAATCTATC

AGGCCGGTAGCACACCTTGTAATGGTGTTGAAGGTTTTAATTGTTAC

TTTCCTTTACAATCATATGGTTTCCAACCCACTAATGGTGTTGGTTAC

CAACCATACAGAGTAGTAGTACTTTCTTTTGAACTTCTACATGCACC

AGCAACTGTTTGTGGACCTAAAAAGTCTACTAATTTGGTTAAAAACA

AATGTGTCAATTTC

An assay when then performed in which the levels of expression of the RBD protein produced by the pTK1A-TPA-RBD vector, comprising the optimised nucleotide sequence of RBD (SEQ ID NO:1), and the pTK1A-TPA-$RBD_{wt}$ vector, comprising the non-optimised nucleotide sequence of RBD (wild type, SEQ ID NO:28), were compared using an indirect ELISA. The comparison and quantification were carried out using a reference curve with the purified recombinant RBD protein included in the same experiment.

In detail, 4 µg of plasmid DNA were incubated in 250 µl of serum-free transfection medium (Opti-MEM Medium-Invitrogen) for 5 minutes. 10 µl of transfection reagent (lipofectamine 2000-Invitrogen) were incubated in the same manner. The DNA was subsequently combined with the reagent to form the transfection complex which was added to the 293F cells plated the previous day at a concentration of $5\times10^5$ cells in 6 wells.

72 hours later, the presence of RBD in the transfection medium was measured by means of indirect ELISA, in which a mouse anti-RBD 5B7-B3 antibody produced by the Applicant, defined as a capture antibody, is capable of binding the RBD present in the transfection medium. The RBD captured by the first antibody was then detected by adding another antibody likewise directed against RBD, in this case rabbit polyclonal antibody, revealed in turn with an antibody directed against it and conjugated with HRP. Finally, the emission of the signal was evaluated in a Tecan microplate reader at a wavelength of 450 nm.

The results demonstrated that the wild-type gene (present in the pTK1A-TPA-$RBD_{wt}$ construct) produced a mean 21.60 µg/ml of RBD protein (with a standard deviation of 3.38 µg/ml) in the cell supernatant, whereas the optimised gene (contained in the pTK1A-TPA-RBD plasmid or "COVID-eVax") induced the secretion of 87.84 µg/ml of RBD protein (with a standard deviation of 19.89 μg/ml). Therefore, the optimised nucleotide sequence SEQ ID NO:1 of RBD provides a gene expression that is 4 times greater than the gene expression provided by the non-optimised RBD nucleotide sequence.

Example 12. Pharmacological Studies

The dose/immune response to vaccination with COVID-eVax was carefully tested in BALB/c and C57Bl/6 mice.

Figure 12:
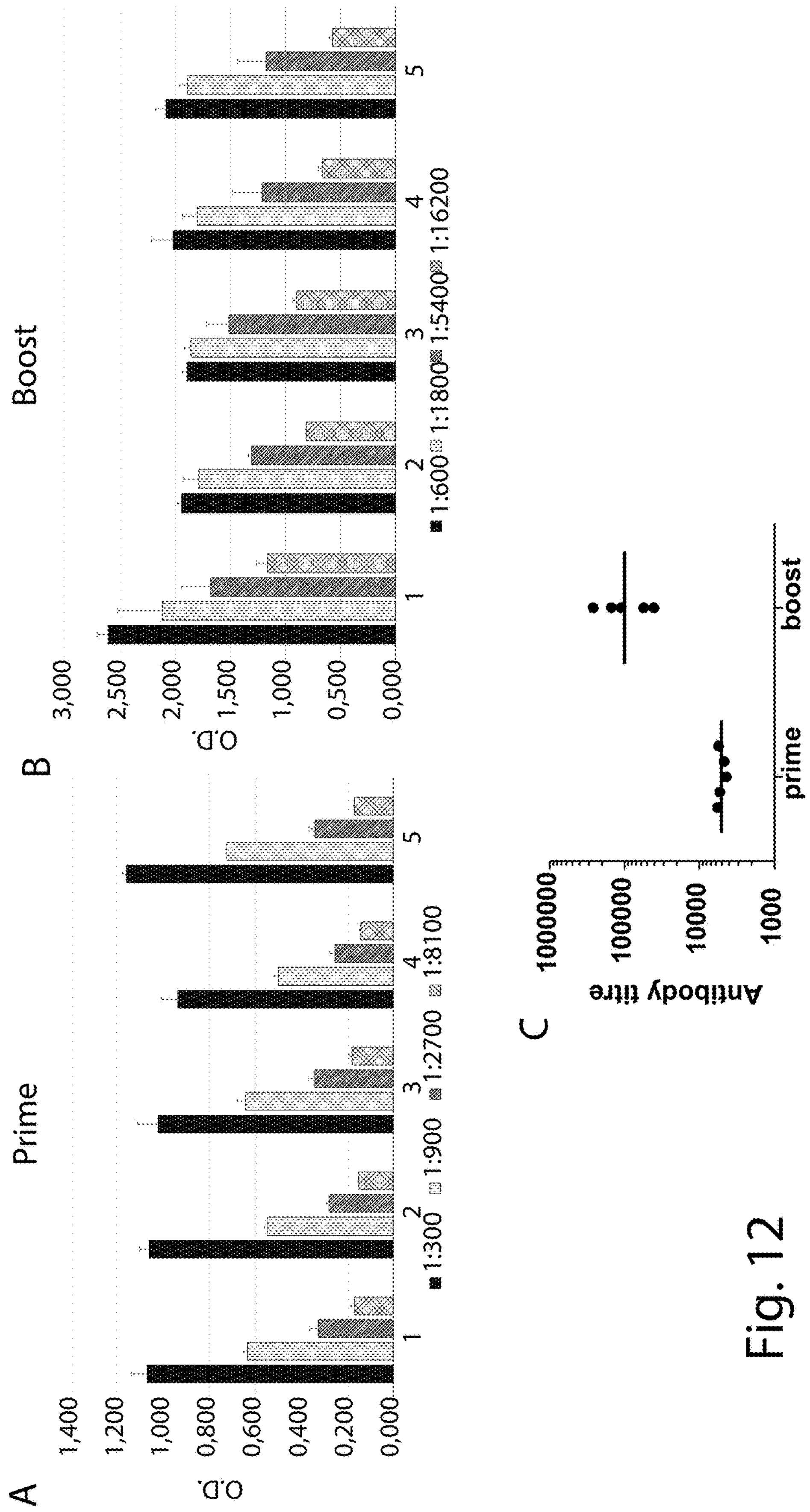
in FIG. 12, in panels A and B, each series of bars represents the optical density (OD) at different dilutions for each individual mouse vaccinated with 20 μg of COVID-eVax. Panel C shows the endpoint titres defined as the last positive dilution (i.e. 3 times the OD in the negative control, or OD 0.2, depending on which is lower) after priming and after the boost.

After a single administration (prime) of 20 μg of COVID-eVax a significant humoral response was observed in BALB/c mice with an endpoint titre of about 5,000. The response increased enormously after a second administration (boost); an endpoint titre of about 100,000 was obtained (FIG. 12).

Figure 13:
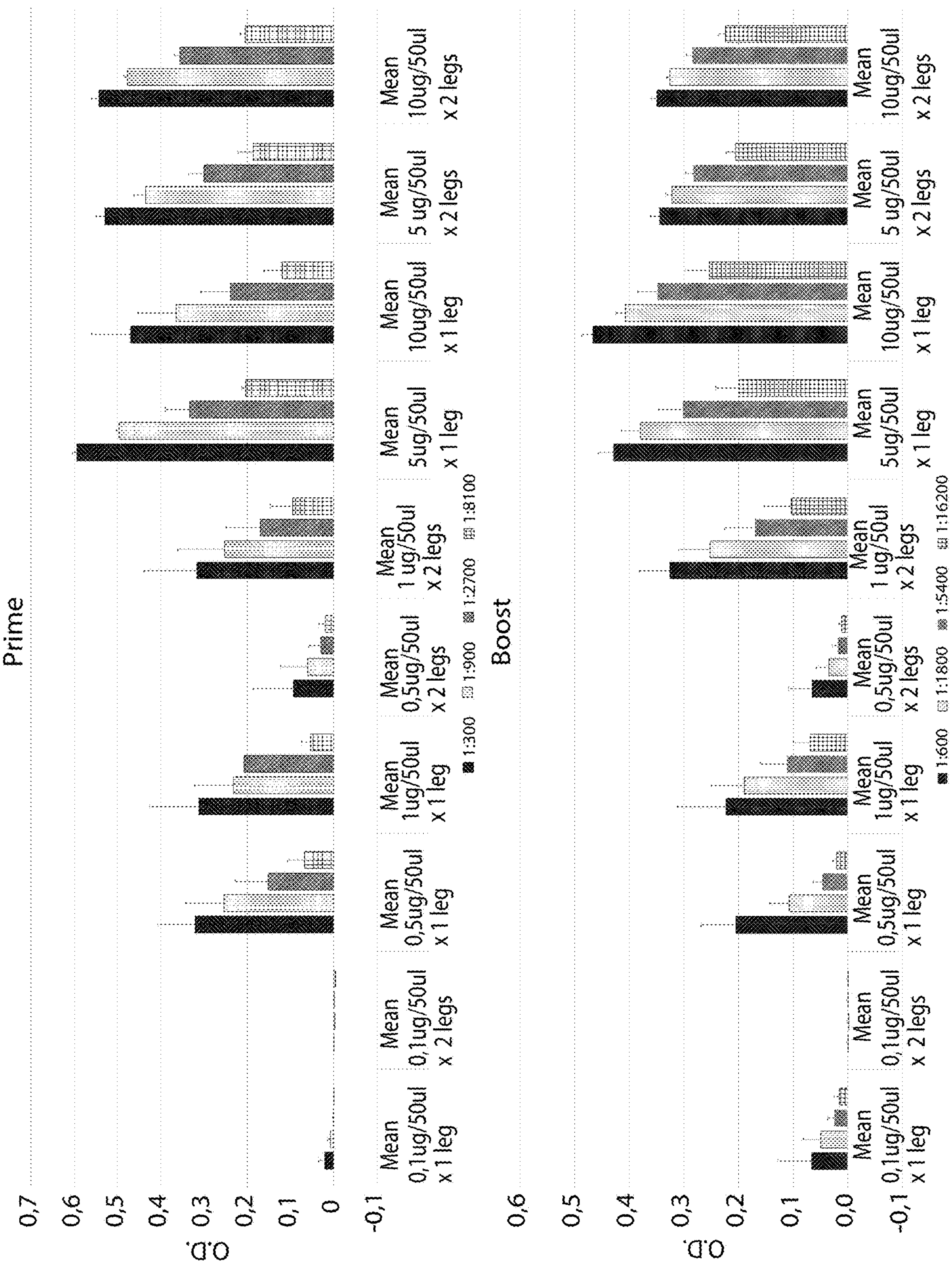
in FIG. 13, each bar represents the mean optical density (OD)±sem for 4-5 young female C57Bl/6 mice vaccinated with different doses of COVID-eVax according to the treatment scheme illustrated on the X axis.

This observation was confirmed in a dose-response test performed in C57Bl/6. Furthermore, a clear dose-dependent effect was observed after both the prime and boost doses, with a plateau reached at doses of 5-10 μg. In fact, the antibody response was already evident after the administration of 0.5-1 μg of COVID-eVax, as may be observed in FIG. 13.

Figure 14:
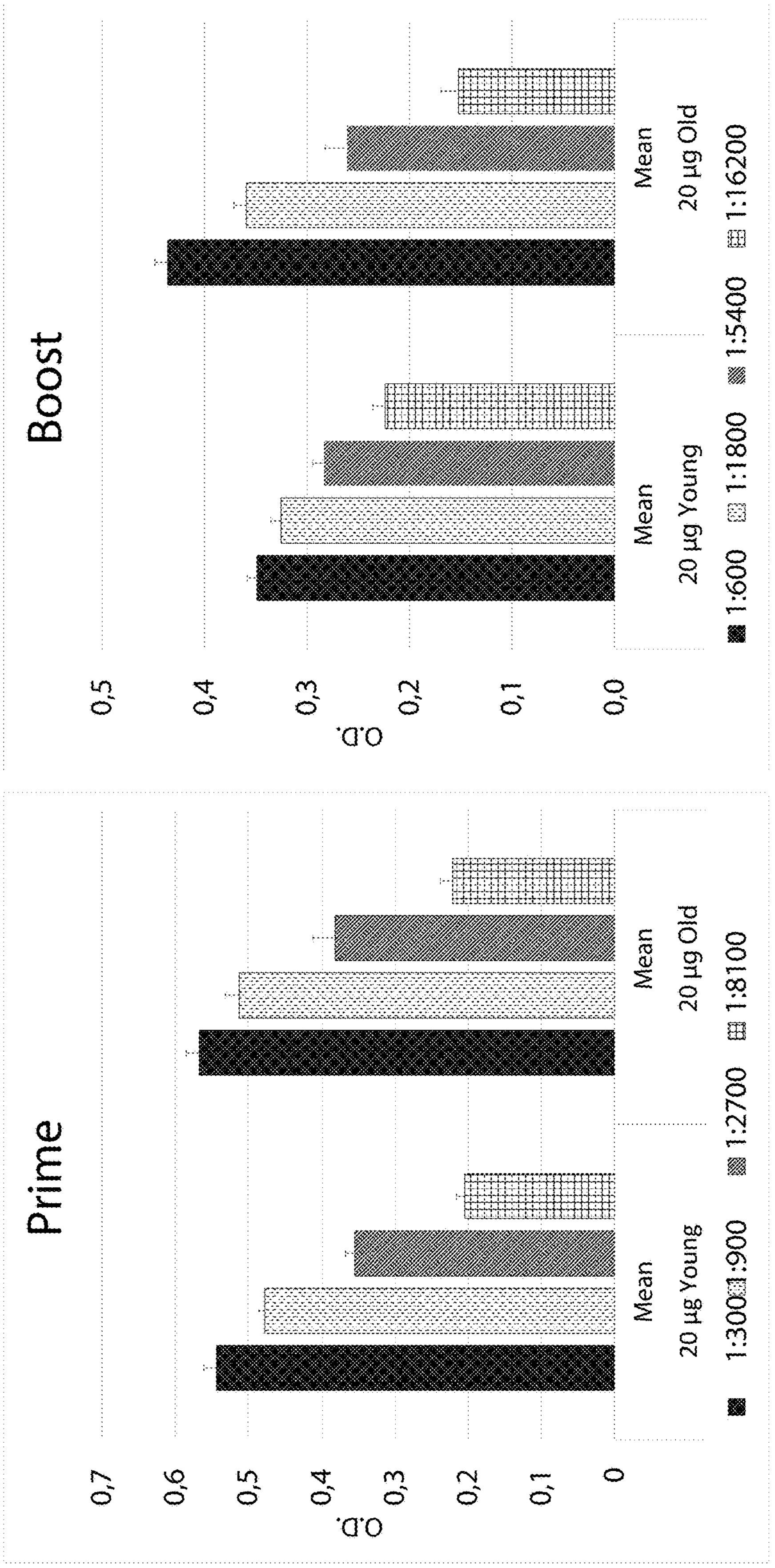
in FIG. 14, each bar represents the mean optical density (OD)±sem for 5 C57Bl/6 female mice aged (~18 months) vaccinated with 20 μg of COVID-eVax compared to C57Bl mice/6 young females.

A similar response was observed in old C57Bl/6 mice (about 18 months old) vaccinated with 20 μg of COVID-eVax. The response was evident after both the prime and boost doses (FIG. 14), confirming that COVID-eVax could be suitable for inducing a high level of immunity also in the elderly.

Example 13. Neutralising Antibodies

Figure 15:
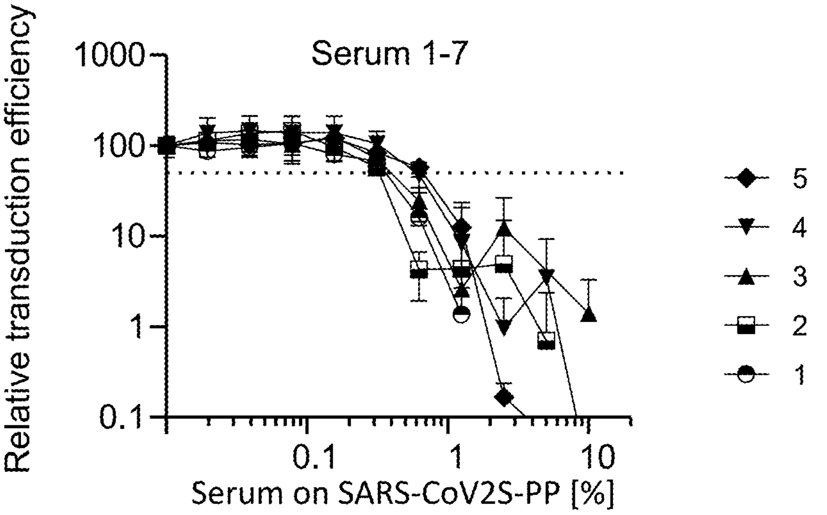
FIG. 15 shows the neutralisation properties of the serum of mice vaccinated with COVID-eVax on pseudotyped viruses based on the VSV system. The dashed line represents 50% of the relative transduction, the intercepts with the inhibition curves of an individual mouse represent the values of IC50. PP stands for Physical Particles of the VSV virus.

The presence of antibodies neutralising the virus was assessed with a pseudoviral particles test based on vesicular stomatitis virus (COV2S-PPs), encoding for eGFP (enhanced green fluorescent protein)+Fluc (firefly luciferase) as a reporter and with a luminescence reading. COVID-eVax was capable of inducing neutralising antibodies with IC50 values comprised between 0.33 and 0.67 (serum % for COV2S-PP, mean SDS, 0.49±0.15). (FIG. 15).

Figure 16:
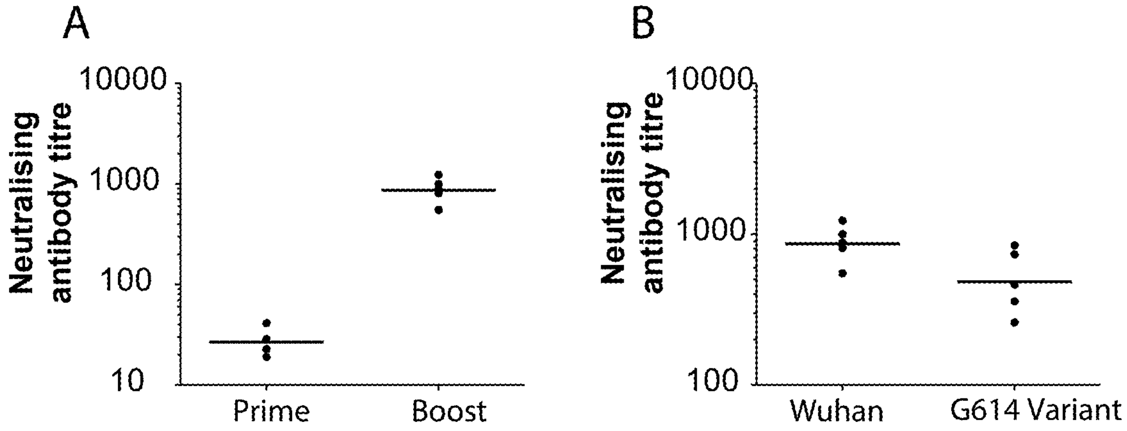
FIG. 16 shows the neutralising antibody titre against SARS-CoV-2 infection in VeRo cells, in Balb/c mice. A. the neutralisation of the reference Wuhan strain after priming (21 days after the vaccination) and boosting (17 days after boosting, or 38 days after priming). B. the neutralisation both of the Wuhan strain and the G614 strain; in many cases the latter has become the dominant local form.

The antibodies present in the serum of mice vaccinated with COVID-eVax were also capable of neutralising wild-type SARS-CoV-2 infection in VeRo cells. Twenty-one days after the first injection, neutralisation was observed in all animals at a 1:20 dilution (mean±DS, 28±10). The titre increased drastically 14 days after the booster (administered 21 days after priming), as illustrated in FIG. 16A, reaching a value of 894±249 (mean±DS). Vaccination with COVID-eVax demonstrated to be effective in producing antibodies capable of also neutralising the G614 mutant variants now dominant (532±248; FIG. 16B).

A similar result was observed in a study of the dose-response effect conducted on C57Bl/6 mice. In this case, as shown in FIG. 17, the titre of the neutralising antibodies seemed to stabilise at 10 μg, the geometric mean of the values obtained after a dose of 5 μg (231.7 [76.76-699.6, IC 95% of the geom. mean]) being greater than the geometric mean of the titre observed in the sera of convalescent patients (158.3 [15.1-1663.0]). The neutralising responses of young and old C57Bl/6 mice were compared in FIG. 17. In the older animals, the response appeared to be lower than the one observed in still young mice (187.6 [95.7-369.2] vs 753.1 [343.2-1653], respectively, p=0.0371), but nonetheless in the interval of responses observed in the sera of convalescent subjects, as shown above.

Example 14. Cell Responses

A B-cell ELISPOT assay for antigen-specific IgG was performed according to the standard procedures. Briefly, the plates were functionalised with the RBD-6His recombinant protein at a concentration of 2 μg/ml and incubated for 18 hours at 4° C. The plates were washed 6 times with 0.05% tween/PBS and the specific sites were blocked with complete RPMI medium for 2 hours at 37° C. The B cells were then plated at 500000 cells/well, serial dilutions were performed and the cells were further incubated for 5 hours at 37° C. The plates were subsequently washed 6 times with 0.05% tween/PBS and incubated with the secondary goat anti-mouse IgG-alkaline phosphatase antibody (Southern Biotechnology #1030-04) diluted 1:2000 in 1% BSA/PBS and incubated at 4° C. for about 18 hours. The following day, the plates were washed 6 times with 0.05% tween/PBS and the BCIP/NBT substrate was added (cat #3650-2 Mabtech). The antigen-specific spots were analysed and quantified with an ELI-SCAN A-EL-VIS instrument.

Figure 18:
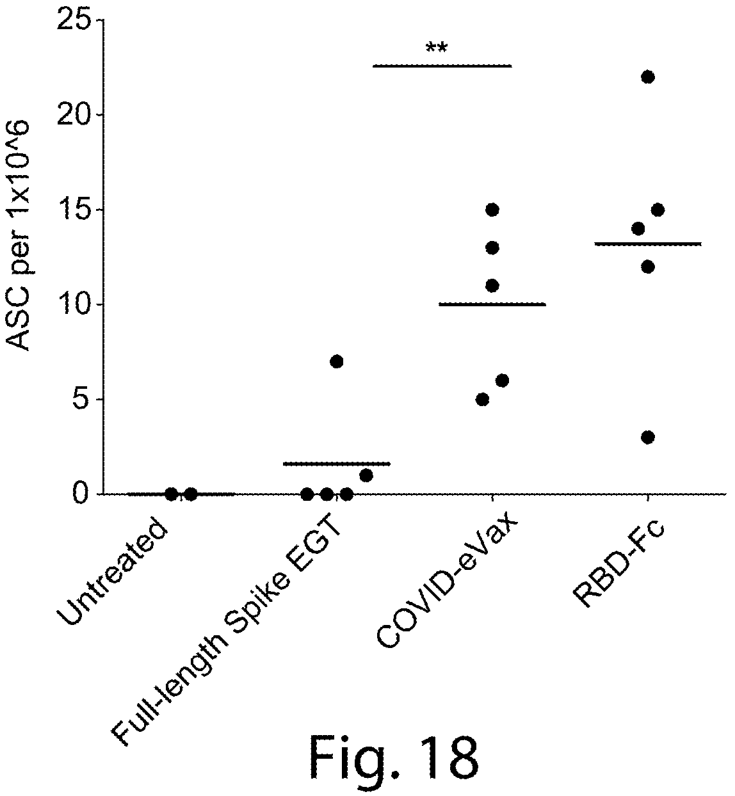
FIG. 18 shows a B-cell ELISpot with splenocytes. The asterisks indicate statistical significance with a t-test, $p<0.01$.

The analysis of the B cells that produce antibodies against RBD, conducted by means of the B-cell ELISpot assay, showed a significantly higher level of specific B cells (ASC, antibody-specific cells) in the mice vaccinated with the COVID-eVax construct compared to those vaccinated with the full-length S protein (FIG. 18).

Figure 19:
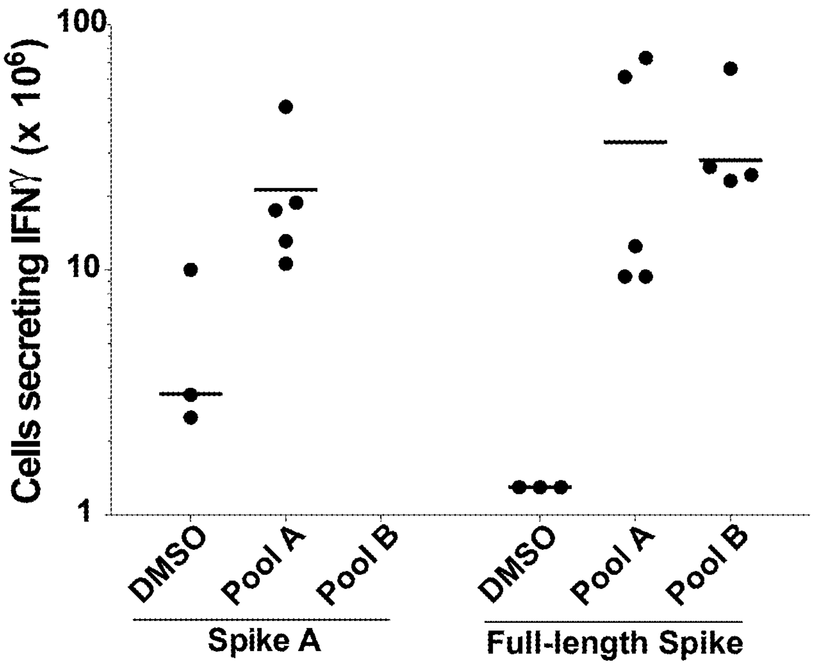
FIG. 19 shows an ELISpot assay on splenocytes that secrete IFNγ when stimulated by pools of peptides which include (pool A) or do not include (pool B) the RBD sequence. The splenocytes were obtained from Balb/C mice vaccinated with 20 μg of COVID-eVax or a plasmid DNA which codes for the entire sequence of the SARS-CoV-2 spike protein sequence (full-length spike).

As regards the Th1 response of the T cells, the ELISpot analysis on splenocytes provided the results illustrated in FIG. 19. The specificity of the immune response after vaccination with COVID-eVax is indicated by the fact that the COVID-eVax vaccination induces a response only when the cells are stimulated with peptides containing the RBD sequence (pool A). In contrast, when the animals are vaccinated with a DNA that encodes the entire sequence of the spike protein (FL), a response is observed also against the peptides that do not contain the RBD sequence (pool B).

Figure 20:
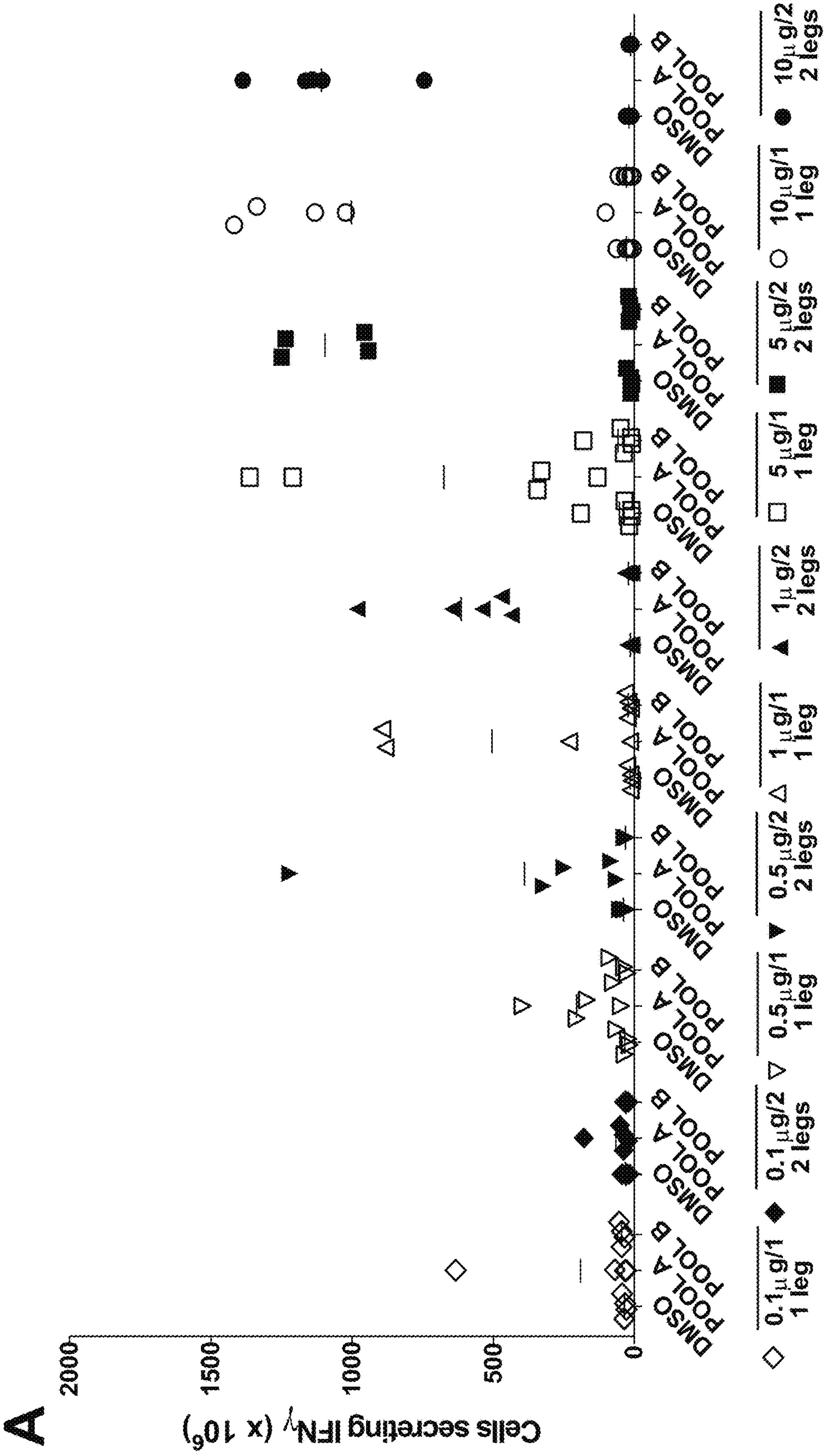
FIG. 20 shows an ELISpot assay on splenocytes that secrete IFNγ when stimulated by pools of peptides which include (pool A) or do not include (pool B) the RBD sequence. The splenocytes were obtained from C57Bl/6 mice vaccinated with increasing doses of COVID-eVax. In panel A, the responses of the individual animal against DMSO, Pool A and Pool B. Panel B shows the non-linear adaptation of the response data to the dose compared to Pool A.
Figure 20:
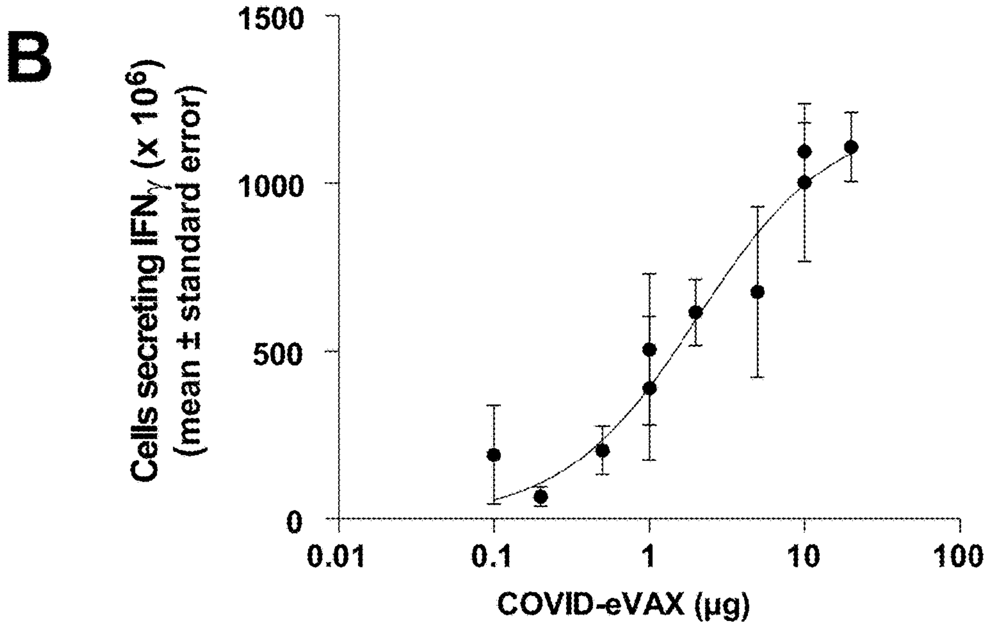

An experiment on the dose-response effect was conducted in C57Bl/6 mice. In this strain the results of the ELISpot assay on IFNγ secreting splenocytes showed a stronger response than was observed in the Balb/C strain and a clear proportionality with the administered dose, as illustrated in FIGS. 19 and 20. As in the Balb/C mice, the response showed to be highly specific, since stimulation with pool B, which did not contain the RBD domain, always produced a response similar to that of the non-stimulated controls (DMSO). The non-linear curve fitting analysis (stimulation of pool A, FIG. 20) provided an ED50 of 2.06±0.86 μg.

Figure 21:
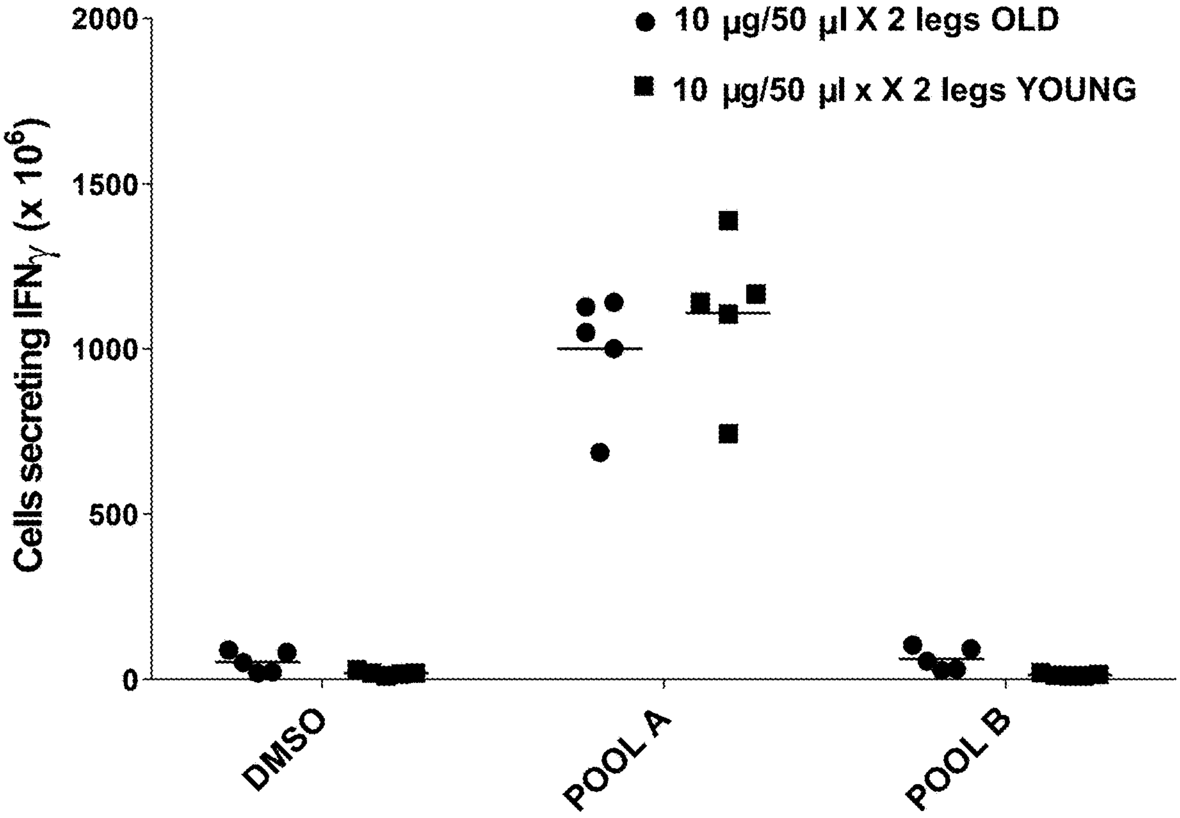
FIG. 21 shows an ELISpot assay on splenocytes that secrete IFNγ when stimulated by pools of peptides which include (pool A) or do not include (pool B) the RBD sequence. The splenocytes were obtained from young or old C57Bl/6 mice vaccinated with 20 μg of COVID-eVax.

A similar response was observed after the vaccination of old C57Bl/6 mice (about 18 months) with 20 μg of COVID-eVax (FIG. 21). This demonstrates that COVID-eVax is highly effective also in older animals.

Figure 22:
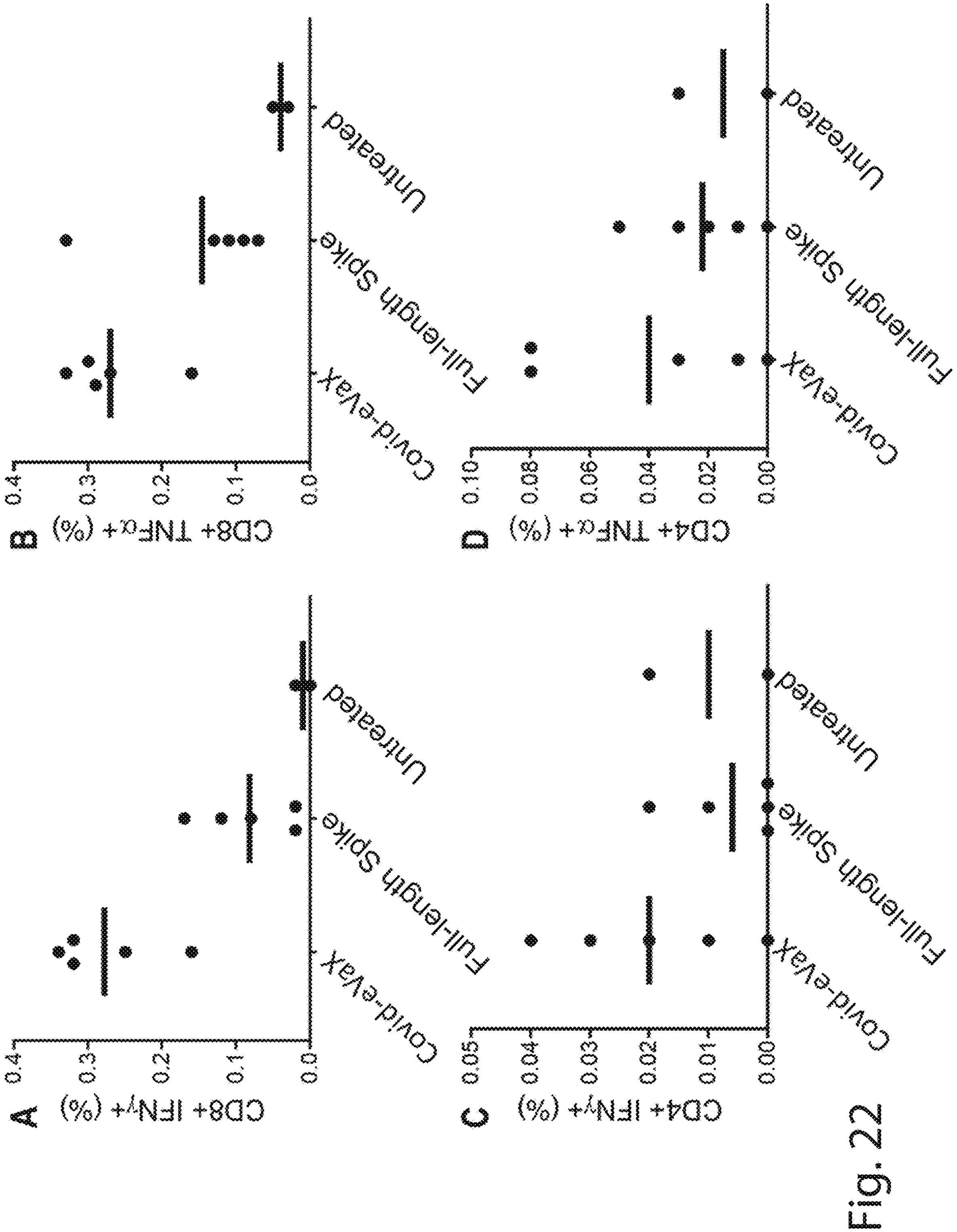
FIG. 22 shows the intracellular cytokine staining, by flow cytometry, of selected CD8+ (left) and CD4+ (right) anti-spike T cells on live CD3+ cells in BALB/c mice.

The cellular immune response following the COVID-eVax vaccination was analysed using intracellular cytokine staining (ICS) technology with FACS in order to simultaneously evaluate the cytokines produced by different populations of T cells, which are characteristic of a prevalent Th1 or Th2 response. In the study conducted on Balb/C mice (FIG. 22), COVID-eVax induced higher levels of the T-cell immune response of the Th1 type (IFNγ and TNFα) in CD8+ cells (cytotoxic T lymphocytes) compared to Spike FL. A lower but nonetheless measurable response was also observed, however, in CD4+ cells (T-helper lymphocytes). This predominance of the CD8+ response in mice seems to be a characteristic of the majority of the COVID-19 vaccines being developed.

Figure 23:
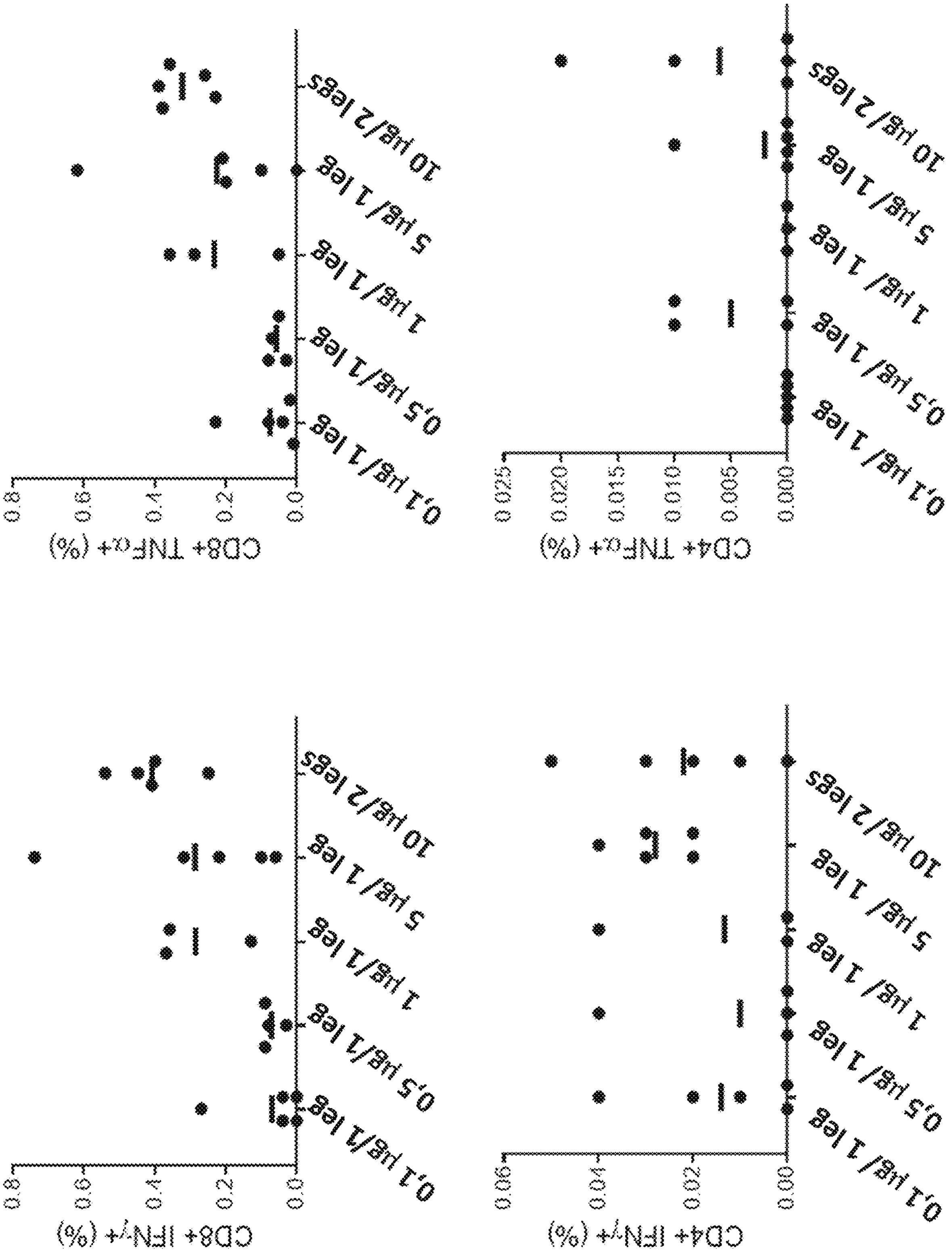
FIG. 23 shows the intracellular cytokine staining, by flow cytometry, of selected CD8+ (left) and CD4+ (right) anti-spike T cells on live CD3+ cells in C57Bl/6 mice.

This response was confirmed in the C57Bl/6 mice; in fact, in this strain as well the response was greater in the CD8+ cells and was correlated with the dose administered (FIG. 23). Groups of mice were vaccinated with doses ranging from 0.1 to 10 g, in only one or two legs (quadriceps).

Figure 24:
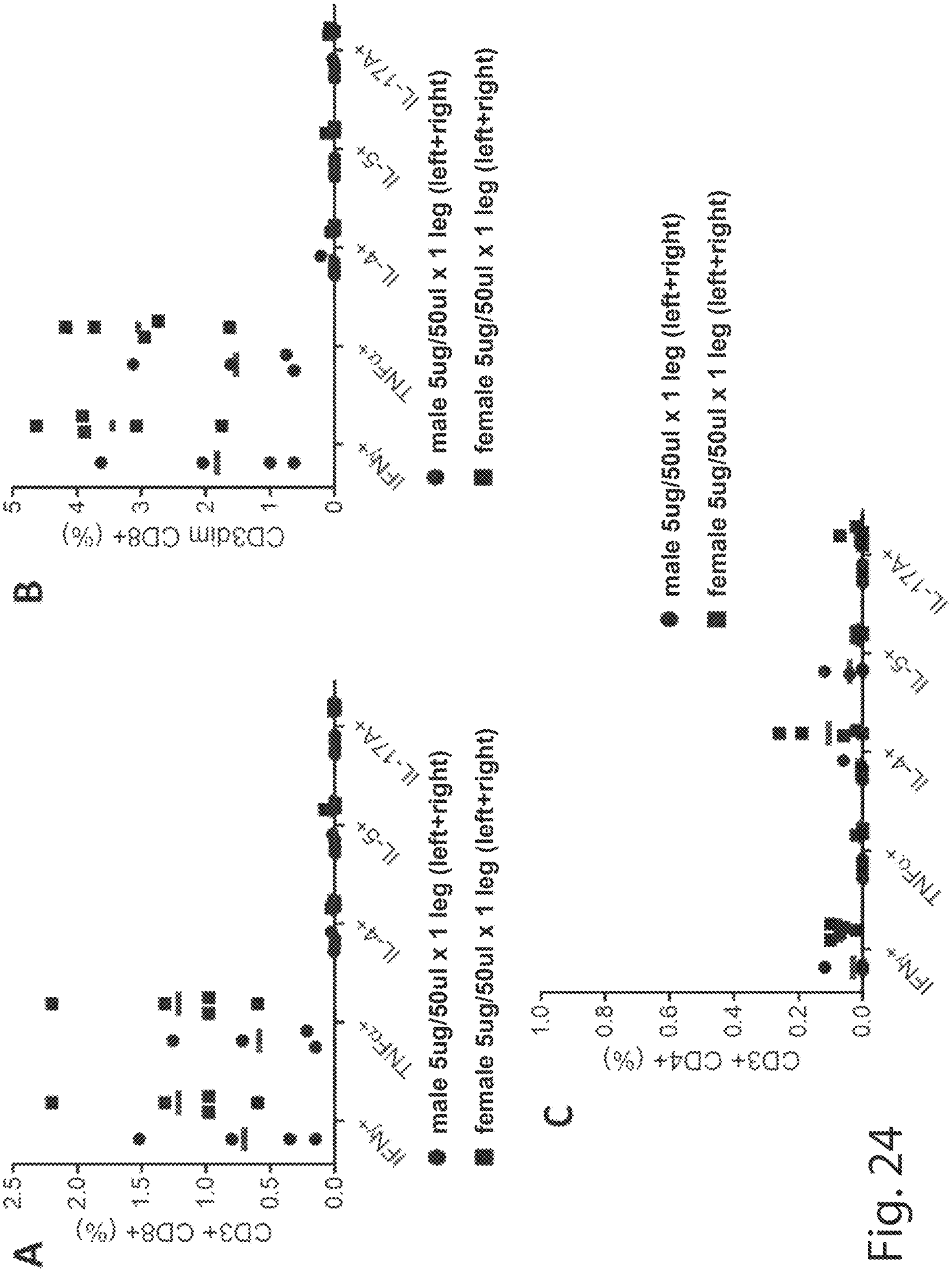
FIG. 24 shows the intracellular staining, by flow cytometry, of selected mature (A) and immature (B) CD8+ and CD4+ (C) anti-spike T cells from selected splenocytes on live CD3+ cells. The inserts in panel C show the graph of the individual FACS analysis, demonstrating the negligible level of activation of Th2 in these mice as well.

The effect of COVID-eVax on the T-cell response was assessed by ICS in groups of male and female C57Bl/6 mice vaccinated with a dose of 5 μg/animal. This study confirmed that the most evident Th1 response (IFNγ and TNFα) in this strain involves the CD8+ cells and that the Th2 (IL-4, IL-5) and Th17 responses are nearly absent (FIGS. 24A and 24B).

The response of the CD4+ cells in this experiment was almost irrelevant (FIG. 24C) and the apparent Th1 response observed in a few females was likewise negligible. This preferential triggering of a Th1 response supports the safety of the COVID-eVax vaccination against SARS-CoV-2.

Example 15. Intranasal Inoculation of COVID-eVax in Mice

Figure 25:
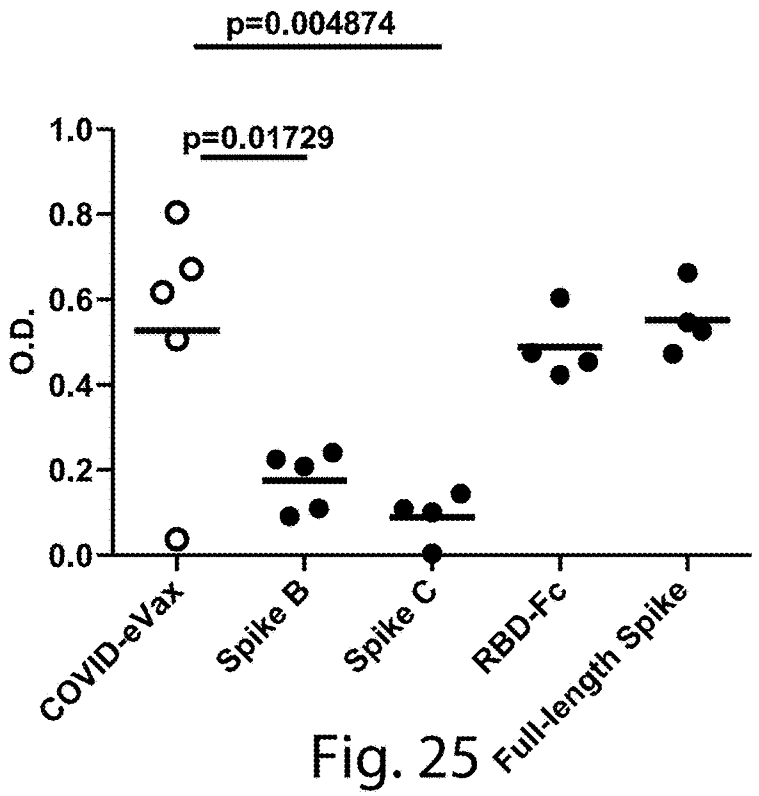
FIG. 25 shows the levels of anti-RBD IgG Immunoglobulines in bronchoalveolar lavages.

Bronchoalveolar lavages (BALs) were studied in order to assess the presence of RBD-specific antibodies in the lungs. The response was assessed 7 days after a booster injection (i.e. 28 days after the first vaccination) and COVID-eVax was administered at a dose of 20 μg. As shown in FIG. 25, COVID-eVax was capable of inducing a higher antibody titre compared to the other plasmids (Spike B and Spike C) and one which was comparable to that of the plasmids covering the full-length spike protein (FL), whether or not conjugated with Fc.

Figure 26:
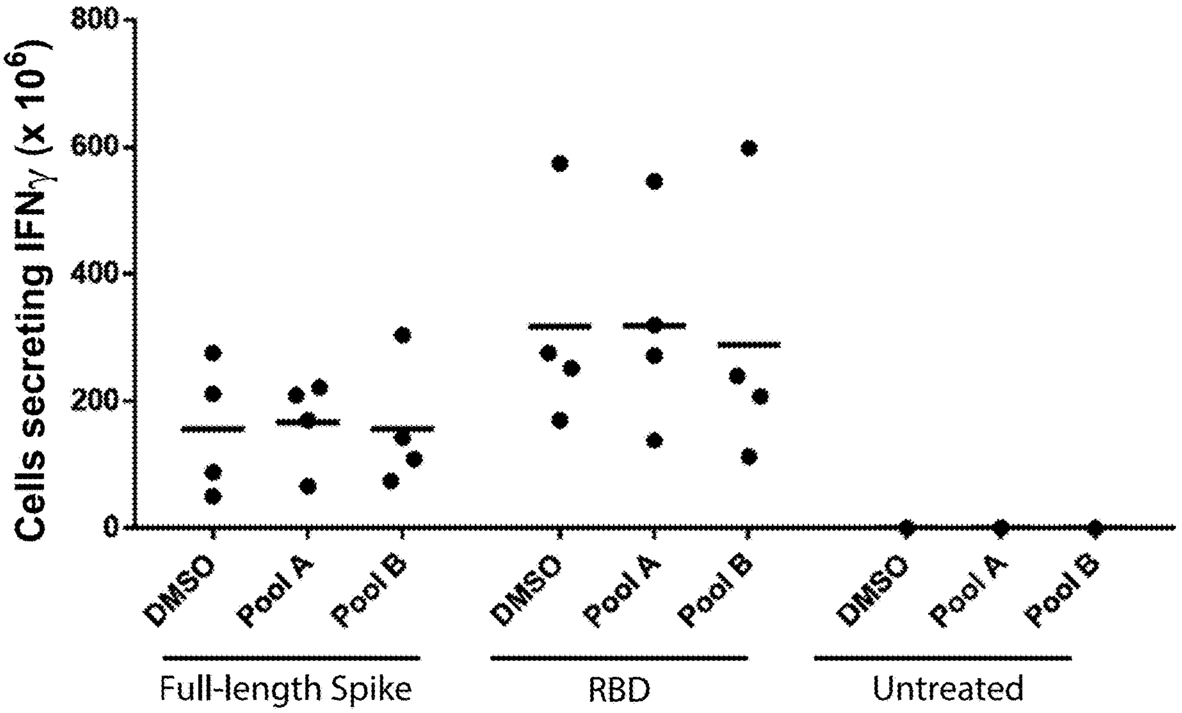
FIG. 26 shows IFNγ-producing T cells in the lungs following intranasal stimulation with the RBD protein.

These data confirm that COVID-eVax is capable of inducing high levels of anti-SARS-CoV-2 antibodies also in the main point of entry of the virus, which corresponds to the system in which it exerts the largest effects. In order to measure the presence of T cells specific for RBD in the lungs, the RBD protein was injected nasally into a group of vaccinated Balb/C mice which were sacrificed the next day. The lymphocytes infiltrating the lung were isolated and the production of IFNγ was measured by means of the ELISpot assay. FIG. 26 shows that both the FL spike protein and COVID-eVax induced a strong local Th1 response. These data confirm that, in the respiratory tract, COVID-eVax is capable of inducing a significant humoral and cellular (type Th1) immune response.

Example 16. Immunogenicity in Rats

In order to demonstrate that rats are capable of developing an effective immune response against SARS-Cov-2 after vaccination with COVID-eVax and thus to validate the choice of this animal species for toxicological studies, 16 female Sprague-Dawley rats (7 weeks old, body weight ranging from 140-155 grams) were treated with three vaccine doses. The intramuscular administration followed a prime-boost scheme (i.e. two administrations two weeks apart). The experimental groups were: n.1-100 μl of PBS; n.2-100 μg of COVID-eVAX (25 μl/side of a 4 mg/mL solution in PBS); n.3-200 μg of COVID-eVAX (50 μl/side); and n.4-400 μg i.m. COVID-eVAX (100 μl/side). The electroporation conditions were the same as the one used in mice, i.e. 8 low-voltage pulses of 20 msec each at 110 V, 8 Hz, with an interval of 120 msec.

The induction of an immune response was tested in the serum of the treated animals by means of an ELISA assay.

In detail, the recombinant RBD protein (1 μg/ml in PBS) was immobilised (50 μl/well) on Maxisorp96 flat plates (Nunc #442404) by overnight incubation at 4° C. Subsequently, 3 washes were carried out (200 μl/well of a solution made up of PBS and 0.05% Tween 20), followed by 1 h of incubation at room temperature with 100 μl/well of a 3% solution of bovine serum albumin (BSA, Sigma-Aldrich #A2153) in PBS/0.05% Tween20 to block the non-specific binding sites. After 3 washes, the rat sera samples were added (50 μl/well) in serial dilutions in 1% BSA-PBS/0.05% Tween20, and allowed to incubate overnight at 4° C.

The plates were washed and the rat IgG-specific secondary antibody, conjugated with the enzyme alkaline phosphatase (Sigma-Aldrich #AP A8438) diluted 1:2000 in 1% BSA-PBS/0.05% Tween20 was added in the wells (50 μl/well) and left to incubate at room temperature for 1 h.

After the washes, the substrate specific for the enzyme alkaline phosphatase (Sigma-Aldrich #P7998) was added (50 μl/well) and the optical density (OD) values at 405 nm were measured by means of an Tecan ELISA reader in a time interval comprised between 30 minutes and 2 hours. The results are shown in the graph.

Figure 27:
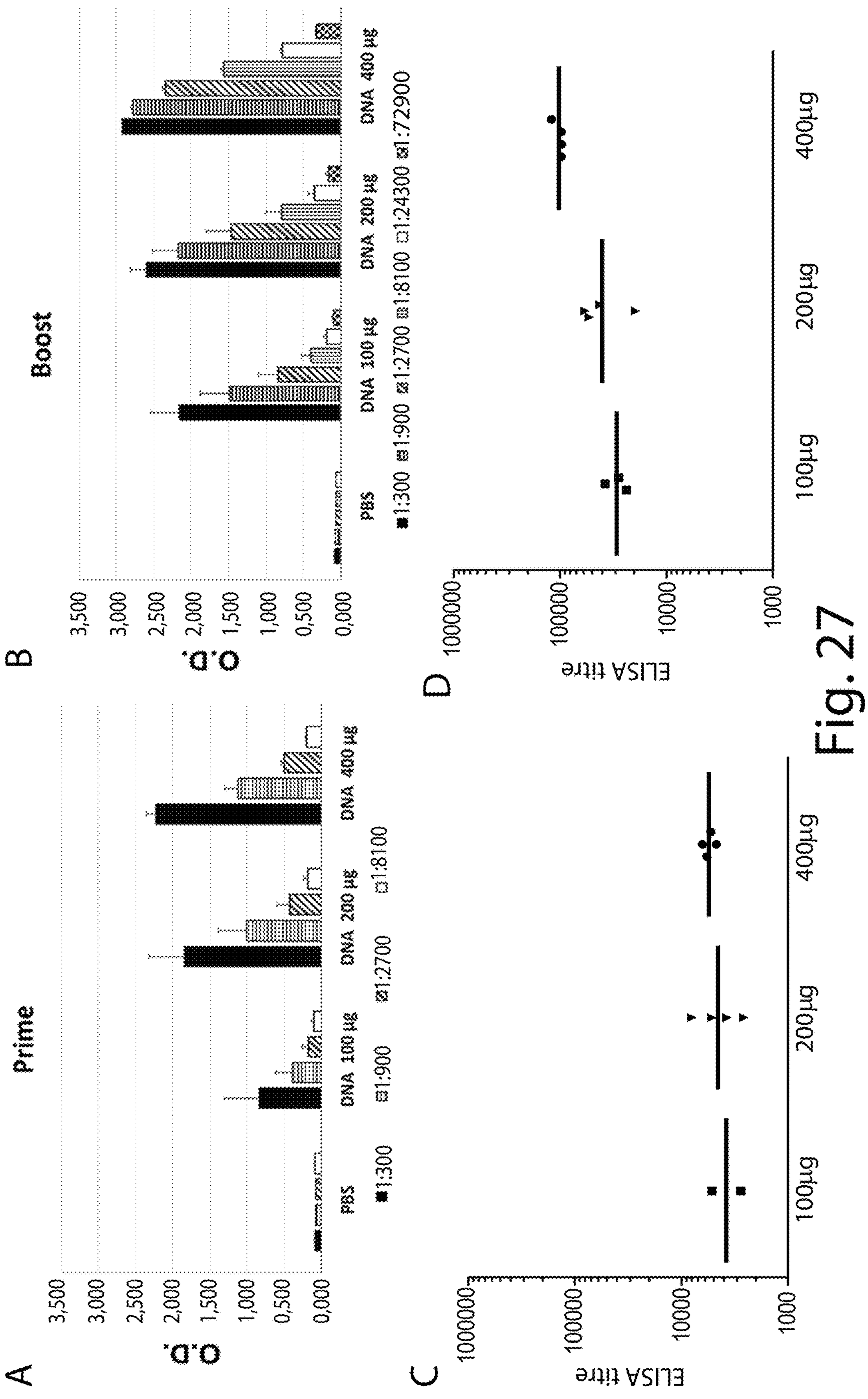
in FIG. 27, in A and B, every bar represents the mean±sem of the optical density (OD) for 4 S.D. rats vaccinated with increasing doses of COVID-eVax after a single primary administration (A) or after a complete prime-boost cycle (B). Panels C and D represent the individual endpoint titre calculated as shown in 6, 14 days after a single main injection (C) or a complete prime-boost cycle (D); the lines indicate the geometric means of the endpoint titre.

The ELISA analysis of the sera collected 14 days after the priming confirms a robust dose-dependent seroconversion, already evident after the administration of 100 μg of DNA. This response was considerably improved after the booster, the titre in the rats treated with the low dose being still significantly higher than the one observed in the animals treated with PBS, also after a 1:24300 dilution ($p=0.0286$; Mann-Whitney test). In the rats vaccinated with 400 μg, the geometric mean of the endpoint titre was 5,517 after priming and 152,991 after the booster. The titre of the smaller doses was proportionally lower than this value. The data are presented in FIG. 27.

Figure 28:
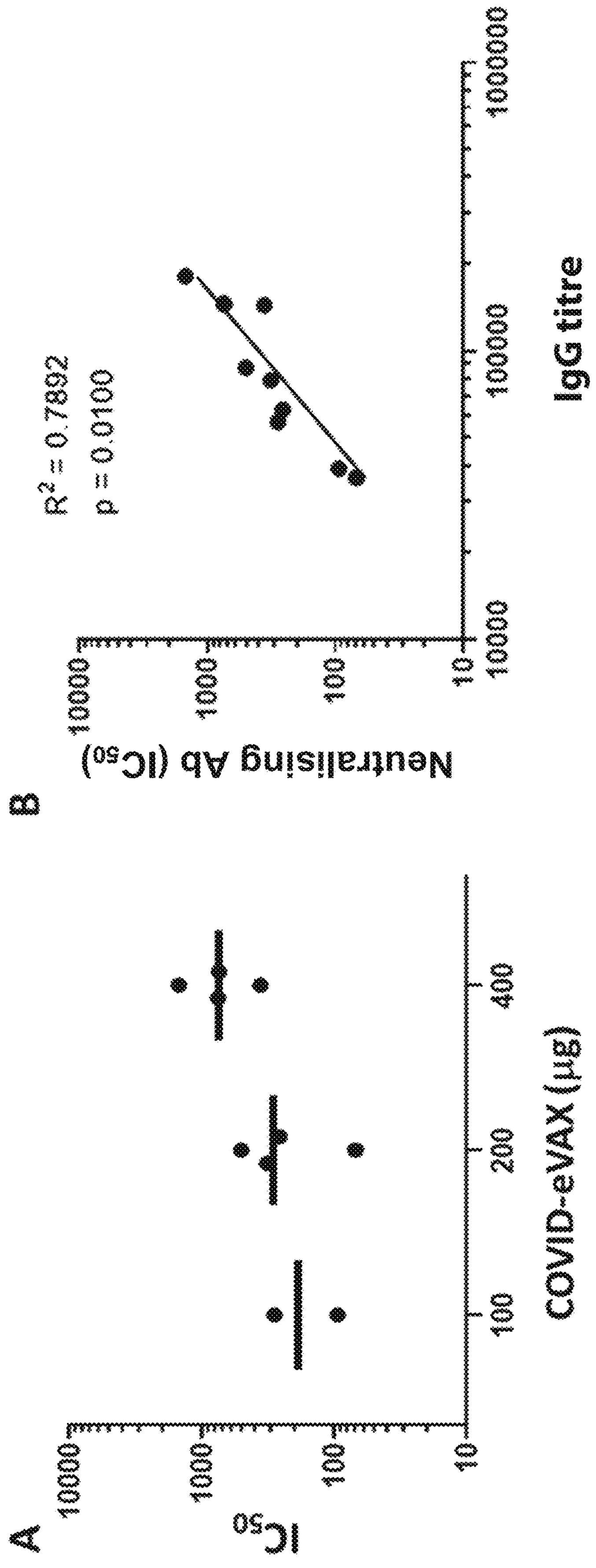
FIG. 28 shows the neutralising antibody titre against SARS-CoV-2 infection in VeRo cells, in Sprague Dawley rats in a dose-response curve after vaccination with COVID-eVax; the line indicates the geometric means. B correlation between the total endpoint titres of IgG and the neutralising antibody, IC50.

Furthermore, in rats, too, the COVID-eVax vaccination induced neutralising antibodies against the infective capacity of SARS-CoV-2, as shown by the IC50 illustrated in FIG. 28A.

FIG. 28B shows an evident, highly significant correlation between the IgG total endpoint titre and the neutralising IC50.

Example 17. ACE2-RBD Binding Competition

Through its RBD domain, the SARS-CoV-2 S protein recognises the ACE2 receptor on the host cell membrane, which allows the entry of the virus. A possible strategy for blocking the entry of the SARS-CoV-2 virus is the binding of the RBD itself to the receptor as a decoy in order to compete with the S protein present on the virus. In principle, SARS-CoV-2, in the presence of the RBD protein, would have limited infective potential. In order to test this hypothesis, an experiment was conducted in Balb/C mice, where 20 g of COVID-eVax were injected into the quadriceps, followed by electroporation, according to the scheme shown in Table 4.

TABLE 4

| Group | Treatment |
|---|---|
| Group 1 | pTK1A-Spike A no EP |
| Group 2 | pTK1A-Spike A EP |
| Group 3 | Untreated |

48 hours later, the presence of secreted RBD was measured in blood and in bronchoalveolar lavages (BALs) by means of indirect ELISA, in which an anti-RBD mouse antibody 5B7-B3 produced by the applicant, defined as a capture antibody, is capable of binding the RBD present in the sera and in the BALs of the electroporated animals. The RBD captured by the first antibody was then detected by adding another antibody, also directed against RBD, in this case a rabbit polyclonal antibody, revealed in turn with an antibody directed against it and conjugated with HRP.

Figure 29:
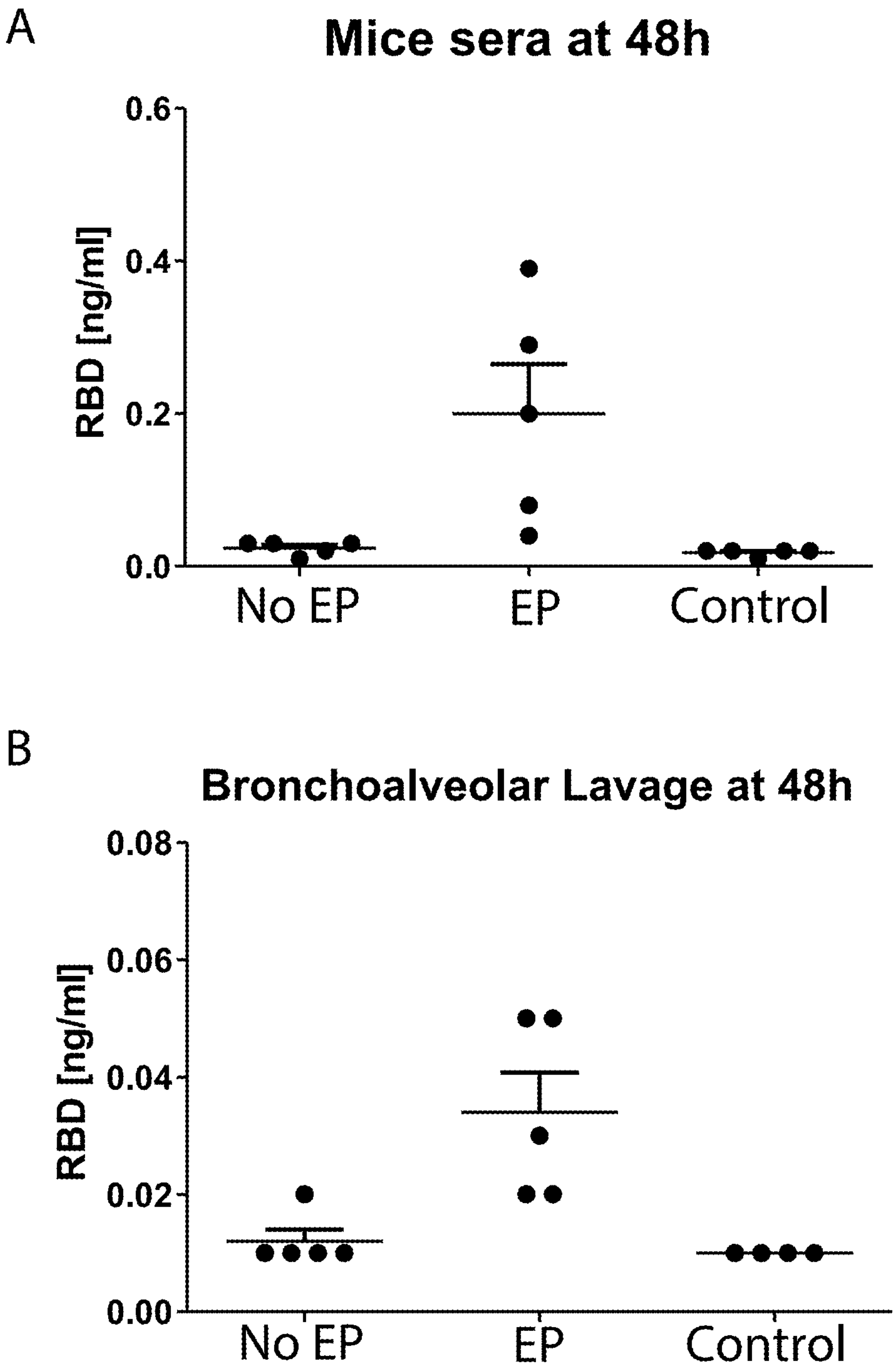
FIG. 29 shows an ELISA assay for the capture and detection of the RBD protein in the samples of mice. Panels A and B show the amount of RBD protein present in the serum and in the BALs at 48 hours, respectively. The group 1-5 (No EP) received only an injection of 50 g of COVID-eVax without electroporation; the group 6-10 (EP) received electroporation whereas the group 11-15 had no treatment (Control).

Finally, the signal emission was assessed with a Tecan microplate reader at a wavelength of 450 nm. The RBD present in the samples was compared with a reference curve in which graduated doses of purified RBD were included in the same experiment. A schematic representation of the assay is shown below:

FIG. 29 shows the presence of the protein in serum (panel A) and in BALs (Panel B) in the group of mice vaccinated with pTK1A-SpikeA (COVID-eVax) with and without electroporation.

This experiment demonstrates that in the absence of antibodies, which take a longer time to develop, the RBD protein is secreted very efficiently also in vivo and reaches the lungs.

In order to assess the amount of RBD in circulation that is sufficient to compete with ACE2, a competitive ELISA assay was set up. In the assay the ELISA 96-well plates are functionalised with the purified recombinant protein (RBD-6His) at a concentration of 1 μg/ml, diluted in 1×PBS in a volume of 50 μl/well. After an incubation of about 16 hours (O.N.) at 4° C., the plate is washed 3 times with washing buffer (1×PBS, 0.05% Tween) and blocked with 100 μl/well of a solution of 3% BSA in washing buffer. After 1 hour of incubation at room temperature, the blocking buffer is eliminated and the plate can be stored for several weeks at −20° C. In order to verify the binding competition between the RBD and human ACE-2, the sera and BALs of the vaccinated mice are diluted in a solution of 1% BSA/1×PBS/0.05% Tween which further contains an amount of 1 μg/ml of the purified recombinant ACE2-hFc protein. Incubation takes place overnight at 4° C. The next morning the plate is washed 3 times and incubated with an anti-HUMAN IgG-specific secondary antibody conjugated with alkaline phosphatase (50 μl/well diluted in BSA 1%). After 1 hour of incubation at room temperature the plate is washed 3 times and 50 μl well of alkaline phosphatase-specific substrate are added to every well. Incubation takes place at room temperature and, finally, the absorbance is read with an ELISA plate reader at λ=405 nm.

Figure 30:
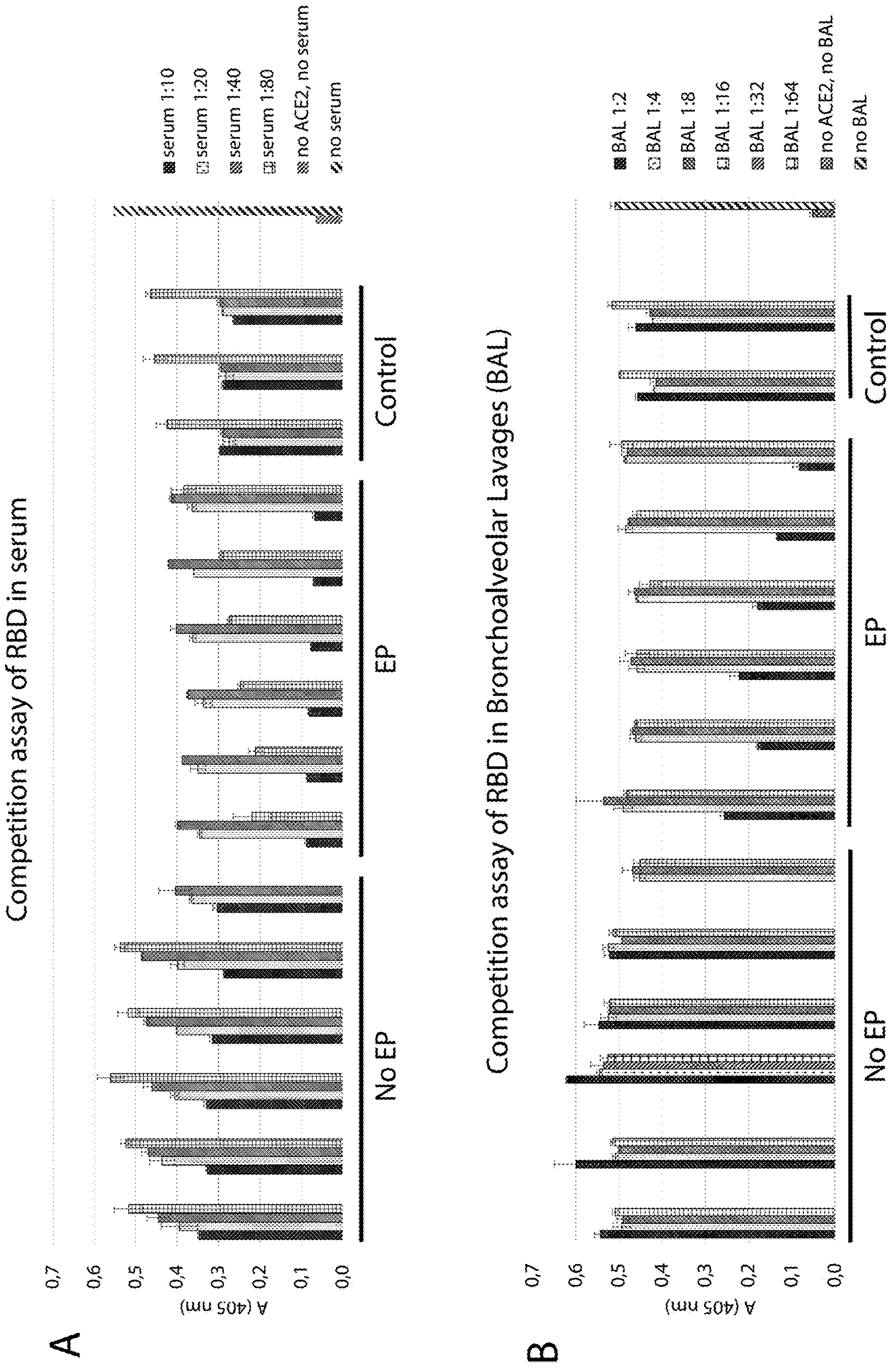
FIG. 30 shows an assay of competition with ACE2 for the samples of mice. A) Competition of the serum; B) competition of the BALs.

The sera and the BALs tested in the assay were analysed beforehand to verify the absence of antibodies that could interfere with binding between the RBD in the samples or in the plate and the recombinant ACE2. The results of the experiment (FIG. 30) show that at lower dilutions (1:10 for the serum and 1:2 for the BALs) the RBD protein present in the animal samples is effectively capable of competing with ACE2.

Figure 31:
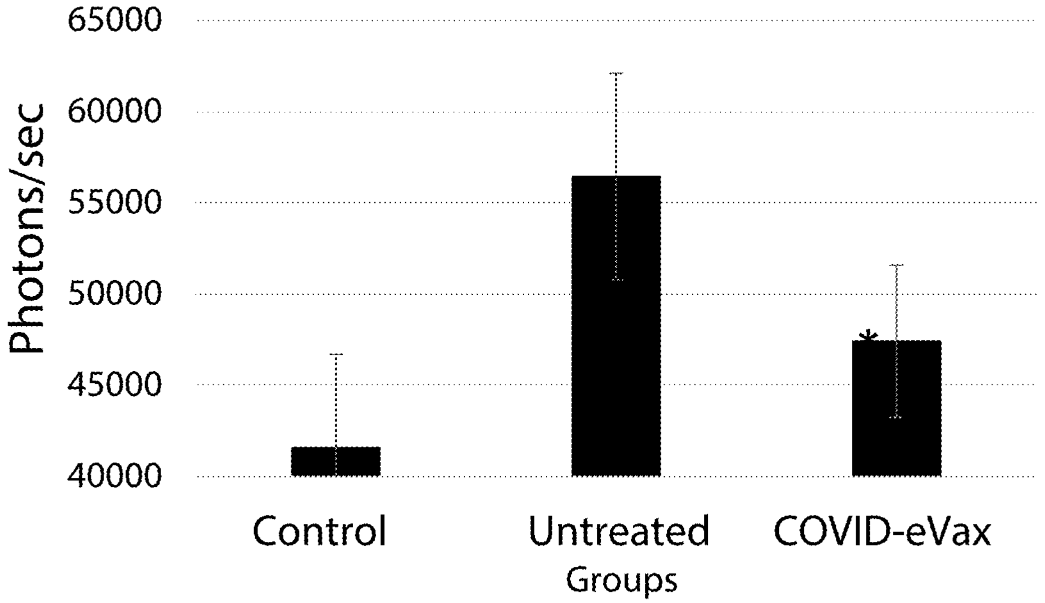
FIG. 31 shows that at 3 days COVID-eVax limits the infection with a pseudovirus, based on lentivirus technology, which expresses the SARS-CoV-2 spike protein. The asterisk indicates the statistical significance between the untreated group and the group treated with COVID-eVax ($p=0.038$).

In order to verify the ability of the RBD protein secreted following treatment with COVID-eVax, a model was set up in which mice transgenic for the human ACE2 receptor (K18-hACE2, Jackson Laboratories) and thus susceptible of infection with SARS-CoV-2 were electroporated with 50 g of COVID-eVax using the electrical conditions described previously. After 3 days, a lentivirus having the coronavirus spike protein on its surface (pseudotyped virus) and capable of expressing luciferase was injected into the nose of the mice at a dose of $1\times10^5$ transducing particles. After 48 hours, luciferin, that is, the enzymatic substrate of luciferase, was administered to the animals. Whereas a luminescence signal, measured by means of the IVIS200 system, with an average signal of about 5.6×10^5 p/s, was observed in the upper airways of untreated animals, the group treated with COVID-eVax gave a lower signal and comparable with that of the control group, showing that the secreted RBD is effectively capable of competing with the virus itself and limiting its entry into the airways (FIG. 31).

Example 18. Vaccines Against the Variants of SARS-CoV-2

Unlike other RNA viruses such as HIV, SARS-CoV-2 has a low mutation rate, but considering the high number of infected observed in this pandemic, it is reasonable to expect a selection of variants resistant to the immune response of patients. A second source of variants is due to the spread of the virus also in farmed animals such as mink. New mutations originating in mink were found in occupationally exposed patients. Lastly, a recent study, in which viral variants resistant to the immune response of hyperimmune patients were selected in vitro, demonstrated that the mechanism for evading the selective pressure imposed by human antibodies takes place through specific deletions and mutations. These circumstances justify the planning, starting from today, of second generation vaccines capable of intercepting the evolutionary trajectories of the spike protein in order to be ready to supply these vaccines to the population should these variants prevail over the circulating quasispecies.

To this end the Applicant, in collaboration with the Regina Elena Institute in Rome, generated Covid miner, a portal capable of highlighting these evolutionary phenomena by monitoring the trend of mutations in SARS-CoV-2 over time (Massacci et al. 2021). Among the mutations that are particularly relevant for the vaccine we have the British variant (deletion 69-70, deletion 144, amino acid changes: N501Y, A570D, D614G, P681H, T7161, S982A, D1118H) characterised by the N501Y mutation in the RBD, as well as the South African variant, which contains two other mutations in the RBD, E484K and K417N.

Figure 32:
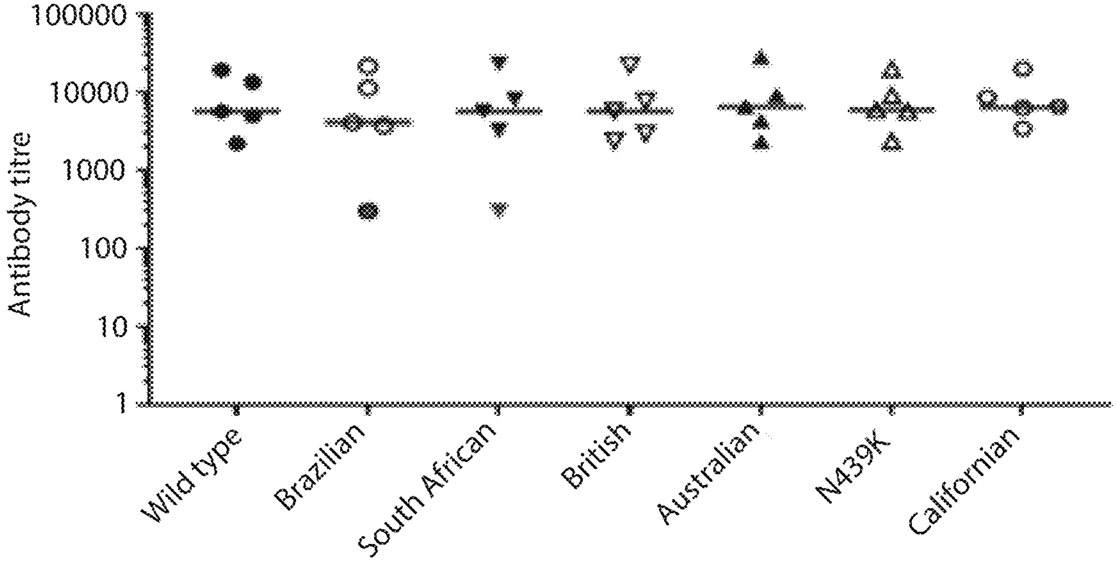
FIG. 32 shows the cross-reactivity of the COVID-eVax sera with the RBD portion of the spike protein of the variants of concern (VOCs). The antibody titre was calculated by ELISA.

In a first set of experiments it was desired to verify the ability of the COVID-eVax vaccine to recognise the RBD portion of the spike protein of the British (N501Y), South African (K417N, E484K, N501Y), Brazilian (K417T, E484K, N501Y), Australian (S477N), N439K (which is resistant to the immune response induced by vaccines) and Californian (L452R) variants. All of the proteins were produced in the Applicant's laboratories. Groups of C57Bl/6 mice were vaccinated with COVID-eVax at a dose of 5 μg/animal at days 0 and 28, and then a blood sample was taken 2 weeks later. An ELISA assay at various dilutions was then performed, enabling a calculation of the antibody titre. As shown in FIG. 32, all of the sera were capable of recognising the proteins of the variants very well.

In a second group of experiments, a group of rats was vaccinated with COVID-eVax at a dose of 400 μg/animal at days 0 and 14, and then a blood sample was taken 2 weeks later. A neutralisation assay was performed with lentivirus expressing the spike protein (pseudotyped virus) of the variants of concern (G614, British, South African and Brazilian), using serial dilutions of the sera. Surprisingly, all the sera of the animals were capable of neutralising in an equivalent manner, including the South African and Brazilian variants, whereas the sera of human subjects vaccinated with a vaccine based on messenger RNA (Pfizer/BioNTech) started off from a neutralising titre about 10 times lower and lost the neutralising capacity against variants to a significant degree (3-6 times). The data are shown below in table 5.

TABLE 5

| | G614 | British | South African | Brazilian |
|---|---|---|---|---|
| Rats vaccinated with COVIDeVax | | | | |
| #1 | 9453 | 3939 | 6395 | 8520 |
| #2 | 9406 | 7730 | 4369 | 3862 |
| #3 | 22173 | 16361 | 18508 | 19669 |
| #4 | 9406 | 10444 | 10720 | 13146 |
| #5 | 8478 | 9969 | 10283 | 8922 |
| Mean | 11783 | 9689 | 10055 | 10824 |
| Standard Deviation | 5822 | 4529 | 5424 | 5938 |

TABLE 5-continued

| | G614 | British | South African | Brazilian |
|---|---|---|---|---|
| Human subjects vaccinated with mRNA | | | | |
| #A | 856 | 286 | 252 | NF |
| #B | 1466 | 502 | 206 | NF |
| #C | 1576 | 545 | 200 | NF |
| Mean | 1299 | 444 | 219 | |
| Standard Deviation | 388 | 139 | 28 | |

The Applicant also conducted studies on vaccines according to the present invention in which optimised nucleotide sequences of the variants of SARS-CoV-2 were used. Table 6 shows the optimised sequences encoding for the RBD of the SARS-CoV-2 variants and the associated amino acid sequences of the RBD.

TABLE 6

| variant | Optimised nucleotide sequence encoding for RBD | RBD protein sequence |
|---|---|---|
| British | AGGGTGCAGCCAACCG<br>AGTCTATCGTGCGCTTT<br>CCTAATATCACAAACCT<br>GTGCCCATTTGGCGAG<br>GTGTTCAACGCAACCAG<br>GTTCGCAAGCGTGTACG<br>CATGGAATAGGAAGCGC<br>ATCTCTAACTGCGTGGC<br>CGACTATAGCGTGCTGT<br>ACAACTCCGCCTCTTTC<br>AGCACCTTTAAGTGCTA<br>TGGCGTGTCCCCCACAA<br>AGCTGAATGACCTGTGC<br>TTTACCAACGTGTACGC<br>CGATTCTTTCGTGATCA<br>GGGGCGACGAGGTGCG<br>CCAGATCGCACCTGGAC<br>AGACAGGCAAGATCGC<br>CGACTACAATTATAAGC<br>TGCCAGACGATTTCACC<br>GGCTGCGTGATCGCCT<br>GGAACAGCAACAATCTG<br>GATTCCAAAGTGGGCG<br>GCAACTACAATTATCTG<br>TACCGGCTGTTTAGAAA<br>GAGCAATCTGAAGCCCT<br>TCGAGAGGGACATCTCT<br>ACAGAAATCTACCAGGC<br>CGGCAGCACCCCTTGC<br>AATGGCGTGGAGGGCT<br>TTAACTGTTATTTOCCAC<br>TGCAGTCCTACGGCTTC<br>CAGCCCACATACGGCGT<br>GGGCTATCAGCCTTACC<br>GCGTGGTGGTGCTGAG<br>CTTTGAGCTGCTGCACG<br>CACCAGCAACAGTGTGC<br>GGACCCAAGAAGTCCAC<br>CAATCTGGTGAAGAACA<br>AGTGCGTGAACTTC<br>(SEQ ID NO: 14) | RVQPTESIVRFPNITNLC<br>PFGEVFNATRFASVYA<br>WNRKRISNCVADYSVLY<br>NSASFSTFKCYGVSPTK<br>LNDLCFTNVYADSFVIR<br>GDEVRQIAPGQTGKIAD<br>YNYKLPDDFTGCVIAWN<br>SNNLDSKVGGNYNYLY<br>RLFRKSNLKPFERDISTE<br>IYQAGSTPCNGVEGFNC<br>YFPLQSYGFQPTYGVG<br>YQPYRVVVLSFELLHAP<br>ATVCGPKKSTNLVKNKC<br>VNF<br>(SEQ ID NO: 22) |
| South African | AGGGTGCAGCCAACCG<br>AGTCTATCGTGCGCTTT<br>CCTAATATCACAAACCT<br>GTGCCCATTTGGCGAG<br>GTGTTCAACGCAACCAG<br>GTTCGCAAGCGTGTACG<br>CATGGAATAGGAAGCGC<br>ATCTCTAACTGCGTGGC<br>CGACTATAGCGTGCTGT | RVQPTESIVRFPNITNLC<br>PFGEVFNATRFASVYA<br>WNRKRISNCVADYSVLY<br>NSASFSTFKCYGVSPTK<br>LNDLCFTNVYADSFVIR<br>GDEVRQIAPGQTGNIAD<br>YNYKLPDDFTGCVIAWN<br>SNNLDSKVGGNYNYLY<br>RLFRKSNLKPFERDISTE |

TABLE 6-continued

| variant | Optimised nucleotide sequence encoding for RBD | RBD protein sequence |
|---|---|---|
| | ACAACTCCGCCTCTTTC AGCACCTTTAAGTGCTA TGGCGTGTCCCCCACAA AGCTGAATGACCTGTGC TTTACCAACGTGTACGC CGATTCTTTCGTGATCA GGGGCGACGAGGTGCG CCAGATCGCACCTGGAC AGACAGGCAATATCGCC GACTACAATTATAAGCT GCCAGACGATTTCACCG GCTGCGTGATCGCCTG GAACAGCAACAATCTGG ATTCCAAAGTGGGCGGC AACTACAATTATCTGTAC CGGCTGTTTAGAAAGAG CAATCTGAAGCCCTTCG AGAGGGACATCTCTACA GAAATCTACCAGGCCGG CAGCACCCCTTGCAATG GCGTGAAGGGCTTTAAC TGTTATTTCCCACTGCA GTCCTACGGCTTCCAGC CCACATACGGCGTGGG CTATCAGCCTTACCGCG TGGTGGTGCTGAGCTTT GAGCTGCTGCACGCAC CAGCAACAGTGTGCGG ACCCAAGAAGTCCACCA ATCTGGTGAAGAACAAG TGCGTGAACTTC (SEQ ID NO: 15) | IYQAGSTPCNGVKGFNC YFPLQSYGFQPTYGVG YQPYRVVVLSFELLHAP ATVCGPKKSTNLVKNKC VNF (SEQ ID NO: 23) |
| Brazilian | AGGGTGCAGCCAACCG AGTCTATCGTGCGCTTT CCTAATATCACAAACCT GTGCCCATTTGGCGAG GTGTTCAACGCAACCAG GTTCGCAAGCGTGTACG CATGGAATAGGAAGCGC ATCTCTAACTGCGTGGC CGACTATAGCGTGCTGT ACAACTCCGCCTCTTTC AGCACCTTTAAGTGCTA TGGCGTGTCCCCCACAA AGCTGAATGACCTGTGC TTTACCAACGTGTACGC CGATTCTTTCGTGATCA GGGGCGACGAGGTGCG CCAGATCGCACCTGGAC AGACAGGCACAATCGCC GACTACAATTATAAGCT GCCAGACGATTTCACCG GCTGCGTGATCGCCTG GAACAGCAACAATCTGG ATTCCAAAGTGGGCGGC AACTACAATTATCTGTAC CGGCTGTTTAGAAAGAG CAATCTGAAGCCCTTCG AGAGGGACATCTCTACA GAAATCTACCAGGCCGG CAGCACCCCTTGCAATG GCGTGAAGGGCTTTAAC TGTTATTTCCCACTGCA GTCCTACGGCTTCCAGC CCACATACGGCGTGGG CTATCAGCCTTACCGCG TGGTGGTGCTGAGCTTT GAGCTGCTGCACGCAC CAGCAACAGTGTGCGG ACCCAAGAAGTCCACCA ATCTGGTGAAGAACAAG TGCGTGAACTTC (SEQ ID NO: 21) | RVQPTESIVRFPNITNLC PFGEVFNATRFASVYA WNRKRISNCVADYSVLY NSASFSTFKCYGVSPTK LNDLCFTNVYADSFVIR GDEVRQIAPGQTGTIAD YNYKLPDDFTGCVIAWN SNNLDSKVGGNYNYLY RLFRKSNLKPFERDISTE IYQAGSTPCNGVKGFNC YFPLQSYGFQPTYGVG YQPYRVVVLSFELLHAP ATVCGPKKSTNLVKNKC VNF (SEQ ID NO: 24) |

Shown below is the portion of the sequence of the "COVID-eVax" vaccine which comprises the TPA secretion leader sequence (SEQ ID NO:16, not in bold) fused to the optimised RBD nucleotide sequence (SEQ ID NO:14, in bold) of the British variant by means of the restriction site PacI of sequence TTAATTAAG (underlined) and in which TAA at the end of the portion is a stop codon:

(SEQ ID NO: 25)

ATGGATGCAATGAAGAGAGGGCTCTGCTGTGTGCTGCTGCTG

TGTGGAGCAGTCTTCGTTTCGCCCAGCTTAATTAAGAGGGTGCAGCC

AACCGAGTCTATCGTGCGCTTTCCTAATATCACAAACCTGTGCCCAT

TTGGCGAGGTGTTCAACGCAACCAGGTTCGCAAGCGTGTACGCATG

GAATAGGAAGCGCATCTCTAACTGCGTGGCCGACTATAGCGTGCTG

TACAACTCCGCCTCTTTCAGCACCTTTAAGTGCTATGGCGTGTCCCC

CACAAAGCTGAATGACCTGTGCTTTACCAACGTGTACGCCGATTCTT

TCGTGATCAGGGGCGACGAGGTGCGCCAGATCGCACCTGGACAGA

CAGGCAAGATCGCCGACTACAATTATAAGCTGCCAGACGATTTCAC

CGGCTGCGTGATCGCCTGGAACAGCAACAATCTGGATTCCAAAGTG

GGCGGCAACTACAATTATCTGTACCGGCTGTTTAGAAAGAGCAATC

TGAAGCCCTTCGAGAGGGACATCTCTACAGAAATCTACCAGGCCGG

CAGCACCCCTTGCAATGGCGTGGAGGGCTTTAACTGTTATTTCCCA

CTGCAGTCCTACGGCTTCCAGCCCACATACGGCGTGGGCTATCAGC

CTTACCGCGTGGTGGTGCTGAGCTTTGAGCTGCTGCACGCACCAGC

AACAGTGTGCGGACCCAAGAAGTCCACCAATCTGGTGAAGAACAA

GTGCGTGAACTTCTAA

Shown below is the portion of the sequence of the "COVID-eVax" vaccine which comprises the TPA secretion leader sequence (SEQ ID NO:16, not in bold) fused to the optimised RBD nucleotide sequence (SEQ ID NO:15, in bold) of the South African variant by means of the restriction site PacI of sequence TTAATTAAG (underlined) and in which TAA at the end of the portion is a stop codon:

(SEQ ID NO: 26)

ATGGATGCAATGAAGAGAGGGCTCTGCTGTGTGCTGCTGCTG

TGTGGAGCAGTCTTCGTTTCGCCCAGCTTAATTAAGAGGGTGCAGCC

AACCGAGTCTATCGTGCGCTTTCCTAATATCACAAACCTGTGCCCAT

TTGGCGAGGTGTTCAACGCAACCAGGTTCGCAAGCGTGTACGCATG

GAATAGGAAGCGCATCTCTAACTGCGTGGCCGACTATAGCGTGCTG

TACAACTCCGCCTCTTTCAGCACCTTTAAGTGCTATGGCGTGTCCCC

CACAAAGCTGAATGACCTGTGCTTTACCAACGTGTACGCCGATTCTT

TCGTGATCAGGGGCGACGAGGTGCGCCAGATCGCACCTGGACAGA

CAGGCAATATCGCCGACTACAATTATAAGCTGCCAGACGATTTCAC

CGGCTGCGTGATCGCCTGGAACAGCAACAATCTGGATTCCAAAGTG

GGCGGCAACTACAATTATCTGTACCGGCTGTTTAGAAAGAGCAATC

TGAAGCCCTTCGAGAGGGACATCTCTACAGAAATCTACCAGGCCGG

-continued

CAGCACCCCTTGCAATGGCGTGAAGGGCTTTAACTGTTATTTCCCAC

TGCAGTCCTACGGCTTCCAGCCCACATACGGCGTGGGCTATCAGCC

TTACCGCGTGGTGGTGCTGAGCTTTGAGCTGCTGCACGCACCAGCA

ACAGTGTGCGGACCCAAGAAGTCCACCAATCTGGTGAAGAACAAG

TGCGTGAACTTCTAA

Shown below is the portion of the sequence of the "COVID-eVax" vaccine which comprises the TPA secretion leader sequence (SEQ ID NO:16, not in bold) fused to the optimised RBD nucleotide sequence (SEQ ID NO:21, in bold) of the Brazilian variant by means of the restriction site PacI of sequence TTAATTAAG (underlined) and in which TAA at the end of the portion is a stop codon:

(SEQ ID NO: 27)

ATGGATGCAATGAAGAGAGGGCTCTGCTGTGTGCTGCTGCTG

TGTGGAGCAGTCTTCGTTTCGCCCAGCTTAATTAAGAGGGTGCAGCC

AACCGAGTCTATCGTGCGCTTTCCTAATATCACAAACCTGTGCCCAT

TTGGCGAGGTGTTCAACGCAACCAGGTTCGCAAGCGTGTACGCATG

GAATAGGAAGCGCATCTCTAACTGCGTGGCCGACTATAGCGTGCTG

TACAACTCCGCCTCTTTCAGCACCTTTAAGTGCTATGGCGTGTCCCC

CACAAAGCTGAATGACCTGTGCTTTACCAACGTGTACGCCGATTCTT

TCGTGATCAGGGGCGACGAGGTGCGCCAGATCGCACCTGGACAGA

CAGGCACAATCGCCGACTACAATTATAAGCTGCCAGACGATTTCAC

CGGCTGCGTGATCGCCTGGAACAGCAACAATCTGGATTCCAAAGTG

GGCGGCAACTACAATTATCTGTACCGGCTGTTTAGAAAGAGCAATC

TGAAGCCCTTCGAGAGGGACATCTCTACAGAAATCTACCAGGCCGG

CAGCACCCCTTGCAATGGCGTGAAGGGCTTTAACTGTTATTTCCCAC

TGCAGTCCTACGGCTTCCAGCCCACATACGGCGTGGGCTATCAGCC

TTACCGCGTGGTGGTGCTGAGCTTTGAGCTGCTGCACGCACCAGCA

ACAGTGTGCGGACCCAAGAAGTCCACCAATCTGGTGAAGAACAAG

TGCGTGAACTTCTAA

Figure 33:
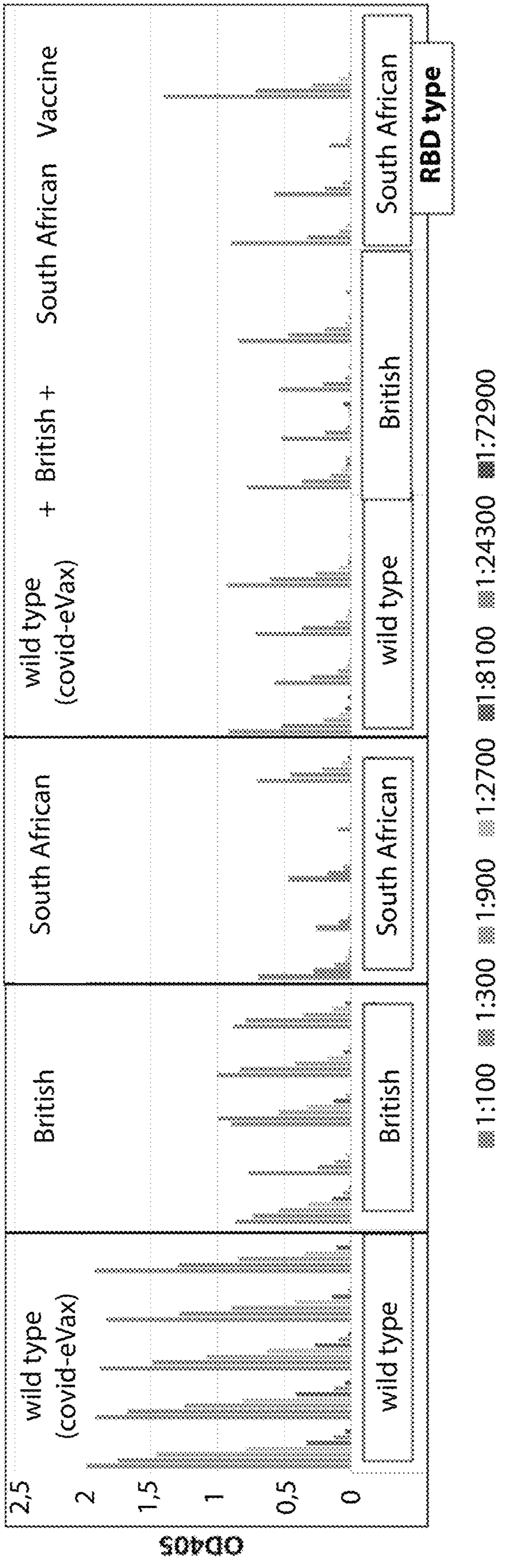
FIG. 33 shows an ELISA assay performed 14 days after the injection of sera of animals vaccinated with the original version of COVID-eVax, the version thereof encoding the RBD of the British variant, the South African variant or with a mixture of the three plasmids. For each group of mice the OD405 values refer, from left to right, to the following sera dilutions: 1:100, 1:300, 1:900, 1:2700, 1:8100, 1:24300, 1:72900.

In order to verify whether the vaccines of the COVID-eVax type are capable of recognising the RBD version of various variants, an experiment was performed where groups of C57Bl/6 mice were vaccinated with 10 g of COVID-eVax (original, Wuhan), the British variant, the South African variant and a mixture of the three plasmids (3.3 g per animal). The electrical conditions were the same as used previously. After 14 days a blood sample was taken and the serum was tested by means of an ELISA assay using both the original RBD protein, and the British or South African variant thereof. As indicated in FIG. 33, and as expected, the wild-type COVID-eVax induces an excellent recognition of the protein of the Wuhan SARS-CoV.2, the British version of COVID-eVax effectively recognises the British RBD variant, the COVID-eVax South African version effectively recognises the South African RBD variant and the mixture of the three plasmids effectively recognises the 3 versions of the RBD portion. These experiments demonstrate that it is possible to generate the COVID-eVax versions against the variants and obtain a specific immune response already two weeks after the first injection.

Example 19. Experiment to Test Effectiveness on K18-hACE-2 Transgenic Mice

In order to assess the effectiveness of COVID-eVax in a model susceptible of SARS-CoV-2 infection, K18-hACE2 transgenic mice (Jackson Laboratories) were used at the San Raffaele Hospital in Milan, which possesses an authorised BSL3 facility suitable for the study. All of the experimental procedures on the animals were approved by the Animal Institutional Committee of the San Raffaele Scientific Institute and all the infection work was carried out in the specially designed BSL-3 workspaces. Thirteen 8-week-old male mice were randomised into 2 groups of 5 and 8 mice each. Group 1 (5 control mice) was injected intramuscularly with a diluent. Group 2 received intramuscular injections of the DNA vaccine on day 0 and day 21 at a dose of 10 μg/mouse. The vaccination protocol consisted in an injection in a quadriceps muscle (right on day 0 and left on day 21) of the COVID-eVax plasmid formulated in phosphate buffered saline (PBS) at a concentration of 0.2 mg/ml. DNA-EP was performed with an electroporator of the IGEA Cliniporator type, using a needle electrode (electrode N-10-4B). For the DNA-EP into the muscle, the following electrical conditions were applied: low voltage, 4 pulses of 5 msec, each at 40V, with an interval of 5 msec between each of them.

All the mice were infected with $10^5$ TCID50 of SARS-CoV-2 on day 35. The hCoV-19/Italy/LOM-UniSR-1/2020 (EPI_ISL_413489) isolate of SARS-CoV-2 was obtained from the Microbiology and Virology Unit of the San Raffaele Scientific Institute. The studies on the isolation of the virus were conducted on Vero E6 cells, cultured at 37° C., 5% $CO_2$ in a complete medium (DMEM supplemented with 10% FBS, 1% penicillin plus streptomycin, 1% L-glutamine).

Figure 34:
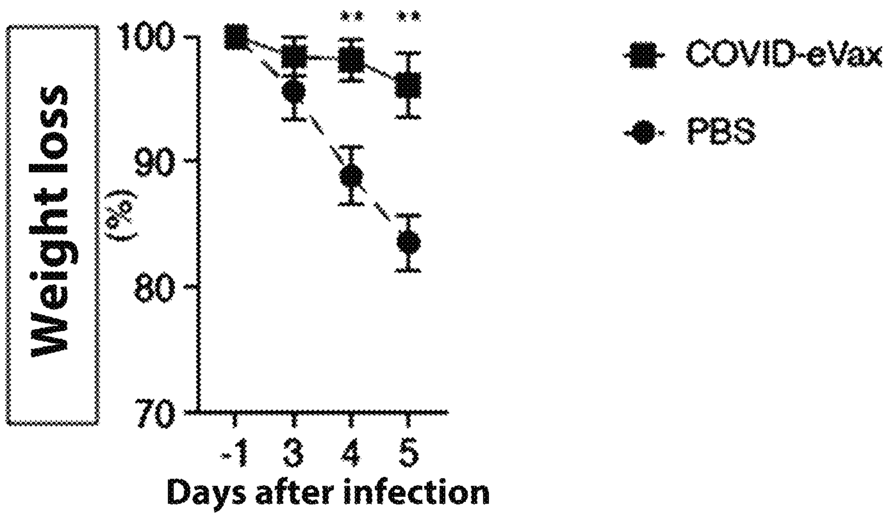
FIG. 34 shows a weight loss in K18-hACE2 transgenic mice treated with COVID-eVax compared to the controls (PBS).

The body weight was measured on days 0, 7, 14, 21, 28, 32, 35, 39 and 42. As shown in FIG. 34, the infected mice undergo major weight loss, which arrives at about 18% of the original weight. This effect was not observed in the group vaccinated with COVID-eVax.

Figure 35:
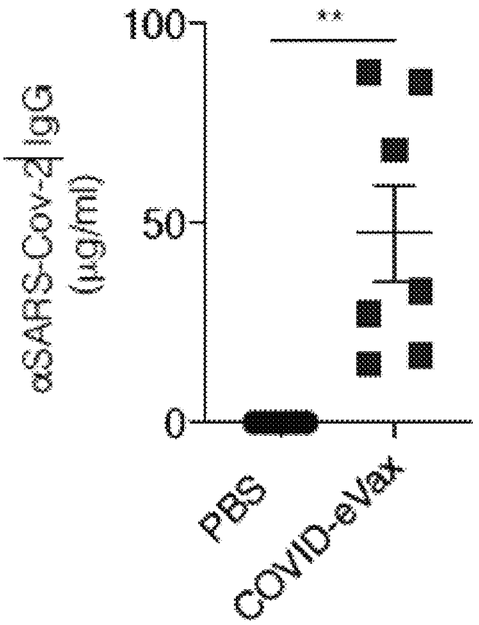
FIG. 35 shows the anti-RBD antibodies developed in K18-hACE2 mice.

During the experiment, about 100 μl of whole blood was collected at each point in time (days 0, 7, 14, 21, 28, 35 and 42) and serum samples were prepared and stored at −80° C. The serum samples were analysed for anti-SARS-CoV-2 antibodies by means of ELISA assays. FIG. 35 shows a high quantity of specific antibodies against the spike protein measured the day before the challenge with SARS-CoV-2.

Figure 36:
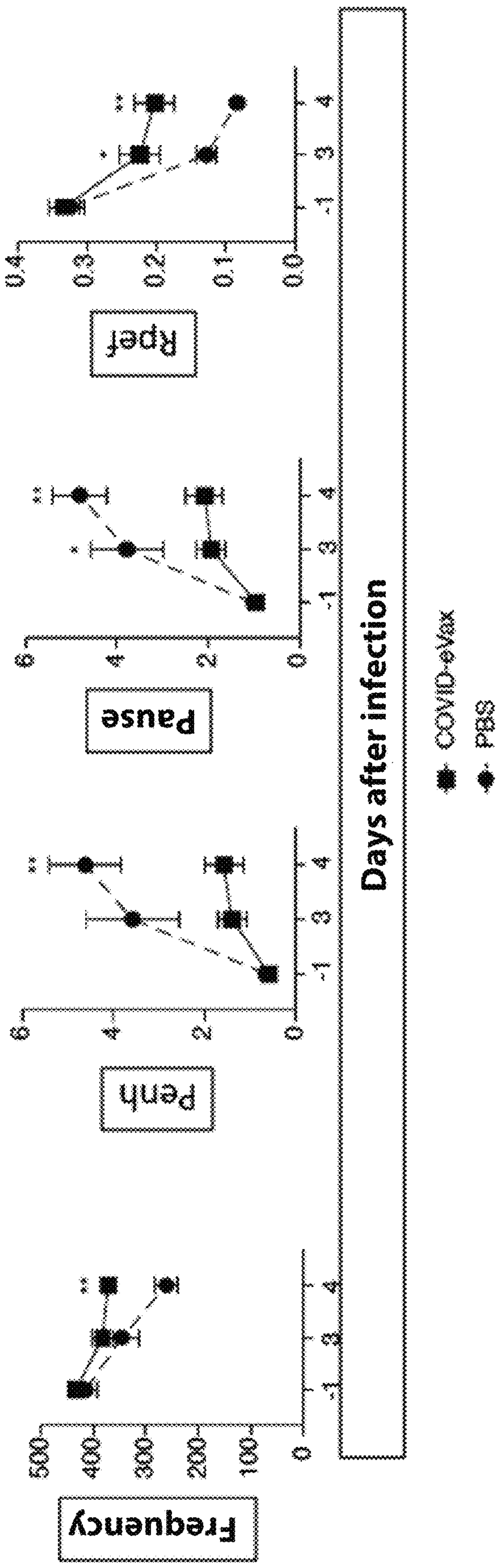
FIG. 36 shows the results of whole-body plethysmography evaluating lung function based on Frequency, Penh, Pause and Rpef. The respiratory values calculated were averaged over the data collection period of 20 minutes; the data are means±SEM.

Whole-body plethysmography was performed on days 34 and 36, using a WBP chamber (DSI Buxco, DSI). The first mice were allowed to acclimatise inside the chamber for 10 minutes; then the respiratory parameters were acquired for 15 minutes using FinePointe software. As shown in FIG. 36, all of the parameters measured by the machine for the mice vaccinated with COVID-eVax were significantly better than those of the group treated with simple PBS. These experiments demonstrate an important clinical impact of COVID-eVax on animals infected with SARS-CoV2.

Five days after the SARS-CoV-2 infection, all of the mice were sacrificed and the lungs, liver, spleen, brain and BALs were collected for analysis by flow cytometry and for detection of SARS-CoV-2 RNA by qPCR. The lung was perfused through the right ventricle with PBS at the time of the autopsy and the brain was removed from the skull. The lung tissue was digested in RPMI 1640 containing 3.2 mg/ml of collagenase IV (Sigma, #C5138) and 25 U/ml of DNAse I (Sigma, #D4263) for 30 minutes at 37° C. The brain was digested in RPMI 1640 containing 1 mg/ml of collagenase D (Sigma, #11088866001) for 30 minutes at 37° C. The homogenised lung and brain were filtered through a 70 μm nylon mesh to obtain a single cellular suspension. The cells were resuspended in a 36% percoll solution (Sigma #P4937) and centrifuged for 20 minutes at 2000 rpm (slight acceleration and low braking). The remaining red blood cells were removed with ACK lysis buffer.

Figure 37:
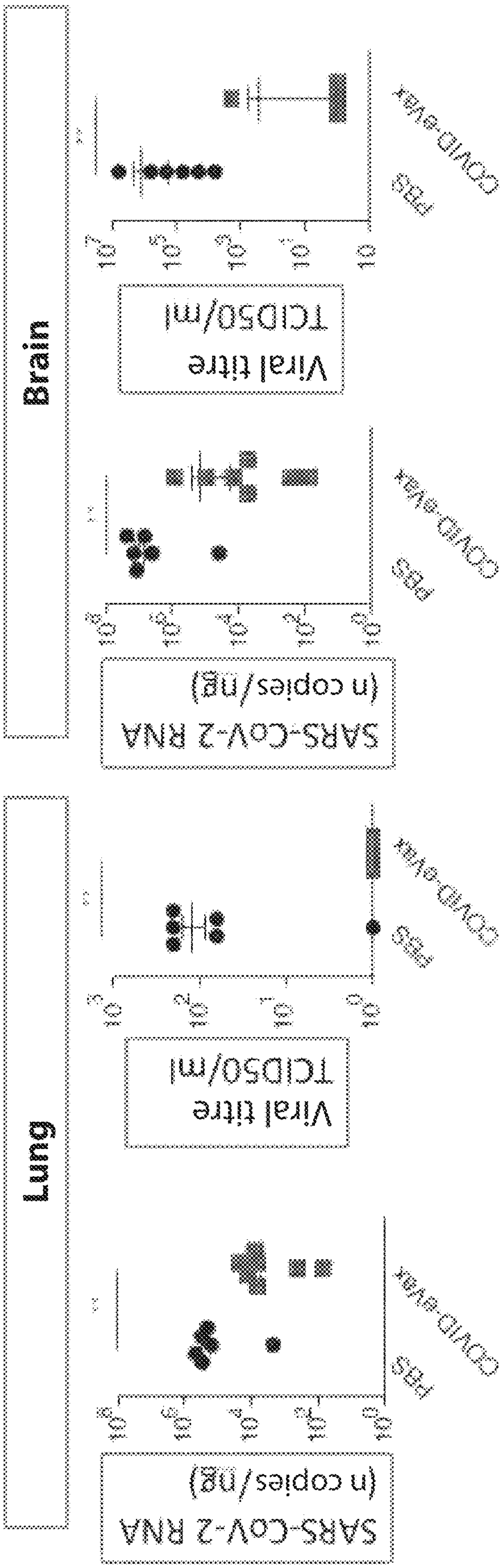
FIG. 37 shows the quantification of viral RNA by quantitative reverse-transcription PCR (RT-qPCR) 5 days after lung and brain infection in K18-hACE2 mice. Every dot represents an animal. For the virus titre in the lung and brain, the supernatants of the cell culture were collected 72 hours after infection and titred at TCID50/ml.

For the analysis of the intracellular cytokine production ex vivo, 1 mg/ml of brefeldin A (Sigma #B7651) were included in the digestion buffer. All the flow cytometry stains of molecules expressed on the surface and intracellularly were performed as described (Benechet A. et al., Nature 2019). Briefly, the cells were stimulated for 4 hours at 37° C. with peptide 15-mers overlapped by 11 amino acids (5 μg/ml) which covered the receptor-binding-domain (RBD) of SARS-CoV-2. Cell viability was assessed by staining with Viobility™ 405/520 fixable dye (Miltenyi, Cat #130-109-814). The results of the RT-PCR and viral titre are shown in FIG. 37. The vaccinated mice showed a significant reduction in the viral genomes measured by RT-qPCR and an absence of viable virus in the lungs and brain (with only one exception).

Figure 38:
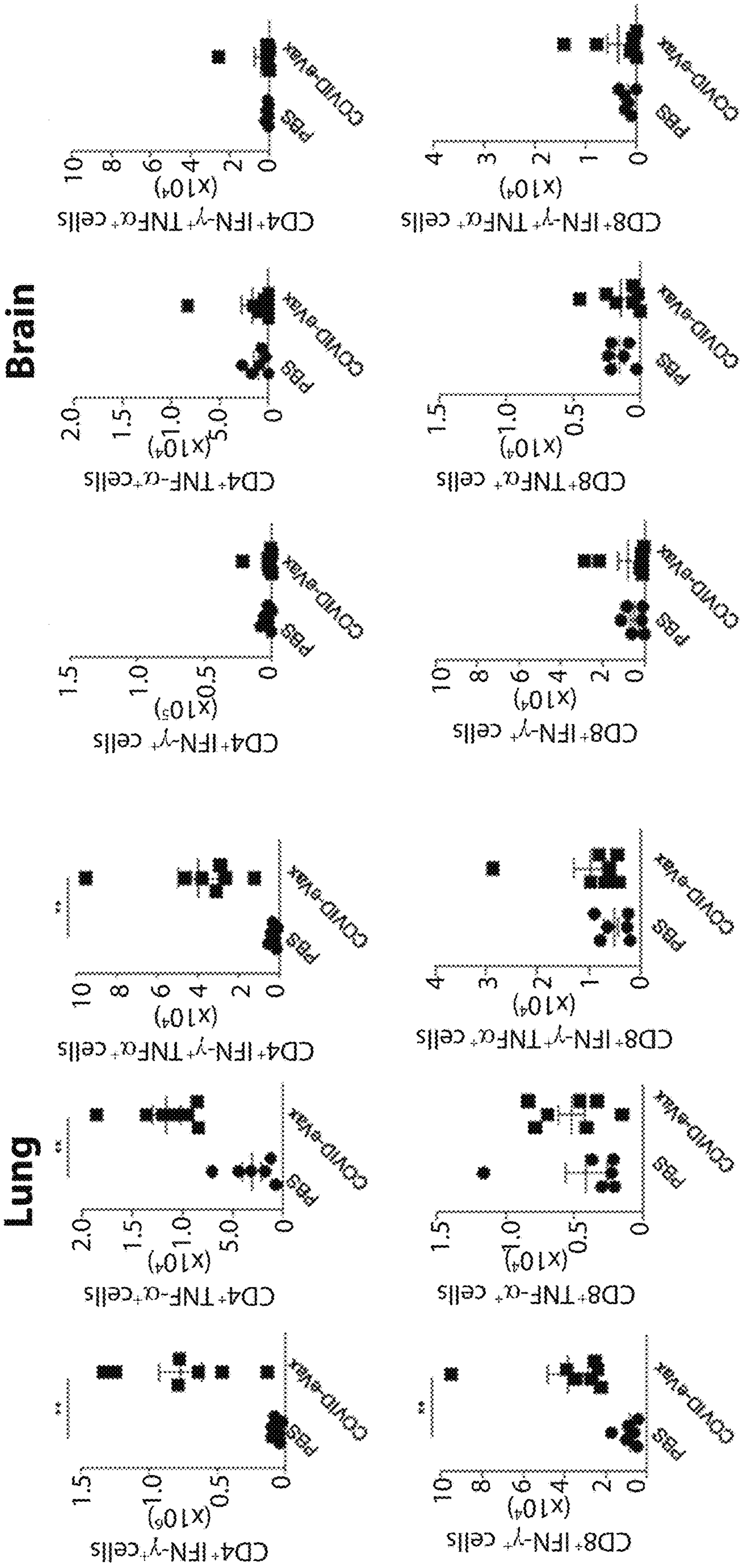
FIG. 38 shows absolute numbers of IFN-γ, TNFα or both which produce in CD4+ and CD8+ cells in the lung and brain of K18-hACE2 mice indicated five days after SARS-Cov-2 infection. * p value<0.05, ** p value<0.01 Mann-Whitney test.

As regards the characterisation of T cells in the organs, a substantial infiltration of types CD4+ and CD8+ was observed in the lungs, suggesting that cells were brought in from the periphery. This phenomenon was not observed in the brain, probably due to the presence of the blood-brain barrier (FIG. 38).

Figure 39:
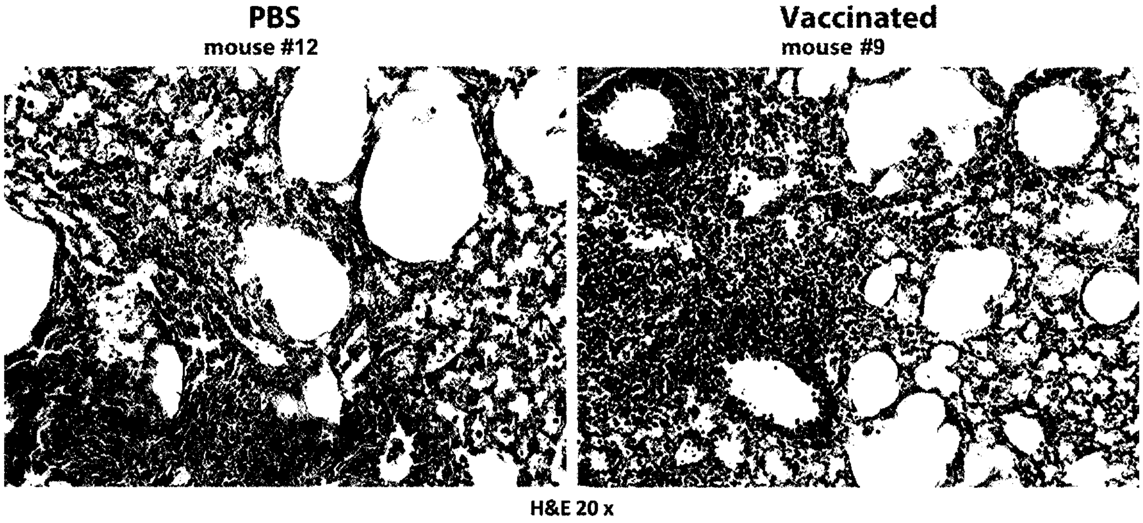
FIG. 39 shows an example of haematoxylin and eosin staining of lung tissue isolated from K18-hACE2 mice, controls or vaccinated with COVID-eVax.

The lung histology (H&E) of mice confirmed the cytometry data, showing a substantial lymphocyte infiltration in the vaccinated animals and a monocyte/macrophage infiltration in the control animals, induced by the inflammation due to the infection (FIG. 39).

Example 20. Treatment of Mice with a Vaccine Against SARS-CoV-2 Based on Amplicons Obtained by PCR Genetic vaccines typically consist of DNA plasmid vectors or viral vectors, encoding for the antigen of interest, which can be inoculated by simple intradermal or intramuscular injection, thus inducing an immune response against the antigen itself. In fact, after inoculation of the vector into the host, a transfection of the cells residing in the treated tissue (muscle cells, fibroblasts and dendritic cells) occurs, thus inducing the production of the antigen of interest inside the transfected cell. The antigenic protein thus produced is then expressed in the context of the major histocompatibility complex (MHC) to induce the immune response in the host. The expression of the gene encoding the antigen can be controlled by a strong promoter expressed in the cells of mammals, such as CMV, usually used in a bacterial DNA plasmid. Another fundamental element of every DNA plasmid is the gene that imparts resistance to antibiotics, which enables the selective growth solely of the bacteria that possess it for the purpose of amplifying the vector itself. Unfortunately, in recent decades the excessive and often inappropriate use of antibiotics, in both human and veterinary medicine, as well as in husbandry and agriculture, has led to the spread of these substances in the environment on a large scale and consequently the development of multi-resistant pathogenic bacterial strains with clear, worrying repercussions on the health of the population. Therefore, regulatory agencies have declared that the presence, in the plasmid vector, of the gene for resistance to antibiotics may constitute a potential threat in clinical therapy, considering the potential transfer of resistance to the endogenous microbial fauna of the host receiving the plasmid. Consequently, for the purpose of a clinical use of plasmid DNA in clinical practice, the use of antibiotics in the process of bacterial fermentation entails costly processes of removal during purification of the plasmid to prevent contamination of the final product with residual antibiotics. In fact, the plasmid should not contain any region encoding proteins other than that of the antigen of interest, considering the potential expression in mammal cells. Therefore, considering the constant recommendations of the regulatory agencies to avoid the use of genes selective for the resistance to antibiotics in clinical practice, in recent years alternative selection strategies for the production of plasmid DNA have been proposed. According to the present invention, an innovative strategy, as an alternative to plasmid DNA, is represented by the use of amplicons, i.e. DNA or RNA fragments generated by PCR, in immunotherapy against SARS-CoV-2. In order to verify whether an amplicon induces an immune response comparable to that of plasmid DNA, 5 amplicons were designed:

4868 bp amplicon comprising the Full-Length Spike;
2561 bp amplicon comprising Spike A;
3470 bp amplicon comprising Spike B;
3890 bp amplicon comprising Spike C;
3220 bp amplicon comprising Igk-RBD-Fc.

The amplicons comprise an hCMV promoter, intron A from hCMV, the sequences specified and described previously and a bGH terminator which were synthesised by PCR using the plasmid DNAs as a template. The 10 ml PCR used the following reagents: 1 ml of buffer 10×, 0.4 ml of MgCl2 (50 mM), 0.25 ml of dNTP (40 mM), 0.4 ml of Biolase, 50 μL of each forward and reverse primer (100 μM), 500 ng of template, 2.5 ml of betaine (4 M), water for PCR q.s. to 10 ml. The PCR was performed using the following program: initial denaturation at 95° C. for 60 seconds, then 28~30 cycles of PCR in two steps, at 94° C. for 20 seconds, 70° C. for 6 minutes; final extension at 72° C. for 8 minutes. The final yield was 50 mg/L.

For all the expression vectors of the amplicons, the yield and dimensions were confirmed by means of an Agilent Bioanalyzer 2100. All the expression vectors of the amplicons were purified by precipitation with ethanol and anion exchange columns to remove the unincorporated primers, dNTP and small DNA fragments.

Figure 40:
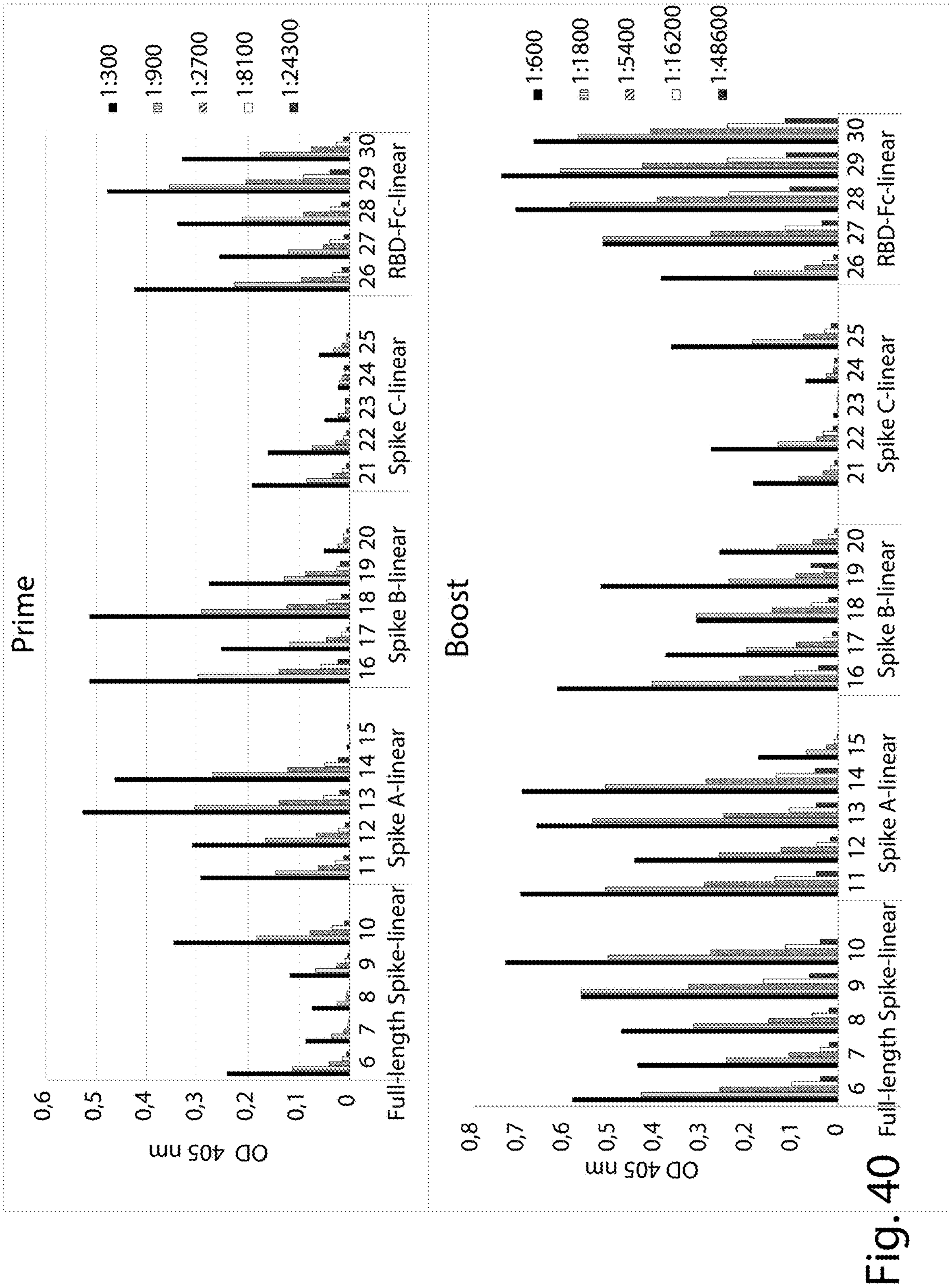
FIG. 40 shows an ELISA assay performed on sera of BALB/c mice vaccinated with the linear versions (Full-Length Spike, Spike A, Spike B, Spike C, RBD-Fc linear) of the DNA vaccines amplified by PCR.

The vaccination protocol consisted in an injection in both quadriceps muscles of female Balb/C mice aged 6-7 weeks (Envigo, the Netherlands); the DNA of the amplicons was formulated in phosphate buffered saline (PBS) at a concentration of 0.2 mg/ml. DNA-EP was performed with an electroporator of the IGEA Cliniporator type, using a needle electrode (electrode A-15-4B). For the DNA-EP in the muscle, the following electric conditions were applied: low voltage, 8 pulses of 20 msec, each at 110V, 8 Hz, with an interval of 120 msec between each of them. The vaccination was repeated on day 21 and an ELISA assay was performed on the serum of the animal on day 21 (after the prime dose) and on day 35 (after the booster). The results in FIG. 40 show a strong induction of IgG type antibodies already after the first vaccination, which increases considerably after the second one. The amplicons encoding Spike A and RBD-Fc generated the largest immune response.

Figure 41:
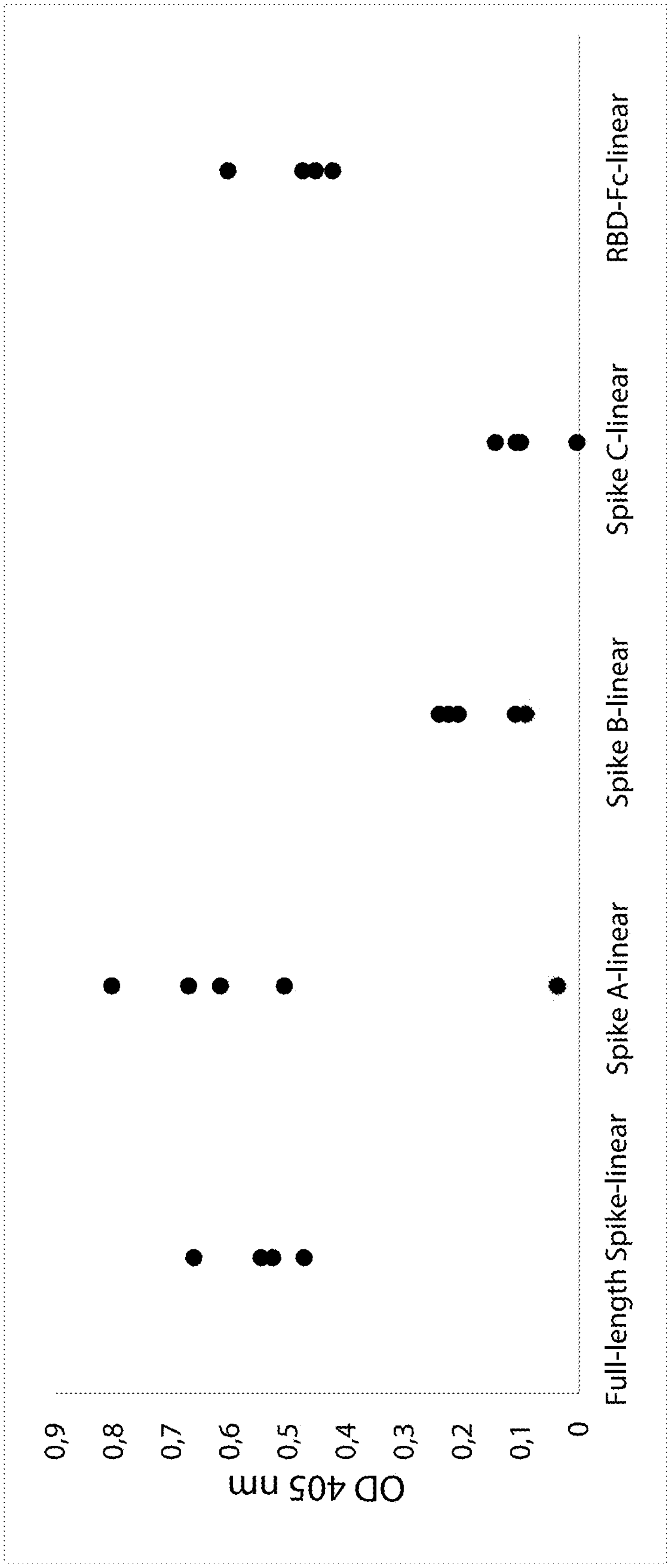
FIG. 41 shows an ELISA assay performed on bronchoalveolar lavages of BALB/c mice vaccinated with the Full-Length, Spike A, Spike B, Spike C and RBD-Fc amplicons.

In order to verify the presence of antibodies in bronchoalveolar lavage fluids (BALs), an ELISA was performed and showed the greater presence of antibodies after treatment with the Spike A and Spike FL candidates, as shown in FIG. 41.

Figure 42:
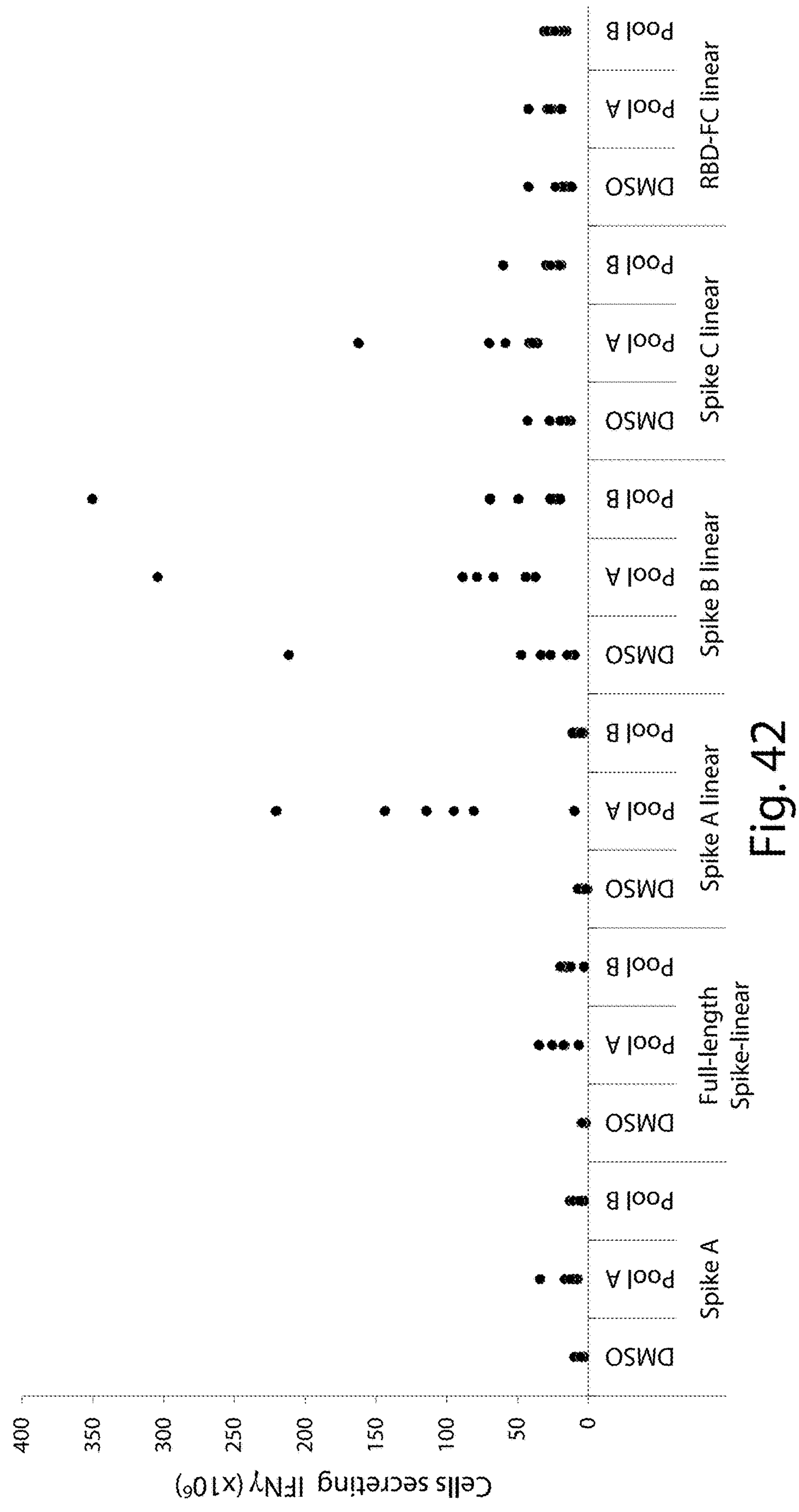
FIG. 42 shows an ELISPOT assay performed with splenocytes of BALB/c mice vaccinated with the linear versions of Full-Length Spike, Spike A, Spike B, Spike C and RBD-Fc.

FIG. 42 shows the entity of the cell-mediated response induced by the amplicons and measured by ELISPOT for IFNγ. The group with the largest response proved to be Spike A-lin.

The experiments conducted with amplicons thus also suggest that the version containing the monomeric RBD (Spike A) as COVID-eVax is the most immunogenic.

Example 21. Treatment of Cats with a Vaccine Against SARS-CoV-2 Based on Amplicons Obtained Via PCR As reported by the American Veterinary Medical Association, in addition to human-to-human transmission, human-to-animal transmission of SARS-CoV-2 has been observed in several wild animals and domestic animals, especially in cats. With animal models as an invaluable tool in the study of infectious diseases, combined with the fact that the intermediate animal source of SARS-CoV-2 is still unknown, researchers have demonstrated that cats and ferrets are permissive to SARS-CoV-2 (Shi J. et al., Science 2020). These results make cats an appropriate animal model for assessing the vaccine against COVID-19 with monitoring for SARS-CoV-2 in cats in addition to elimination of COVID-19 in human beings. Further studies are needed to assess the possible transmission from cats to humans.

A clinical study authorised by the American USDA was conducted to assess the immunogenicity of the Spike A amplicon in cats. The tibial muscle is injected with 1 mg of DNA, followed by electroporation performed with a Vet-ePorator™, a device produced by IGEA (Carpi, Modena, Italia), using the same electrical conditions as described previously.

The primary objective of the study was to assess the safety, reactogenicity and immunogenicity of the candidate linear COVID-19 DNA vaccine in healthy adult cats. The secondary objectives were to assess long-term post-administration safety and the duration of the immune response of the candidate linear COVID-19 DNA vaccine in healthy adult cats. Cats with a negative result in the molecular test for SARS-CoV-2, aged 1 to 15 years, in good health, without any clinical pathologies or underlying attenuating pathologies (CBC, Chimica, UA, Covid 19 test) were evaluated as candidates for the study. The animals received 1 mg of DNA in 0.5 ml, single vaccination (prime) by means of electroporation at days 1 and 25-32 (total of 2 vaccinations).

After a brief anaesthetic protocol (dexdomitor/propofol/isoflourane), 0.5 mL intramuscular injections of the vaccine were immediately followed by co-localised intramuscular electroporation (Vet-ePorator) in the tibial region of each muscle of the rear limb as described previously.

Figure 43:
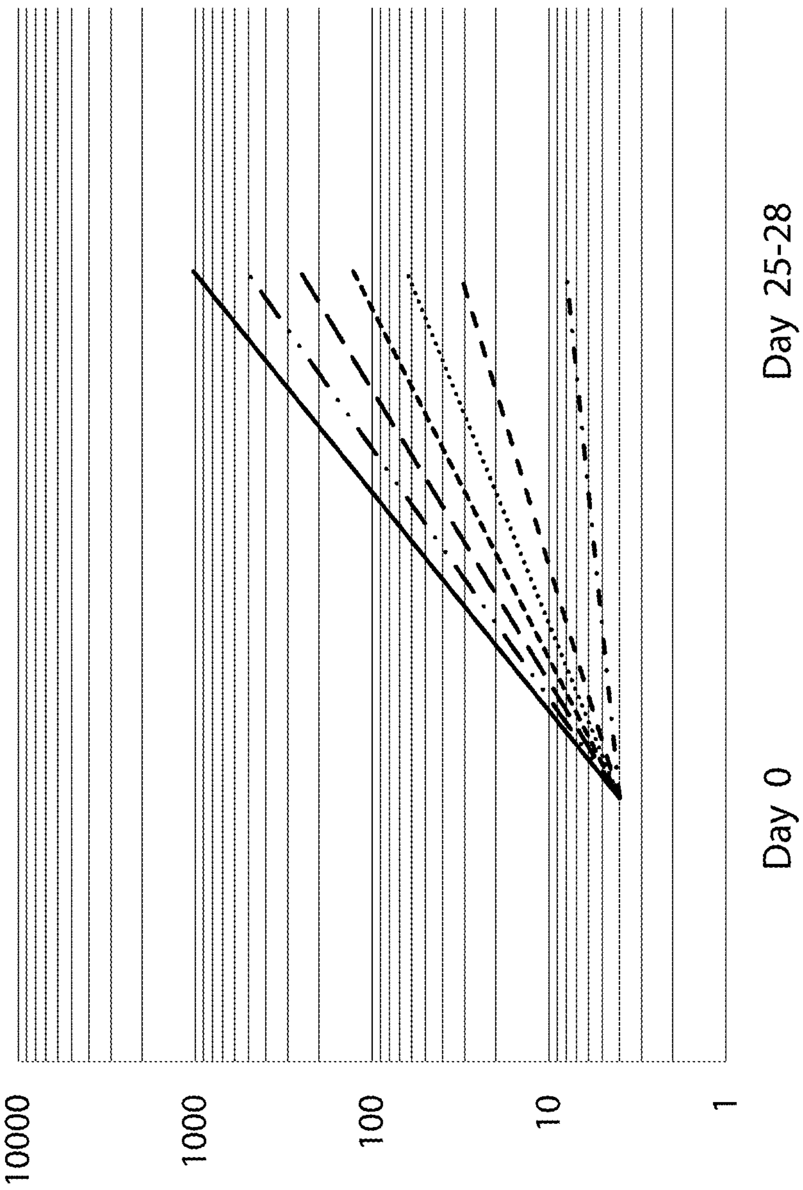
FIG. 43 shows the neutralising antibodies present in 11 cats vaccinated with a single injection of the Spike A amplicon at a dose of 1 mg. The geometric mean of the group is 1:112.

The study included 11 cats. At day 25-28 a neutralisation assay was performed on the serum of the animals with SARS-CoV-2 as described previously. The results (FIG. 43) show the seroconversion in all the vaccinated cats with a titre ranging from 1:32 to 1:1024, with a geometric mean of 1:112.

These results demonstrate that a vaccine having the RBD (Spike A) as a basis functions as a plasmid DNA but also as an amplicon produced via PCR.

REFERENCES

1. Cheng, V. C., Lau, S. K., Woo, P. C. & Yuen, K. Y. Severe acute respiratory syndrome coronavirus as an agent of emerging and reemerging infection. Clin. Microbiol. Rev. 20, 660-694 (2007).

2. Chan, J. F. et al. Middle East respiratory syndrome coronavirus: another zoonotic betacoronavirus causing SARS-like disease. Clin. Microbiol. Rev. 28, 465-522 (2015).
3. Zumla A, Chan J F, Azhar El, Hui D S, Yuen K Y., Coronaviruses—drug discovery and therapeutic options. Nat Rev Drug Discov. 15(5):327-47 (2016). 12.
4. Forni, D., Cagliani, R., Clerici, M. & Sironi, M. Molecular evolution of human coronavirus genomes. Trends Microbiol. 25, 35-48 (2017).
5. Buchholz U J, Bukreyev A, Yang L, Lamirande E W, Murphy B R, Subbarao K, Collins P L, Contributions of the structural proteins of severe acute respiratory syndrome coronavirus to protective immunity. Proc. Natl. Acad. Sci. U.S.A., (26):9804-9809 (2004)
6. Song W, Gui M, Wang X, Xiang Y. Cryo-EM structure of the SARS coronavirus spike glycoprotein in complex with its host cell receptor ACE2. PLoS Pathog. 2018 Aug. 13; 14(8):e1007236. doi: 10.1371/journal.ppat.1007236. eCollection 2018 August
7. Traggiai E1, Becker S, Subbarao K, Kolesnikova L, Uematsu Y, Gismondo M R, Murphy B R, Rappuoli R, Lanzavecchia A: An efficient method to make human monoclonal antibodies from memory B cells: potent neutralization of SARS coronavirus. Nat Med. 2004 August; 10(8):871-5. Epub 2004 Jul. 11.
8. Corti D, Zhao J, Pedotti M, Simonelli L, Agnihothram S, Fett C, Fernandez-Rodriguez B, Foglierini M, Agatic G, Vanzetta F, Gopal R, Langrish C J, Barrett N A, Sallusto F, Baric R S, Varani L, Zambon M, Perlman S, Lanzavecchia: A Prophylactic and postexposure efficacy of a potent human monoclonal antibody against MERS coronavirus. Proc Natl Acad Sci USA. 112(33):10473-8 (2015)
9. Walls A C, Park Y J, Tortorici M A, Wall A, McGuire A T, Veesler D. Structure, Function, and Antigenicity of the SARS-CoV-2 Spike Glycoprotein. Cell. 2020 Mar. 6. pii: S0092-8674(20)30262-2. doi: 10.1016/j.cell.2020.02.058.
10. Walls A C, Xiong X, Park Y J, Tortorici M A, Snijder J, Quispe J, Cameroni E, Gopal R, Dai M, Lanzavecchia A, Zambon M, Rey F A, Corti D, Veesler D. Unexpected Receptor Functional Mimicry Elucidates Activation of Coronavirus Fusion. Cell. 2019 Feb. 21; 176(5):1026-1039.e15. doi: 10.1016/j.cell.2018.12.028. Epub 2019 Jan. 31.
11. Tai W, He L, Zhang X1, Pu J, Voronin D, Jiang S, Zhou Y, Du L. Characterization of the receptor-binding domain (RBD) of 2019 novel coronavirus: implication for development of RBD protein as a viral attachment inhibitor and vaccine. Cell Mol Immunol. 2020 Mar. 19. doi: 10.1038/s41423-020-0400-4.
12. Hangping Y, Xiangyun L, Qiong C, Kaijin X, Yu C, Linfang C, Fumin L, Zhigang W, Haibo W, Changzhong J, Min Z, Nanping W, Chao J, Lanjuan L. Patient-derived mutations impact pathogenicity of SARS-CoV-2 doi: 10.1101/2020.04.14.20060160
13. Shi J, Wen Z, Zhong G, et al. Susceptibility of ferrets, cats, dogs, and other domesticated animals to SARS-coronavirus 2 [published online ahead of print, 2020 Apr. 8]. Science. 2020; eabb7015. doi:10.1126/science.abb7015
14. J. M. van den Brand, B. L. Haagmans, L. Leijten, D. van Riel, B. E. E. Martina, A. D. M. E. Osterhaus, T. Kuiken, Pathology of experimental SARS coronavirus infection in cats and ferrets. Vet. Pathol. 45, 551-562 (2008).
15. B. E. Martina, B. L. Haagmans, T. Kuiken, R. A. M. Fouchier, G. F. Rimmelzwaan, G. Van Amerongen, J. S. M. Peiris, W. Lim, A. D. M. E. Osterhaus, Virology: SARS virus infection of cats and ferrets. Nature 425, 915 (2003). doi:10.1038/425915apmid:14586458
16. Q. Zhang et al., bioRxiv (2020). doi:10.1101/2020.04.01.021196
17. Yang Z Y, Werner H C, Kong W P, Leung K, Traggiai E, Lanzavecchia A, Nabel G J. Evasion of antibody neutralization in emerging severe acute respiratory syndrome coronaviruses. Proc Natl Acad Sci USA. 2005 Jan. 18; 102(3):797-801.
18. Wan Y, Shang J, Sun S, Tai W, Chen J, Geng Q, He L, Chen Y, Wu J, Shi Z, Zhou Y, Du L, Li F. Molecular Mechanism for Antibody-Dependent Enhancement of Coronavirus Entry. J Virol. 2020 Feb. 14; 94(5). pii: e02015-19. doi: 10.1128/JVI.02015-19. Print 2020 Feb. 14.
19. Tetro J A. Is COVID-19 receiving ADE from other coronaviruses? Microbes Infect. 2020 March; 22(2):72-73. doi: 10.1016/j.micinf.2020.02.006. Epub 2020 Feb. 22.
20. Yip M S, Leung N H, Cheung C Y, Li P H, Lee H H, Dae¨ron M, Peiris J S, Bruzzone R, Jaume M Antibody-dependent infection of human macrophages by severe acute respiratory syndrome coronavirus. Virol J 11:82 (2014)
21. Tseng C T, Sbrana E, Iwata-Yoshikawa N, Newman P C, Garron T, Atmar R L, Peters C J, Couch R B. Immunization with SARS coronavirus vaccines leads to pulmonary immunopathology on challenge with the SARS virus. PLoS One. 2012; 7(4):e35421.
22. Wang S F, Tseng S P, Yen C H, Yang J Y, Tsao C H, Shen C W, Chen K H, Liu F T, Liu W T, Chen Y M, Huang J C1. Antibody-dependent SARS coronavirus infection is mediated by antibodies against spike proteins. Biochem Biophys Res Commun. 2014 Aug. 22; 451(2):208-14. doi: 10.1016/j.bbrc.2014.07.090. Epub 2014 Jul. 26.
23. Luo F, Liao F L, Wang H, Tang H B, Yang Z Q, Hou W. Evaluation of Antibody-Dependent Enhancement of SARS-CoV Infection in Rhesus Macaques Immunized with an Inactivated SARS-CoV Vaccine. Virol Sin. 2018 April; 33(2):201-204. doi: 10.1007/si2250-018-0009-2. Epub 2018 Mar. 14.
24. Andre, F. & Mir, L. M. DNA electrotransfer: its principles and an updated review of its therapeutic applications. *Gene Ther.* 11 Suppl 1, S33-42 (2004).
25. Gothelf, A. & Gehl, J. What you always needed to know about electroporation based DNA vaccines. *Hum. Vaccin. Immunother.* 8, 1694-1702 (2012).
26. Neumann, E., Kakorin, S. & Toensing, K. Fundamentals of electroporative delivery of drugs and genes. *Bioelectrochem. Bioenerg.* 48, 3-16 (1999).
27. Lurquin, P. F. Gene transfer by electroporation. *Mol. Biotechnol.* 7, 5-35 (1997).
28. Mathiesen, I. Electropermeabilization of skeletal muscle enhances gene transfer in vivo. *Gene Ther.* 6, 508-514 (1999).
29. Mir, L. M. et al. High-efficiency gene transfer into skeletal muscle mediated by electric pulses. *Proc. Natl. Acad. Sci. U.S.A.* 96, 4262-4267 (1999).
30. Rizzuto, G. et al. Gene electrotransfer results in a high-level transduction of rat skeletal muscle and corrects anemia of renal failure. *Hum. Gene Ther.* 11, 1891-1900 (2000).
31. Fattori, E., La Monica, N., Ciliberto, G. & Toniatti, C. Electro-gene-transfer: a new approach for muscle gene delivery. *Somat. Cell Mol. Genet.* 27, 75-83 (2002).

32. Durieux, A.-C., Bonnefoy, R., Busso, T. & Freyssenet, D. In vivo gene electrotransfer into skeletal muscle: effects of plasmid DNA on the occurrence and extent of muscle damage. *J. Gene Med.* 6, 809-816 (2004).
33. Diaz, C. M. et al. Phase 1 studies of the safety and immunogenicity of electroporated HER2/CEA DNA vaccine followed by adenoviral boost immunization in patients with solid tumors. *J. Transl. Med.* 11, 62 (2013).
34. Aurisicchio, L., Fridman, A., Mauro, D. et al. Safety, tolerability and immunogenicity of V934/V935 hTERT vaccination in cancer patients with selected solid tumors: a phase I study. J Transl Med 18, 39 (2020). doi:10.1186/si2967-020-02228-9
35. Li F, Li W, Farzan M, Harrison S C. Structure of SARS coronavirus spike receptor-binding domain complexed with receptor. Science. 2005; 309(5742):1864-1868. doi: 10.1126/science.1116480
36. Walls A C, Xiong X, Park Y J, Tortorici M A, Snijder J, Quispe J, Cameroni E, Gopal R, Dai M, Lanzavecchia A, Zambon M, Rey F A. Unexpected Receptor Functional Mimicry Elucidates Activation of Coronavirus Fusion Cell. 2019 Feb. 21; 176(5):1026-1039

The invention claimed is:

1. A polynucleotide encoding an amino acid sequence, an expression vector comprising said polynucleotide, or a pharmaceutical composition comprising said polynucleotide or expression vector in combination with one or more excipients and/or adjuvants, wherein the polynucleotide comprises or consists of a sequence selected from:

SEQ ID NO:1 fused to the C-terminal of the tissue plasminogen activator (TPA) secretion leader sequence, said sequence SEQ ID NO:1 encoding an amino acid sequence consisting of the receptor binding domain (RBD) domain of the S1 subunit of the spike protein of the SARS-CoV-2 virus or of variants thereof;

a sequence having a percent identity greater than or equal to 80% compared to sequence SEQ ID NO:1, selected from SEQ ID NO:14, SEQ ID NO:15, and SEQ ID NO:21, alone or fused to the C-terminal of the tissue plasminogen activator (TPA) secretion leader sequence;

SEQ ID NO:2, which encodes an amino acid sequence consisting of the N-terminal domain (NTD) and RBD domains of the S1 subunit of the spike protein of the SARS-CoV-2 virus;

SEQ ID NO:3, which encodes an amino acid sequence consisting of the NTD, RBD, C-terminal domain 2 (CTD2) and C-terminal domain 3 (CTD3) domains of the S1 subunit of the spike protein of the SARS-CoV-2 virus;

SEQ ID NO:5, which encodes an amino acid sequence consisting of the spike protein of the SARS-CoV-2 virus; and SEQ ID NO:4, which encodes an amino acid sequence consisting of the RBD domain of the S1 subunit of the spike protein of the SARS-CoV-2 virus, said domain being fused at the N-terminal end to the IgK leader sequence and at the C-terminal end to the Fc immunomodulating sequence.

2. A polynucleotide encoding an amino acid sequence, an expression vector comprising said polynucleotide, or a pharmaceutical composition according to claim 1, wherein said polynucleotide further comprises one or more sequences encoding one, more than one, or all of the domains selected from among N-Terminal Domain (NTD), C-Terminal Domain 2 (CDT2) and C-Terminal Domain 3 (CDT3) of the S1 subunit of the spike protein of the SARS-CoV-2 virus or of variants thereof.

3. A polynucleotide encoding an amino acid sequence, an expression vector comprising said polynucleotide, or a pharmaceutical composition according to claim 1, wherein the polynucleotide further comprises a sequence encoding a leader sequence.

4. A polynucleotide encoding an amino acid sequence, an expression vector comprising said polynucleotide, or a pharmaceutical composition according to claim 3, wherein the leader sequence is selected from the secretion leader sequence of the tissue plasminogen activator (TPA), of IgK, of growth hormone, of serum albumin, or of alkaline phosphatase.

5. A polynucleotide encoding an amino acid sequence, an expression vector comprising said polynucleotide, or a pharmaceutical composition according to claim 1, wherein the polynucleotide further comprises a sequence encoding an immunomodulating amino acid sequence.

6. The polynucleotide encoding an amino acid sequence, the expression vector comprising said polynucleotide, or the pharmaceutical composition according to claim 5, wherein said immunomodulating amino acid sequence is selected from a fragment crystallisable (Fc) region, profilin-like protein of *Toxoplasma gondii* (PFTG) or a functional fragment derived therefrom, the B subunit of the heat-labile toxin of *Escherichia coli* (LTB) or the tetanus toxin (TT).

7. A polynucleotide encoding an amino acid sequence, an expression vector comprising said polynucleotide, or a pharmaceutical composition according to claim 1, wherein the polynucleotide further comprises one or more sequences encoding one or more antigenic sequences of the SARS-CoV-2 virus other than those of the S1 subunit of the spike protein of the SARS-CoV-2 virus.

8. A polynucleotide encoding an amino acid sequence, an expression vector comprising said polynucleotide, or a pharmaceutical composition according to claim 1, wherein said expression vector is selected from the group consisting of a plasmid, a bacterial plasmid, an RNA, a replicating RNA, an amplicon obtained by PCR, and a viral vector.

9. The polynucleotide encoding an amino acid sequence, the expression vector comprising said polynucleotide, or the pharmaceutical composition according to claim 8, wherein said viral vector is selected from adenovirus, poxvirus, vaccinia virus, fowlpox, herpes virus, adeno-associated virus (AAV), alphavirus, lentivirus, lambda phage, lymphocytic choriomeningitis virus.

10. The polynucleotide encoding an amino acid sequence, the expression vector comprising said polynucleotide, or the pharmaceutical composition according to claim 8, wherein said bacterial plasmid is selected from *Listeria* sp sp and *Salmonella* sp.

11. A kit for the prevention and treatment of the disease caused by the SARS-CoV-2 virus, said kit comprising or consisting of: a) a polynucleotide encoding an amino acid sequence, an expression vector comprising said polynucleotide, or a pharmaceutical composition as defined in claim 1; and b) a system of administration by electroporation or another device for in vivo gene transduction.

12. A DNA, RNA or protein-based vaccine comprising a polynucleotide encoding an amino acid sequence, an expression vector comprising said polynucleotide, or a pharmaceutical composition according to claim 1.

* * * * *

SEQUENCE LISTING

```
<160> NUMBER OF SEQ ID NOS: 28

<210> SEQ ID NO 1
<211> LENGTH: 669
<212> TYPE: DNA
<213> ORGANISM: Artificial Sequence
<220> FEATURE:
<223> OTHER INFORMATION: nucleotide sequence encoding SARS-CoV-2 RBD

<400> SEQUENCE: 1

agggtgcagc caaccgagtc tatcgtgcgc tttcctaata tcacaaacct gtgcccattt      60

ggcgaggtgt tcaacgcaac caggttcgca agcgtgtacg catggaatag gaagcgcatc     120

tctaactgcg tggccgacta tagcgtgctg tacaactccg cctctttcag cacctttaag     180

tgctatggcg tgtcccccac aaagctgaat gacctgtgct ttaccaacgt gtacgccgat     240

tctttcgtga tcaggggcga cgaggtgcgc cagatcgcac ctggacagac aggcaagatc     300

gccgactaca attataagct gccagacgat ttcaccggct gcgtgatcgc ctggaacagc     360

aacaatctgg attccaaagt gggcggcaac tacaattatc tgtaccggct gtttagaaag     420

agcaatctga agcccttcga gagggacatc tctacagaaa tctaccaggc cggcagcacc     480

ccttgcaatg gcgtggaggg ctttaactgt tatttcccac tgcagtccta cggcttccag     540

cccacaaacg gcgtgggcta tcagccttac cgcgtggtgg tgctgagctt tgagctgctg     600

cacgcaccag caacagtgtg cggacccaag aagtccacca atctggtgaa gaacaagtgc     660

gtgaacttc                                                             669


<210> SEQ ID NO 2
<211> LENGTH: 1578
<212> TYPE: DNA
<213> ORGANISM: Artificial Sequence
<220> FEATURE:
<223> OTHER INFORMATION: nucleotide sequence encoding SARS-CoV-2 NTD and
      RBD

<400> SEQUENCE: 2

gtgaacctga ctactagaac tcagctgcct cccgcttaca ccaattcctt cacccggggc      60

gtgtactatc ctgacaaggt gtttagaagc tccgtgctgc actctacaca ggatctgttt     120

ctgccattct ttagcaacgt gacctggttc cacgccatcc acgtgagcgg caccaatggc     180

acaaagcggt tcgacaatcc cgtgctgcct tttaacgatg gcgtgtactt cgcctctacc     240

gagaagagca acatcatcag aggctggatc tttggcacca cactggactc caagacacag     300

tctctgctga tcgtgaacaa tgccaccaac gtggtcatca aggtgtgcga gttccagttt     360

tgtaatgatc ccttcctggg cgtgtactat cacaagaaca ataagagctg gatggagtcc     420

gagtttagag tgtattctag cgccaacaat tgcacatttg agtacgtgtc ccagcctttc     480
```

ctgatggacc tggagggcaa gcagggcaat ttcaagaacc tgagggagtt cgtgtttaag 540
aatatcgatg gctacttcaa aatctactct aagcacaccc ccatcaacct ggtgcgcgac 600
ctgcctcagg gcttcagcgc cctggagcca ctggtggatc tgcctatcgg catcaacatc 660
acccggtttc agacactgct ggccctgcac agaagctacc tgacacccgg cgactcctct 720
agcggatgga ccgcaggagc agcagcctac tatgtgggct atctgcagcc taggaccttc 780
ctgctgaagt acaacgagaa tggcaccatc acagacgccg tggattgcgc cctggatcct 840
ctgagcgaga caaagtgtac actgaagtcc tttaccgtgg agaagggcat ctatcagaca 900
tccaatttca gggtgcagcc aaccgagtct atcgtgcgct ttcctaatat cacaaacctg 960
tgcccatttg gcgaggtgtt caacgcaacc aggttcgcaa gcgtgtacgc atggaatagg 1020
aagcgcatct ctaactgcgt ggccgactat agcgtgctgt acaactccgc ctctttcagc 1080
acctttaagt gctatggcgt gtcccccaca aagctgaatg acctgtgctt taccaacgtg 1140
tacgccgatt ctttcgtgat caggggcgac gaggtgcgcc agatcgcacc tggacagaca 1200
ggcaagatcg ccgactacaa ttataagctg ccagacgatt tcaccggctg cgtgatcgcc 1260
tggaacagca acaatctgga ttccaaagtg ggcggcaact acaattatct gtaccggctg 1320
tttagaaaga gcaatctgaa gcccttcgag agggacatct ctacagaaat ctaccaggcc 1380
ggcagcaccc cttgcaatgg cgtggagggc tttaactgtt atttcccact gcagtcctac 1440
ggcttccagc ccacaaacgg cgtgggctat cagccttacc gcgtggtggt gctgagcttt 1500
gagctgctgc acgcaccagc aacagtgtgc ggacccaaga agtccaccaa tctggtgaag 1560
aacaagtgcg tgaacttc 1578

<210> SEQ ID NO 3
<211> LENGTH: 1998
<212> TYPE: DNA
<213> ORGANISM: Artificial Sequence
<220> FEATURE:
<223> OTHER INFORMATION: nucleotide sequence encoding SARS-CoV-2 NTD, RBD, CTD2 and CTD3

<400> SEQUENCE: 3
gtgaacctga ctactagaac tcagctgcct cccgcttaca ccaattcctt cacccggggc 60
gtgtactatc ctgacaaggt gtttagaagc tccgtgctgc actctacaca ggatctgttt 120
ctgccattct ttagcaacgt gacctggttc cacgccatcc acgtgagcgg caccaatggc 180
acaaagcggt tcgacaatcc cgtgctgcct tttaacgatg gcgtgtactt cgcctctacc 240
gagaagagca acatcatcag aggctggatc tttggcacca cactggactc caagacacag 300
tctctgctga tcgtgaacaa tgccaccaac gtggtcatca aggtgtgcga gttccagttt 360
tgtaatgatc ccttcctggg cgtgtactat cacaagaaca ataagagctg gatggagtcc 420
gagtttagag tgtattctag cgccaacaat tgcacatttg agtacgtgtc ccagcctttc 480
ctgatggacc tggagggcaa gcagggcaat ttcaagaacc tgagggagtt cgtgtttaag 540
aatatcgatg gctacttcaa aatctactct aagcacaccc ccatcaacct ggtgcgcgac 600
ctgcctcagg gcttcagcgc cctggagcca ctggtggatc tgcctatcgg catcaacatc 660
acccggtttc agacactgct ggccctgcac agaagctacc tgacacccgg cgactcctct 720
agcggatgga ccgcaggagc agcagcctac tatgtgggct atctgcagcc taggaccttc 780
ctgctgaagt acaacgagaa tggcaccatc acagacgccg tggattgcgc cctggatcct 840
ctgagcgaga caaagtgtac actgaagtcc tttaccgtgg agaagggcat ctatcagaca 900

```
tccaatttca gggtgcagcc aaccgagtct atcgtgcgct ttcctaatat cacaaacctg    960

tgcccatttg gcgaggtgtt caacgcaacc aggttcgcaa gcgtgtacgc atggaatagg   1020

aagcgcatct ctaactgcgt ggccgactat agcgtgctgt acaactccgc ctctttcagc   1080

acctttaagt gctatggcgt gtcccccaca aagctgaatg acctgtgctt taccaacgtg   1140

tacgccgatt ctttcgtgat caggggcgac gaggtgcgcc agatcgcacc tggacagaca   1200

ggcaagatcg ccgactacaa ttataagctg ccagacgatt tcaccggctg cgtgatcgcc   1260

tggaacagca acaatctgga ttccaaagtg ggcggcaact acaattatct gtaccggctg   1320

tttagaaaga gcaatctgaa gcccttcgag agggacatct ctacagaaat ctaccaggcc   1380

ggcagcaccc cttgcaatgg cgtggagggc tttaactgtt atttcccact gcagtcctac   1440

ggcttccagc ccacaaacgg cgtgggctat cagccttacc gcgtggtggt gctgagcttt   1500

gagctgctgc acgcaccagc aacagtgtgc ggacccaaga agtccaccaa tctggtgaag   1560

aacaagtgcg tgaacttcaa cttcaacggc ctgaccggaa caggcgtgct gaccgagtcc   1620

aacaagaagt tcctgccatt tcagcagttc ggcagggaca tcgcagatac cacagacgcc   1680

gtgcgcgacc cacagaccct ggagatcctg gatatcacac cctgctcttt cggcggcgtg   1740

agcgtgatca caccaggaac caatacaagc aaccaggtgg ccgtgctgta tcaggacgtg   1800

aattgtaccg aggtgcctgt ggccatccac gccgatcagc tgaccccaac atggcgggtg   1860

tacagcaccg gctccaacgt gttccagaca agagcaggat gtctgatcgg agcagagcac   1920

gtgaacaatt cctatgagtg cgacatccca atcggcgccg gcatctgtgc ctcttaccag   1980

acccagacaa actctcca                                                 1998
```

```
<210> SEQ ID NO 4
<211> LENGTH: 1413
<212> TYPE: DNA
<213> ORGANISM: Artificial Sequence
<220> FEATURE:
<223> OTHER INFORMATION: nucleotide sequence encoding IgK,  SARS-CoV-2
      RBD and Fc

<400> SEQUENCE: 4

atggagacag acacactcct gctatgggta ctgctgctct gggttccagg atccacagga     60

agggtgcagc caaccgagtc tatcgtgcgc tttcctaata tcacaaacct gtgcccattt    120

ggcgaggtgt tcaacgcaac caggttcgca agcgtgtacg catggaatag gaagcgcatc    180

tctaactgcg tggccgacta tagcgtgctg tacaactccg cctctttcag cacctttaag    240

tgctatggcg tgtcccccac aaagctgaat gacctgtgct ttaccaacgt gtacgccgat    300

tctttcgtga tcaggggcga cgaggtgcgc cagatcgcac ctggacagac aggcaagatc    360

gccgactaca attataagct gccagacgat ttcaccggct gcgtgatcgc ctggaacagc    420

aacaatctgg attccaaagt gggcggcaac tacaattatc tgtaccggct gtttagaaag    480

agcaatctga agcccttcga gagggacatc tctacagaaa tctaccaggc cggcagcacc    540

ccttgcaatg gcgtggaggg ctttaactgt tatttcccac tgcagtccta cggcttccag    600

cccacaaacg gcgtgggcta tcagccttac cgcgtggtgg tgctgagctt tgagctgctg    660

cacgcaccag caacagtgtg cggacccaag aagtccacca atctggtgaa gaacaagtgc    720

gtgaacttcg tcgacaaaac tcacacatgc ccaccgtgcc cagcacctga actcctgggg    780

ggaccgtcag tcttcctctt ccccccaaaa cccaaggaca ccctcatgat ctcccggacc    840

cctgaggtca catgcgtggt ggtggacgtg agccacgaag accctgaggt caagttcaac    900
```

```
tggtacgtgg acggcgtgga ggtgcataat gccaagacaa agccgcggga ggagcagtac    960

aacagcacgt accgtgtggt cagcgtcctc accgtcctgc accaggactg gctgaatggc   1020

aaggagtaca agtgcaaggt ctccaacaaa gccctcccag cccccatcga gaaaaccatc   1080

tccaaagcca aagggcagcc ccgagaacca caggtgtaca ccctgccccc atcccgggag   1140

gagatgacca agaaccaggt cagcctgacc tgcctggtca aaggcttcta tcccagcgac   1200

atcgccgtgg agtgggagag caatgggcag ccggagaaca actacaagac cacgcctccc   1260

gtgctggact ccgacggctc cttcttcctc tacagcaagc tcaccgtgga caagagcagg   1320

tggcagcagg ggaacgtctt ctcatgctcc gtgatgcatg aggctctgca caaccactac   1380

acgcagaaga gcctctccct gtctccgggt aaa                                1413


<210> SEQ ID NO 5
<211> LENGTH: 3843
<212> TYPE: DNA
<213> ORGANISM: Artificial Sequence
<220> FEATURE:
<223> OTHER INFORMATION: nucleotide sequence encoding SARS-CoV-2 Spike
      protein

<400> SEQUENCE: 5

gatctgccac catgtttgtc ttcctggtcc tgctgcccct ggtctcctct cagtgcgtga     60

acctgactac tagaactcag ctgcctcccg cttacaccaa ttccttcacc cggggcgtgt    120

actatcctga caaggtgttt agaagctccg tgctgcactc tacacaggat ctgtttctgc    180

cattctttag caacgtgacc tggttccacg ccatccacgt gagcggcacc aatggcacaa    240

agcggttcga caatcccgtg ctgcctttta acgatggcgt gtacttcgcc tctaccgaga    300

agagcaacat catcagaggc tggatctttg gcaccacact ggactccaag acacagtctc    360

tgctgatcgt gaacaatgcc accaacgtgg tcatcaaggt gtgcgagttc cagttttgta    420

atgatccctt cctgggcgtg tactatcaca agaacaataa gagctggatg gagtccgagt    480

ttagagtgta ttctagcgcc aacaattgca catttgagta cgtgtcccag cctttcctga    540

tggacctgga gggcaagcag ggcaatttca agaacctgag ggagttcgtg tttaagaata    600

tcgatggcta cttcaaaatc tactctaagc acacccccat caacctggtg cgcgacctgc    660

ctcagggctt cagcgccctg gagccactgg tggatctgcc tatcggcatc aacatcaccc    720

ggtttcagac actgctggcc ctgcacagaa gctacctgac acccggcgac tcctctagcg    780

gatggaccgc aggagcagca gcctactatg tgggctatct gcagcctagg accttcctgc    840

tgaagtacaa cgagaatggc accatcacag acgccgtgga ttgcgccctg gatcctctga    900

gcgagacaaa gtgtacactg aagtccttta ccgtggagaa gggcatctat cagacatcca    960

atttcagggt gcagccaacc gagtctatcg tgcgctttcc taatatcaca aacctgtgcc   1020

catttggcga ggtgttcaac gcaaccaggt tcgcaagcgt gtacgcatgg aataggaagc   1080

gcatctctaa ctgcgtggcc gactatagcg tgctgtacaa ctccgcctct ttcagcacct   1140

ttaagtgcta tggcgtgtcc cccacaaagc tgaatgacct gtgctttacc aacgtgtacg   1200

ccgattcttt cgtgatcagg ggcgacgagg tgcgccagat cgcacctgga cagacaggca   1260

agatcgccga ctacaattat aagctgccag acgatttcac cggctgcgtg atcgcctgga   1320

acagcaacaa tctggattcc aaagtgggcg gcaactacaa ttatctgtac cggctgttta   1380

gaaagagcaa tctgaagccc ttcgagaggg acatctctac agaaatctac caggccggca   1440

gcaccccttg caatggcgtg gagggcttta actgttattt cccactgcag tcctacggct   1500
```

tccagcccac aaacggcgtg ggctatcagc cttaccgcgt ggtggtgctg agctttgagc 1560
tgctgcacgc accagcaaca gtgtgcggac ccaagaagtc caccaatctg gtgaagaaca 1620
agtgcgtgaa cttcaacttc aacggcctga ccggaacagg cgtgctgacc gagtccaaca 1680
agaagttcct gccatttcag cagttcggca gggacatcgc agataccaca gacgccgtgc 1740
gcgacccaca gaccctggag atcctggata tcacaccctg ctctttcggc ggcgtgagcg 1800
tgatcacacc aggaaccaat acaagcaacc aggtggccgt gctgtatcag gacgtgaatt 1860
gtaccgaggt gcctgtggcc atccacgccg atcagctgac ccccaacatgg cgggtgtaca 1920
gcaccggctc caacgtgttc cagacaagag caggatgtct gatcggagca gagcacgtga 1980
acaattccta tgagtgcgac atcccaatcg gcgccggcat ctgtgcctct taccagaccc 2040
agacaaactc tccaaggaga gcacggagcg tggcatccca gtctatcatc gcctatacca 2100
tgtccctggg cgccgagaat tctgtggcct actctaacaa tagcatcgcc atcccaacca 2160
acttcacaat ctctgtgacc acagagatcc tgcccgtgtc catgaccaag acatctgtgg 2220
actgcacaat gtatatctgt ggcgattcta ccgagtgcag caacctgctg ctgcagtacg 2280
gcagcttttg tacccagctg aatagagccc tgacaggcat cgccgtggag caggataaga 2340
acacacagga ggtgttcgcc caggtgaagc aaatctacaa gaccccccct atcaaggact 2400
ttggcggctt caatttttcc cagatcctgc ctgatccatc caagccttct aagcggagct 2460
ttatcgagga cctgctgttc aacaaggtga ccctggccga tgccggcttc atcaagcagt 2520
atggcgattg cctgggcgac atcgcagcac gggacctgat ctgtgcccag aagtttaatg 2580
gcctgaccgt gctgccaccc ctgctgacag atgagatgat cgcacagtac acaagcgccc 2640
tgctggcagg aaccatcaca tccggatgga ccttcggcgc aggagccgcc ctgcagatcc 2700
cctttgccat gcagatggcc tataggttca acggcatcgg cgtgacccag aatgtgctgt 2760
acgagaacca gaagctgatc gccaatcagt ttaactccgc catcggcaag atccaggaca 2820
gcctgtcctc tacagcctcc gccctgggca agctgcagga tgtggtgaat cagaacgccc 2880
aggccctgaa taccctggtg aagcagctga gctccaactt cggcgccatc tctagcgtgc 2940
tgaatgatat cctgagccgg ctggacaagg tggaggcaga ggtgcagatc gaccggctga 3000
tcacaggcag actgcagtct ctgcagacct atgtgacaca gcagctgatc agggcagcag 3060
agatcagggc aagcgccaat ctggcagcaa ccaagatgtc cgagtgcgtg ctgggccagt 3120
ctaagagagt ggacttttgt ggcaagggct atcacctgat gtccttccct cagtctgccc 3180
cacacggcgt ggtgtttctg cacgtgacct acgtgcccgc ccaggagaag aacttcacca 3240
cagcccctgc catctgccac gatggcaagg cccactttcc aagggagggc gtgttcgtgt 3300
ccaacggcac ccactggttt gtgacacagc gcaatttcta cgagccccag atcatcacca 3360
cagacaatac cttcgtgagc ggcaactgtg acgtggtcat cggcatcgtg aacaataccg 3420
tgtatgatcc actgcagccc gagctggaca gctttaagga ggagctggat aagtacttca 3480
agaatcacac ctcccctgac gtggatctgg gcgacatcag cggcatcaat gcctccgtgg 3540
tgaacatcca gaaggagatc gaccgcctga acgaggtggc caagaatctg aacgagagcc 3600
tgatcgatct gcaggagctg ggcaagtatg agcagtacat caagtggcca tggtacatct 3660
ggctgggctt catcgccggc ctgatcgcca tcgtgatggt gaccatcatg ctgtgctgta 3720
tgacatcctg ctgttcttgc ctgaagggct gctgtagctg cggctcctgt tgtaagtttg 3780
atgaagacga ttccgagcct gtcctgaagg gcgtgaagct gcactatacc tctagataat 3840

-continued

```
gag                                                                3843


<210> SEQ ID NO 6
<211> LENGTH: 750
<212> TYPE: DNA
<213> ORGANISM: Artificial Sequence
<220> FEATURE:
<223> OTHER INFORMATION: nucleotide sequence encoding TPA fused to
      SARS-CoV-2 RBD

<400> SEQUENCE: 6

atggatgcaa tgaagagagg gctctgctgt gtgctgctgc tgtgtggagc agtcttcgtt     60

tcgcccagct taattaagag ggtgcagcca accgagtcta tcgtgcgctt tcctaatatc    120

acaaacctgt gcccatttgg cgaggtgttc aacgcaacca ggttcgcaag cgtgtacgca    180

tggaatagga agcgcatctc taactgcgtg gccgactata gcgtgctgta caactccgcc    240

tctttcagca cctttaagtg ctatggcgtg tcccccacaa agctgaatga cctgtgcttt    300

accaacgtgt acgccgattc tttcgtgatc aggggcgacg aggtgcgcca gatcgcacct    360

ggacagacag gcaagatcgc cgactacaat tataagctgc cagacgattt caccggctgc    420

gtgatcgcct ggaacagcaa caatctggat tccaaagtgg gcggcaacta caattatctg    480

taccggctgt ttagaaagag caatctgaag cccttcgaga gggacatctc tacagaaatc    540

taccaggccg gcagcacccc ttgcaatggc gtggagggct ttaactgtta tttcccactg    600

cagtcctacg gcttccagcc cacaaacggc gtgggctatc agccttaccg cgtggtggtg    660

ctgagctttg agctgctgca cgcaccagca acagtgtgcg gacccaagaa gtccaccaat    720

ctggtgaaga acaagtgcgt gaacttctaa                                     750


<210> SEQ ID NO 7
<211> LENGTH: 223
<212> TYPE: PRT
<213> ORGANISM: Artificial Sequence
<220> FEATURE:
<223> OTHER INFORMATION: amino acid sequence of SARS-CoV-2 RBD

<400> SEQUENCE: 7

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160
```

-continued

```
Pro Cys Asn Gly Val Glu Gly Phe Asn Cys Tyr Phe Pro Leu Gln Ser
            165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe
    210                 215                 220


<210> SEQ ID NO 8
<211> LENGTH: 526
<212> TYPE: PRT
<213> ORGANISM: Artificial Sequence
<220> FEATURE:
<223> OTHER INFORMATION: amino acid sequence of SARS-CoV-2 NTD and RBD

<400> SEQUENCE: 8

Val Asn Leu Thr Thr Arg Thr Gln Leu Pro Pro Ala Tyr Thr Asn Ser
1               5                   10                  15

Phe Thr Arg Gly Val Tyr Tyr Pro Asp Lys Val Phe Arg Ser Ser Val
            20                  25                  30

Leu His Ser Thr Gln Asp Leu Phe Leu Pro Phe Phe Ser Asn Val Thr
        35                  40                  45

Trp Phe His Ala Ile His Val Ser Gly Thr Asn Gly Thr Lys Arg Phe
    50                  55                  60

Asp Asn Pro Val Leu Pro Phe Asn Asp Gly Val Tyr Phe Ala Ser Thr
65                  70                  75                  80

Glu Lys Ser Asn Ile Ile Arg Gly Trp Ile Phe Gly Thr Thr Leu Asp
                85                  90                  95

Ser Lys Thr Gln Ser Leu Leu Ile Val Asn Asn Ala Thr Asn Val Val
            100                 105                 110

Ile Lys Val Cys Glu Phe Gln Phe Cys Asn Asp Pro Phe Leu Gly Val
        115                 120                 125

Tyr Tyr His Lys Asn Asn Lys Ser Trp Met Glu Ser Glu Phe Arg Val
    130                 135                 140

Tyr Ser Ser Ala Asn Asn Cys Thr Phe Glu Tyr Val Ser Gln Pro Phe
145                 150                 155                 160

Leu Met Asp Leu Glu Gly Lys Gln Gly Asn Phe Lys Asn Leu Arg Glu
                165                 170                 175

Phe Val Phe Lys Asn Ile Asp Gly Tyr Phe Lys Ile Tyr Ser Lys His
            180                 185                 190

Thr Pro Ile Asn Leu Val Arg Asp Leu Pro Gln Gly Phe Ser Ala Leu
        195                 200                 205

Glu Pro Leu Val Asp Leu Pro Ile Gly Ile Asn Ile Thr Arg Phe Gln
    210                 215                 220

Thr Leu Leu Ala Leu His Arg Ser Tyr Leu Thr Pro Gly Asp Ser Ser
225                 230                 235                 240

Ser Gly Trp Thr Ala Gly Ala Ala Ala Tyr Tyr Val Gly Tyr Leu Gln
                245                 250                 255

Pro Arg Thr Phe Leu Leu Lys Tyr Asn Glu Asn Gly Thr Ile Thr Asp
            260                 265                 270

Ala Val Asp Cys Ala Leu Asp Pro Leu Ser Glu Thr Lys Cys Thr Leu
        275                 280                 285

Lys Ser Phe Thr Val Glu Lys Gly Ile Tyr Gln Thr Ser Asn Phe Arg
    290                 295                 300
```

-continued

```
Val Gln Pro Thr Glu Ser Ile Val Arg Phe Pro Asn Ile Thr Asn Leu
305                 310                 315                 320

Cys Pro Phe Gly Glu Val Phe Asn Ala Thr Arg Phe Ala Ser Val Tyr
                325                 330                 335

Ala Trp Asn Arg Lys Arg Ile Ser Asn Cys Val Ala Asp Tyr Ser Val
            340                 345                 350

Leu Tyr Asn Ser Ala Ser Phe Ser Thr Phe Lys Cys Tyr Gly Val Ser
        355                 360                 365

Pro Thr Lys Leu Asn Asp Leu Cys Phe Thr Asn Val Tyr Ala Asp Ser
    370                 375                 380

Phe Val Ile Arg Gly Asp Glu Val Arg Gln Ile Ala Pro Gly Gln Thr
385                 390                 395                 400

Gly Lys Ile Ala Asp Tyr Asn Tyr Lys Leu Pro Asp Asp Phe Thr Gly
                405                 410                 415

Cys Val Ile Ala Trp Asn Ser Asn Asn Leu Asp Ser Lys Val Gly Gly
            420                 425                 430

Asn Tyr Asn Tyr Leu Tyr Arg Leu Phe Arg Lys Ser Asn Leu Lys Pro
        435                 440                 445

Phe Glu Arg Asp Ile Ser Thr Glu Ile Tyr Gln Ala Gly Ser Thr Pro
    450                 455                 460

Cys Asn Gly Val Glu Gly Phe Asn Cys Tyr Phe Pro Leu Gln Ser Tyr
465                 470                 475                 480

Gly Phe Gln Pro Thr Asn Gly Val Gly Tyr Gln Pro Tyr Arg Val Val
                485                 490                 495

Val Leu Ser Phe Glu Leu Leu His Ala Pro Ala Thr Val Cys Gly Pro
            500                 505                 510

Lys Lys Ser Thr Asn Leu Val Lys Asn Lys Cys Val Asn Phe
        515                 520                 525


<210> SEQ ID NO 9
<211> LENGTH: 666
<212> TYPE: PRT
<213> ORGANISM: Artificial Sequence
<220> FEATURE:
<223> OTHER INFORMATION: amino acid sequence of SARS-CoV-2 NTD, RBD,
      CTD2 and CTD3

<400> SEQUENCE: 9

Val Asn Leu Thr Thr Arg Thr Gln Leu Pro Pro Ala Tyr Thr Asn Ser
1               5                   10                  15

Phe Thr Arg Gly Val Tyr Tyr Pro Asp Lys Val Phe Arg Ser Ser Val
            20                  25                  30

Leu His Ser Thr Gln Asp Leu Phe Leu Pro Phe Phe Ser Asn Val Thr
        35                  40                  45

Trp Phe His Ala Ile His Val Ser Gly Thr Asn Gly Thr Lys Arg Phe
    50                  55                  60

Asp Asn Pro Val Leu Pro Phe Asn Asp Gly Val Tyr Phe Ala Ser Thr
65                  70                  75                  80

Glu Lys Ser Asn Ile Ile Arg Gly Trp Ile Phe Gly Thr Thr Leu Asp
                85                  90                  95

Ser Lys Thr Gln Ser Leu Leu Ile Val Asn Asn Ala Thr Asn Val Val
            100                 105                 110

Ile Lys Val Cys Glu Phe Gln Phe Cys Asn Asp Pro Phe Leu Gly Val
        115                 120                 125

Tyr Tyr His Lys Asn Asn Lys Ser Trp Met Glu Ser Glu Phe Arg Val
    130                 135                 140
```

```
Tyr Ser Ser Ala Asn Asn Cys Thr Phe Glu Tyr Val Ser Gln Pro Phe
145                 150                 155                 160

Leu Met Asp Leu Glu Gly Lys Gln Gly Asn Phe Lys Asn Leu Arg Glu
                165                 170                 175

Phe Val Phe Lys Asn Ile Asp Gly Tyr Phe Lys Ile Tyr Ser Lys His
            180                 185                 190

Thr Pro Ile Asn Leu Val Arg Asp Leu Pro Gln Gly Phe Ser Ala Leu
        195                 200                 205

Glu Pro Leu Val Asp Leu Pro Ile Gly Ile Asn Ile Thr Arg Phe Gln
    210                 215                 220

Thr Leu Leu Ala Leu His Arg Ser Tyr Leu Thr Pro Gly Asp Ser Ser
225                 230                 235                 240

Ser Gly Trp Thr Ala Gly Ala Ala Ala Tyr Tyr Val Gly Tyr Leu Gln
                245                 250                 255

Pro Arg Thr Phe Leu Leu Lys Tyr Asn Glu Asn Gly Thr Ile Thr Asp
            260                 265                 270

Ala Val Asp Cys Ala Leu Asp Pro Leu Ser Glu Thr Lys Cys Thr Leu
        275                 280                 285

Lys Ser Phe Thr Val Glu Lys Gly Ile Tyr Gln Thr Ser Asn Phe Arg
    290                 295                 300

Val Gln Pro Thr Glu Ser Ile Val Arg Phe Pro Asn Ile Thr Asn Leu
305                 310                 315                 320

Cys Pro Phe Gly Glu Val Phe Asn Ala Thr Arg Phe Ala Ser Val Tyr
                325                 330                 335

Ala Trp Asn Arg Lys Arg Ile Ser Asn Cys Val Ala Asp Tyr Ser Val
            340                 345                 350

Leu Tyr Asn Ser Ala Ser Phe Ser Thr Phe Lys Cys Tyr Gly Val Ser
        355                 360                 365

Pro Thr Lys Leu Asn Asp Leu Cys Phe Thr Asn Val Tyr Ala Asp Ser
    370                 375                 380

Phe Val Ile Arg Gly Asp Glu Val Arg Gln Ile Ala Pro Gly Gln Thr
385                 390                 395                 400

Gly Lys Ile Ala Asp Tyr Asn Tyr Lys Leu Pro Asp Asp Phe Thr Gly
                405                 410                 415

Cys Val Ile Ala Trp Asn Ser Asn Asn Leu Asp Ser Lys Val Gly Gly
            420                 425                 430

Asn Tyr Asn Tyr Leu Tyr Arg Leu Phe Arg Lys Ser Asn Leu Lys Pro
        435                 440                 445

Phe Glu Arg Asp Ile Ser Thr Glu Ile Tyr Gln Ala Gly Ser Thr Pro
    450                 455                 460

Cys Asn Gly Val Glu Gly Phe Asn Cys Tyr Phe Pro Leu Gln Ser Tyr
465                 470                 475                 480

Gly Phe Gln Pro Thr Asn Gly Val Gly Tyr Gln Pro Tyr Arg Val Val
                485                 490                 495

Val Leu Ser Phe Glu Leu Leu His Ala Pro Ala Thr Val Cys Gly Pro
            500                 505                 510

Lys Lys Ser Thr Asn Leu Val Lys Asn Lys Cys Val Asn Phe Asn Phe
        515                 520                 525

Asn Gly Leu Thr Gly Thr Gly Val Leu Thr Glu Ser Asn Lys Lys Phe
    530                 535                 540

Leu Pro Phe Gln Gln Phe Gly Arg Asp Ile Ala Asp Thr Thr Asp Ala
545                 550                 555                 560
```

```
Val Arg Asp Pro Gln Thr Leu Glu Ile Leu Asp Ile Thr Pro Cys Ser
            565                 570                 575

Phe Gly Gly Val Ser Val Ile Thr Pro Gly Thr Asn Thr Ser Asn Gln
            580                 585                 590

Val Ala Val Leu Tyr Gln Asp Val Asn Cys Thr Glu Val Pro Val Ala
        595                 600                 605

Ile His Ala Asp Gln Leu Thr Pro Thr Trp Arg Val Tyr Ser Thr Gly
    610                 615                 620

Ser Asn Val Phe Gln Thr Arg Ala Gly Cys Leu Ile Gly Ala Glu His
625                 630                 635                 640

Val Asn Asn Ser Tyr Glu Cys Asp Ile Pro Ile Gly Ala Gly Ile Cys
                645                 650                 655

Ala Ser Tyr Gln Thr Gln Thr Asn Ser Pro
            660                 665


<210> SEQ ID NO 10
<211> LENGTH: 471
<212> TYPE: PRT
<213> ORGANISM: Artificial Sequence
<220> FEATURE:
<223> OTHER INFORMATION: amino acid sequence of IgK, SARS-CoV-2 RBD and
      Fc

<400> SEQUENCE: 10

Met Glu Thr Asp Thr Leu Leu Leu Trp Val Leu Leu Leu Trp Val Pro
1               5                   10                  15

Gly Ser Thr Gly Arg Val Gln Pro Thr Glu Ser Ile Val Arg Phe Pro
            20                  25                  30

Asn Ile Thr Asn Leu Cys Pro Phe Gly Glu Val Phe Asn Ala Thr Arg
        35                  40                  45

Phe Ala Ser Val Tyr Ala Trp Asn Arg Lys Arg Ile Ser Asn Cys Val
    50                  55                  60

Ala Asp Tyr Ser Val Leu Tyr Asn Ser Ala Ser Phe Ser Thr Phe Lys
65                  70                  75                  80

Cys Tyr Gly Val Ser Pro Thr Lys Leu Asn Asp Leu Cys Phe Thr Asn
                85                  90                  95

Val Tyr Ala Asp Ser Phe Val Ile Arg Gly Asp Glu Val Arg Gln Ile
            100                 105                 110

Ala Pro Gly Gln Thr Gly Lys Ile Ala Asp Tyr Asn Tyr Lys Leu Pro
        115                 120                 125

Asp Asp Phe Thr Gly Cys Val Ile Ala Trp Asn Ser Asn Asn Leu Asp
    130                 135                 140

Ser Lys Val Gly Gly Asn Tyr Asn Tyr Leu Tyr Arg Leu Phe Arg Lys
145                 150                 155                 160

Ser Asn Leu Lys Pro Phe Glu Arg Asp Ile Ser Thr Glu Ile Tyr Gln
                165                 170                 175

Ala Gly Ser Thr Pro Cys Asn Gly Val Glu Gly Phe Asn Cys Tyr Phe
            180                 185                 190

Pro Leu Gln Ser Tyr Gly Phe Gln Pro Thr Asn Gly Val Gly Tyr Gln
        195                 200                 205

Pro Tyr Arg Val Val Val Leu Ser Phe Glu Leu Leu His Ala Pro Ala
    210                 215                 220

Thr Val Cys Gly Pro Lys Lys Ser Thr Asn Leu Val Lys Asn Lys Cys
225                 230                 235                 240

Val Asn Phe Val Asp Lys Thr His Thr Cys Pro Pro Cys Pro Ala Pro
                245                 250                 255
```

```
Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470


<210> SEQ ID NO 11
<211> LENGTH: 1275
<212> TYPE: PRT
<213> ORGANISM: Artificial Sequence
<220> FEATURE:
<223> OTHER INFORMATION: amino acid sequence of SARS-CoV-2 Spike protein

<400> SEQUENCE: 11

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140
```

-continued

```
Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560
```

```
Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
```

```
        980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Lys Leu  His Tyr Thr Ser Arg
    1265                 1270                 1275


<210> SEQ ID NO 12
<211> LENGTH: 675
<212> TYPE: PRT
<213> ORGANISM: Artificial Sequence
<220> FEATURE:
<223> OTHER INFORMATION: nucleotide sequence encoding  SARS-CoV-2 RBD

<400> SEQUENCE: 12

Ala Thr Gly Ala Gly Gly Gly Thr Gly Cys Ala Gly Cys Cys Ala Ala
1               5                   10                  15

Cys Cys Gly Ala Gly Thr Cys Thr Ala Thr Cys Gly Thr Gly Cys Gly
            20                  25                  30

Cys Thr Thr Thr Cys Cys Thr Ala Ala Thr Ala Thr Cys Ala Cys Ala
        35                  40                  45

Ala Ala Cys Cys Thr Gly Thr Gly Cys Cys Cys Ala Thr Thr Thr Gly
```

-continued

```
    50                  55                  60

Gly Cys Gly Ala Gly Gly Thr Gly Thr Thr Cys Ala Ala Cys Gly Cys
65                  70                  75                  80

Ala Ala Cys Cys Ala Gly Gly Thr Thr Cys Gly Cys Ala Ala Gly Cys
                85                  90                  95

Gly Thr Gly Thr Ala Cys Gly Cys Ala Thr Gly Gly Ala Ala Thr Ala
            100                 105                 110

Gly Gly Ala Ala Gly Cys Gly Cys Ala Thr Cys Thr Cys Thr Ala Ala
        115                 120                 125

Cys Thr Gly Cys Gly Thr Gly Gly Cys Cys Gly Ala Cys Thr Ala Thr
    130                 135                 140

Ala Gly Cys Gly Thr Gly Cys Thr Gly Thr Ala Cys Ala Ala Cys Thr
145                 150                 155                 160

Cys Cys Gly Cys Cys Thr Cys Thr Thr Thr Cys Ala Gly Cys Ala Cys
                165                 170                 175

Cys Thr Thr Thr Ala Ala Gly Thr Gly Cys Thr Ala Thr Gly Gly Cys
            180                 185                 190

Gly Thr Gly Thr Cys Cys Cys Cys Cys Ala Cys Ala Ala Ala Gly Cys
        195                 200                 205

Thr Gly Ala Ala Thr Gly Ala Cys Cys Thr Gly Thr Gly Cys Thr Thr
    210                 215                 220

Thr Ala Cys Cys Ala Ala Cys Gly Thr Gly Thr Ala Cys Gly Cys Cys
225                 230                 235                 240

Gly Ala Thr Thr Cys Thr Thr Thr Cys Gly Thr Gly Ala Thr Cys Ala
                245                 250                 255

Gly Gly Gly Gly Cys Gly Ala Cys Gly Ala Gly Gly Thr Gly Cys Gly
            260                 265                 270

Cys Cys Ala Gly Ala Thr Cys Gly Cys Ala Cys Cys Thr Gly Gly Ala
        275                 280                 285

Cys Ala Gly Ala Cys Ala Gly Gly Cys Ala Ala Gly Ala Thr Cys Gly
    290                 295                 300

Cys Cys Gly Ala Cys Thr Ala Cys Ala Ala Thr Thr Ala Thr Ala Ala
305                 310                 315                 320

Gly Cys Thr Gly Cys Cys Ala Gly Ala Cys Gly Ala Thr Thr Thr Cys
                325                 330                 335

Ala Cys Cys Gly Gly Cys Thr Gly Cys Gly Thr Gly Ala Thr Cys Gly
            340                 345                 350

Cys Cys Thr Gly Gly Ala Ala Cys Ala Gly Cys Ala Ala Cys Ala Ala
        355                 360                 365

Thr Cys Thr Gly Gly Ala Thr Thr Cys Cys Ala Ala Ala Gly Thr Gly
    370                 375                 380

Gly Gly Cys Gly Gly Cys Ala Ala Cys Thr Ala Cys Ala Ala Thr Thr
385                 390                 395                 400

Ala Thr Cys Thr Gly Thr Ala Cys Cys Gly Gly Cys Thr Gly Thr Thr
                405                 410                 415

Thr Ala Gly Ala Ala Ala Gly Ala Gly Cys Ala Ala Thr Cys Thr Gly
            420                 425                 430

Ala Ala Gly Cys Cys Cys Thr Thr Cys Gly Ala Gly Ala Gly Gly Gly
        435                 440                 445

Ala Cys Ala Thr Cys Thr Cys Thr Ala Cys Ala Gly Ala Ala Ala Thr
    450                 455                 460

Cys Thr Ala Cys Cys Ala Gly Gly Cys Cys Gly Gly Cys Ala Gly Cys
465                 470                 475                 480
```

Ala Cys Cys Cys Cys Thr Thr Gly Cys Ala Ala Thr Gly Gly Cys Gly
485 490 495

Thr Gly Gly Ala Gly Gly Gly Cys Thr Thr Thr Ala Ala Cys Thr Gly
500 505 510

Thr Thr Ala Thr Thr Thr Cys Cys Cys Ala Cys Thr Gly Cys Ala Gly
515 520 525

Thr Cys Cys Thr Ala Cys Gly Gly Cys Thr Thr Cys Cys Ala Gly Cys
530 535 540

Cys Cys Ala Cys Ala Ala Ala Cys Gly Gly Cys Gly Thr Gly Gly Gly
545 550 555 560

Cys Thr Ala Thr Cys Ala Gly Cys Cys Thr Thr Ala Cys Cys Gly Cys
565 570 575

Gly Thr Gly Gly Thr Gly Gly Thr Gly Cys Thr Gly Ala Gly Cys Thr
580 585 590

Thr Thr Gly Ala Gly Cys Thr Gly Cys Thr Gly Cys Ala Cys Gly Cys
595 600 605

Ala Cys Cys Ala Gly Cys Ala Ala Cys Ala Gly Thr Gly Thr Gly Cys
610 615 620

Gly Gly Ala Cys Cys Cys Ala Ala Gly Ala Ala Gly Thr Cys Cys Ala
625 630 635 640

Cys Cys Ala Ala Thr Cys Thr Gly Gly Thr Gly Ala Ala Gly Ala Ala
645 650 655

Cys Ala Ala Gly Thr Gly Cys Gly Thr Gly Ala Ala Cys Thr Thr Cys
660 665 670

Thr Ala Ala
675

<210> SEQ ID NO 13
<211> LENGTH: 224
<212> TYPE: PRT
<213> ORGANISM: Artificial Sequence
<220> FEATURE:
<223> OTHER INFORMATION: amino acid sequence of SARS-CoV-2 RBD

<400> SEQUENCE: 13

Met Arg Val Gln Pro Thr Glu Ser Ile Val Arg Phe Pro Asn Ile Thr
1 5 10 15

Asn Leu Cys Pro Phe Gly Glu Val Phe Asn Ala Thr Arg Phe Ala Ser
20 25 30

Val Tyr Ala Trp Asn Arg Lys Arg Ile Ser Asn Cys Val Ala Asp Tyr
35 40 45

Ser Val Leu Tyr Asn Ser Ala Ser Phe Ser Thr Phe Lys Cys Tyr Gly
50 55 60

Val Ser Pro Thr Lys Leu Asn Asp Leu Cys Phe Thr Asn Val Tyr Ala
65 70 75 80

Asp Ser Phe Val Ile Arg Gly Asp Glu Val Arg Gln Ile Ala Pro Gly
85 90 95

Gln Thr Gly Lys Ile Ala Asp Tyr Asn Tyr Lys Leu Pro Asp Asp Phe
100 105 110

Thr Gly Cys Val Ile Ala Trp Asn Ser Asn Asn Leu Asp Ser Lys Val
115 120 125

Gly Gly Asn Tyr Asn Tyr Leu Tyr Arg Leu Phe Arg Lys Ser Asn Leu
130 135 140

Lys Pro Phe Glu Arg Asp Ile Ser Thr Glu Ile Tyr Gln Ala Gly Ser
145 150 155 160

```
Thr Pro Cys Asn Gly Val Glu Gly Phe Asn Cys Tyr Phe Pro Leu Gln
                165                 170                 175

Ser Tyr Gly Phe Gln Pro Thr Asn Gly Val Gly Tyr Gln Pro Tyr Arg
            180                 185                 190

Val Val Val Leu Ser Phe Glu Leu Leu His Ala Pro Ala Thr Val Cys
        195                 200                 205

Gly Pro Lys Lys Ser Thr Asn Leu Val Lys Asn Lys Cys Val Asn Phe
    210                 215                 220


<210> SEQ ID NO 14
<211> LENGTH: 669
<212> TYPE: DNA
<213> ORGANISM: Artificial Sequence
<220> FEATURE:
<223> OTHER INFORMATION: nucleotide sequence encoding SARS-CoV-2 English
      variant RBD

<400> SEQUENCE: 14

agggtgcagc caaccgagtc tatcgtgcgc tttcctaata tcacaaacct gtgcccattt      60

ggcgaggtgt tcaacgcaac caggttcgca agcgtgtacg catggaatag gaagcgcatc     120

tctaactgcg tggccgacta tagcgtgctg tacaactccg cctctttcag cacctttaag     180

tgctatggcg tgtcccccac aaagctgaat gacctgtgct ttaccaacgt gtacgccgat     240

tctttcgtga tcaggggcga cgaggtgcgc cagatcgcac ctggacagac aggcaagatc     300

gccgactaca attataagct gccagacgat ttcaccggct gcgtgatcgc ctggaacagc     360

aacaatctgg attccaaagt gggcggcaac tacaattatc tgtaccggct gtttagaaag     420

agcaatctga agcccttcga gagggacatc tctacagaaa tctaccaggc cggcagcacc     480

ccttgcaatg gcgtggaggg ctttaactgt tatttcccac tgcagtccta cggcttccag     540

cccacatacg gcgtgggcta tcagccttac cgcgtggtgg tgctgagctt tgagctgctg     600

cacgcaccag caacagtgtg cggacccaag aagtccacca atctggtgaa gaacaagtgc     660

gtgaacttc                                                             669


<210> SEQ ID NO 15
<211> LENGTH: 669
<212> TYPE: DNA
<213> ORGANISM: Artificial Sequence
<220> FEATURE:
<223> OTHER INFORMATION: nucleotide sequence encoding SARS-CoV-2 South
      African variant RBD

<400> SEQUENCE: 15

agggtgcagc caaccgagtc tatcgtgcgc tttcctaata tcacaaacct gtgcccattt      60

ggcgaggtgt tcaacgcaac caggttcgca agcgtgtacg catggaatag gaagcgcatc     120

tctaactgcg tggccgacta tagcgtgctg tacaactccg cctctttcag cacctttaag     180

tgctatggcg tgtcccccac aaagctgaat gacctgtgct ttaccaacgt gtacgccgat     240

tctttcgtga tcaggggcga cgaggtgcgc cagatcgcac ctggacagac aggcaatatc     300

gccgactaca attataagct gccagacgat ttcaccggct gcgtgatcgc ctggaacagc     360

aacaatctgg attccaaagt gggcggcaac tacaattatc tgtaccggct gtttagaaag     420

agcaatctga agcccttcga gagggacatc tctacagaaa tctaccaggc cggcagcacc     480

ccttgcaatg gcgtgaaggg ctttaactgt tatttcccac tgcagtccta cggcttccag     540

cccacatacg gcgtgggcta tcagccttac cgcgtggtgg tgctgagctt tgagctgctg     600
```

cacgcaccag caacagtgtg cggacccaag aagtccacca atctggtgaa gaacaagtgc 660
gtgaacttc 669

<210> SEQ ID NO 16
<211> LENGTH: 69
<212> TYPE: DNA
<213> ORGANISM: Artificial Sequence
<220> FEATURE:
<223> OTHER INFORMATION: nucleotide sequence encoding TPA

<400> SEQUENCE: 16
atggatgcaa tgaagagagg gctctgctgt gtgctgctgc tgtgtggagc agtcttcgtt 60
tcgcccagc 69

<210> SEQ ID NO 17
<211> LENGTH: 23
<212> TYPE: PRT
<213> ORGANISM: Artificial Sequence
<220> FEATURE:
<223> OTHER INFORMATION: amino acid sequence of TPA

<400> SEQUENCE: 17

Met Asp Ala Met Lys Arg Gly Leu Cys Cys Val Leu Leu Leu Cys Gly
1 5 10 15

Ala Val Phe Val Ser Pro Ser
20

<210> SEQ ID NO 18
<211> LENGTH: 1255
<212> TYPE: PRT
<213> ORGANISM: SARS-CoV-1

<400> SEQUENCE: 18

Met Phe Ile Phe Leu Leu Phe Leu Thr Leu Thr Ser Gly Ser Asp Leu
1 5 10 15

Asp Arg Cys Thr Thr Phe Asp Asp Val Gln Ala Pro Asn Tyr Thr Gln
20 25 30

His Thr Ser Ser Met Arg Gly Val Tyr Tyr Pro Asp Glu Ile Phe Arg
35 40 45

Ser Asp Thr Leu Tyr Leu Thr Gln Asp Leu Phe Leu Pro Phe Tyr Ser
50 55 60

Asn Val Thr Gly Phe His Thr Ile Asn His Thr Phe Gly Asn Pro Val
65 70 75 80

Ile Pro Phe Lys Asp Gly Ile Tyr Phe Ala Ala Thr Glu Lys Ser Asn
85 90 95

Val Val Arg Gly Trp Val Phe Gly Ser Thr Met Asn Asn Lys Ser Gln
100 105 110

Ser Val Ile Ile Ile Asn Asn Ser Thr Asn Val Val Ile Arg Ala Cys
115 120 125

Asn Phe Glu Leu Cys Asp Asn Pro Phe Phe Ala Val Ser Lys Pro Met
130 135 140

Gly Thr Gln Thr His Thr Met Ile Phe Asp Asn Ala Phe Asn Cys Thr
145 150 155 160

Phe Glu Tyr Ile Ser Asp Ala Phe Ser Leu Asp Val Ser Glu Lys Ser
165 170 175

Gly Asn Phe Lys His Leu Arg Glu Phe Val Phe Lys Asn Lys Asp Gly
180 185 190

Phe Leu Tyr Val Tyr Lys Gly Tyr Gln Pro Ile Asp Val Val Arg Asp

-continued

```
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
    450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
    530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
        595                 600                 605

Ala Ile His Ala Asp Gln Leu Thr Pro Ala Trp Arg Ile Tyr Ser Thr
    610                 615                 620
```

-continued

```
Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
        675                 680                 685

Tyr Ser Asn Asn Thr Ile Ala Ile Pro Thr Asn Phe Ser Ile Ser Ile
    690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
        755                 760                 765

Gln Met Tyr Lys Thr Pro Thr Leu Lys Tyr Phe Gly Gly Phe Asn Phe
    770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
        835                 840                 845

Asp Asp Met Ile Ala Ala Tyr Thr Ala Ala Leu Val Ser Gly Thr Ala
    850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
        915                 920                 925

Lys Leu Gln Asp Val Val Asn Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile  Arg Ala Ser Ala Asn  Leu Ala Ala
        995                 1000                1005

Thr Lys  Met Ser Glu Cys Val  Leu Gly Gln Ser Lys  Arg Val Asp
    1010                1015                1020

Phe Cys  Gly Lys Gly Tyr His  Leu Met Ser Phe Pro  Gln Ala Ala
    1025                1030                1035
```

-continued

```
Pro His  Gly Val Val Phe Leu  His Val Thr Tyr Val  Pro Ser Gln
    1040                 1045                 1050

Glu Arg  Asn Phe Thr Thr Ala  Pro Ala Ile Cys His  Glu Gly Lys
    1055                 1060                 1065

Ala Tyr  Phe Pro Arg Glu Gly  Val Phe Val Phe Asn  Gly Thr Ser
    1070                 1075                 1080

Trp Phe  Ile Thr Gln Arg Asn  Phe Phe Ser Pro Gln  Ile Ile Thr
    1085                 1090                 1095

Thr Asp  Asn Thr Phe Val Ser  Gly Asn Cys Asp Val  Val Ile Gly
    1100                 1105                 1110

Ile Ile  Asn Asn Thr Val Tyr  Asp Pro Leu Gln Pro  Glu Leu Asp
    1115                 1120                 1125

Ser Phe  Lys Glu Glu Leu Asp  Lys Tyr Phe Lys Asn  His Thr Ser
    1130                 1135                 1140

Pro Asp  Val Asp Leu Gly Asp  Ile Ser Gly Ile Asn  Ala Ser Val
    1145                 1150                 1155

Val Asn  Ile Gln Lys Glu Ile  Asp Arg Leu Asn Glu  Val Ala Lys
    1160                 1165                 1170

Asn Leu  Asn Glu Ser Leu Ile  Asp Leu Gln Glu Leu  Gly Lys Tyr
    1175                 1180                 1185

Glu Gln  Tyr Ile Lys Trp Pro  Trp Tyr Val Trp Leu  Gly Phe Ile
    1190                 1195                 1200

Ala Gly  Leu Ile Ala Ile Val  Met Val Thr Ile Leu  Leu Cys Cys
    1205                 1210                 1215

Met Thr  Ser Cys Cys Ser Cys  Leu Lys Gly Ala Cys  Ser Cys Gly
    1220                 1225                 1230

Ser Cys  Cys Lys Phe Asp Glu  Asp Asp Ser Glu Pro  Val Leu Lys
    1235                 1240                 1245

Gly Val  Lys Leu His Tyr Thr
    1250                 1255


<210> SEQ ID NO 19
<211> LENGTH: 1273
<212> TYPE: PRT
<213> ORGANISM: SARS-CoV-2

<400> SEQUENCE: 19

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140
```

```
Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560
```

-continued

```
Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
```

-continued

```
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Lys Leu  His Tyr Thr
    1265                 1270


<210> SEQ ID NO 20
<211> LENGTH: 825
<212> TYPE: PRT
<213> ORGANISM: SARS-CoV-2

<400> SEQUENCE: 20

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60
```

-continued

```
Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
```

```
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys
            820                 825


<210> SEQ ID NO 21
<211> LENGTH: 669
<212> TYPE: DNA
<213> ORGANISM: Artificial Sequence
<220> FEATURE:
<223> OTHER INFORMATION: nucleotide sequence encoding SARS-CoV-2
      Brazilian variant RBD

<400> SEQUENCE: 21

agggtgcagc caaccgagtc tatcgtgcgc tttcctaata tcacaaacct gtgcccattt      60

ggcgaggtgt tcaacgcaac caggttcgca agcgtgtacg catggaatag gaagcgcatc     120
```

-continued

```
tctaactgcg tggccgacta tagcgtgctg tacaactccg cctctttcag cacctttaag    180

tgctatggcg tgtcccccac aaagctgaat gacctgtgct ttaccaacgt gtacgccgat    240

tctttcgtga tcaggggcga cgaggtgcgc cagatcgcac ctggacagac aggcacaatc    300

gccgactaca attataagct gccagacgat ttcaccggct gcgtgatcgc ctggaacagc    360

aacaatctgg attccaaagt gggcggcaac tacaattatc tgtaccggct gtttagaaag    420

agcaatctga agcccttcga gagggacatc tctacagaaa tctaccaggc cggcagcacc    480

ccttgcaatg gcgtgaaggg ctttaactgt tatttcccac tgcagtccta cggcttccag    540

cccacatacg gcgtgggcta tcagccttac cgcgtggtgg tgctgagctt tgagctgctg    600

cacgcaccag caacagtgtg cggacccaag aagtccacca atctggtgaa gaacaagtgc    660

gtgaacttc                                                            669
```

```
<210> SEQ ID NO 22
<211> LENGTH: 223
<212> TYPE: PRT
<213> ORGANISM: Artificial Sequence
<220> FEATURE:
<223> OTHER INFORMATION: amino acid sequence of SARS-CoV-2 English
      variant RBD

<400> SEQUENCE: 22

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
            85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
            165                 170                 175

Tyr Gly Phe Gln Pro Thr Tyr Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe
    210                 215                 220


<210> SEQ ID NO 23
<211> LENGTH: 223
<212> TYPE: PRT
<213> ORGANISM: Artificial Sequence
```

<220> FEATURE:
<223> OTHER INFORMATION: amino acid sequence of SARS-CoV-2 South African variant RBD

<400> SEQUENCE: 23

```
Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Asn Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Lys Gly Phe Asn Cys Tyr Phe Pro Leu Gln Ser
                165                 170                 175

Tyr Gly Phe Gln Pro Thr Tyr Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe
    210                 215                 220
```

<210> SEQ ID NO 24
<211> LENGTH: 223
<212> TYPE: PRT
<213> ORGANISM: Artificial Sequence
<220> FEATURE:
<223> OTHER INFORMATION: amino acid sequence of SARS-CoV-2 Brazilian variant RBD

<400> SEQUENCE: 24

```
Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Thr Ile Ala Asp Tyr Asn Tyr Lys Leu Pro Asp Asp Phe Thr
            100                 105                 110
```

```
Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Lys Gly Phe Asn Cys Tyr Phe Pro Leu Gln Ser
                165                 170                 175

Tyr Gly Phe Gln Pro Thr Tyr Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe
    210                 215                 220


<210> SEQ ID NO 25
<211> LENGTH: 750
<212> TYPE: DNA
<213> ORGANISM: Artificial Sequence
<220> FEATURE:
<223> OTHER INFORMATION: nucleotide sequence encoding TPA fused to
      SARS-CoV-2 English variant RBD

<400> SEQUENCE: 25

atggatgcaa tgaagagagg gctctgctgt gtgctgctgc tgtgtggagc agtcttcgtt      60

tcgcccagct taattaagag ggtgcagcca accgagtcta tcgtgcgctt tcctaatatc     120

acaaacctgt gcccatttgg cgaggtgttc aacgcaacca ggttcgcaag cgtgtacgca     180

tggaatagga agcgcatctc taactgcgtg gccgactata gcgtgctgta caactccgcc     240

tctttcagca cctttaagtg ctatggcgtg tcccccacaa agctgaatga cctgtgcttt     300

accaacgtgt acgccgattc tttcgtgatc aggggcgacg aggtgcgcca gatcgcacct     360

ggacagacag gcaagatcgc cgactacaat tataagctgc cagacgattt caccggctgc     420

gtgatcgcct ggaacagcaa caatctggat tccaaagtgg gcggcaacta caattatctg     480

taccggctgt ttagaaagag caatctgaag cccttcgaga gggacatctc tacagaaatc     540

taccaggccg gcagcacccc ttgcaatggc gtggagggct ttaactgtta tttcccactg     600

cagtcctacg gcttccagcc cacatacggc gtgggctatc agccttaccg cgtggtggtg     660

ctgagctttg agctgctgca cgcaccagca acagtgtgcg gacccaagaa gtccaccaat     720

ctggtgaaga acaagtgcgt gaacttctaa                                      750


<210> SEQ ID NO 26
<211> LENGTH: 750
<212> TYPE: DNA
<213> ORGANISM: Artificial Sequence
<220> FEATURE:
<223> OTHER INFORMATION: nucleotide sequence encoding TPA fused to
      SARS-CoV-2 South African variant RBD

<400> SEQUENCE: 26

atggatgcaa tgaagagagg gctctgctgt gtgctgctgc tgtgtggagc agtcttcgtt      60

tcgcccagct taattaagag ggtgcagcca accgagtcta tcgtgcgctt tcctaatatc     120

acaaacctgt gcccatttgg cgaggtgttc aacgcaacca ggttcgcaag cgtgtacgca     180

tggaatagga agcgcatctc taactgcgtg gccgactata gcgtgctgta caactccgcc     240

tctttcagca cctttaagtg ctatggcgtg tcccccacaa agctgaatga cctgtgcttt     300
```

accaacgtgt acgccgattc tttcgtgatc aggggcgacg aggtgcgcca gatcgcacct 360
ggacagacag gcaatatcgc cgactacaat tataagctgc cagacgattt caccggctgc 420
gtgatcgcct ggaacagcaa caatctggat tccaaagtgg gcggcaacta caattatctg 480
taccggctgt ttagaaagag caatctgaag cccttcgaga gggacatctc tacagaaatc 540
taccaggccg gcagcacccc ttgcaatggc gtgaagggct ttaactgtta tttcccactg 600
cagtcctacg gcttccagcc cacatacggc gtgggctatc agccttaccg cgtggtggtg 660
ctgagctttg agctgctgca cgcaccagca acagtgtgcg gacccaagaa gtccaccaat 720
ctggtgaaga acaagtgcgt gaacttctaa 750

<210> SEQ ID NO 27
<211> LENGTH: 750
<212> TYPE: DNA
<213> ORGANISM: Artificial Sequence
<220> FEATURE:
<223> OTHER INFORMATION: nucleotide sequence encoding TPA fused to SARS-CoV-2 Brazilian variant RBD

<400> SEQUENCE: 27
atggatgcaa tgaagagagg gctctgctgt gtgctgctgc tgtgtggagc agtcttcgtt 60
tcgcccagct taattaagag ggtgcagcca accgagtcta tcgtgcgctt tcctaatatc 120
acaaacctgt gcccatttgg cgaggtgttc aacgcaacca ggttcgcaag cgtgtacgca 180
tggaatagga agcgcatctc taactgcgtg gccgactata gcgtgctgta caactccgcc 240
tctttcagca cctttaagtg ctatggcgtg tcccccacaa agctgaatga cctgtgcttt 300
accaacgtgt acgccgattc tttcgtgatc aggggcgacg aggtgcgcca gatcgcacct 360
ggacagacag gcacaatcgc cgactacaat tataagctgc cagacgattt caccggctgc 420
gtgatcgcct ggaacagcaa caatctggat tccaaagtgg gcggcaacta caattatctg 480
taccggctgt ttagaaagag caatctgaag cccttcgaga gggacatctc tacagaaatc 540
taccaggccg gcagcacccc ttgcaatggc gtgaagggct ttaactgtta tttcccactg 600
cagtcctacg gcttccagcc cacatacggc gtgggctatc agccttaccg cgtggtggtg 660
ctgagctttg agctgctgca cgcaccagca acagtgtgcg gacccaagaa gtccaccaat 720
ctggtgaaga acaagtgcgt gaacttctaa 750

<210> SEQ ID NO 28
<211> LENGTH: 669
<212> TYPE: DNA
<213> ORGANISM: SARS-CoV-2

<400> SEQUENCE: 28
agagtccaac caacagaatc tattgttaga tttcctaata ttacaaactt gtgccctttt 60
ggtgaagttt ttaacgccac cagatttgca tctgtttatg cttggaacag gaagagaatc 120
agcaactgtg ttgctgatta ttctgtccta tataattccg catcattttc cacttttaag 180
tgttatggag tgtctcctac taaattaaat gatctctgct ttactaatgt ctatgcagat 240
tcatttgtaa ttagaggtga tgaagtcaga caaatcgctc cagggcaaac tggaaagatt 300
gctgattata attataaatt accagatgat tttacaggct gcgttatagc ttggaattct 360
aacaatcttg attctaaggt tggtggtaat tataattacc tgtatagatt gtttaggaag 420
tctaatctca aaccttttga gagagatatt tcaactgaaa tctatcaggc cggtagcaca 480
ccttgtaatg gtgttgaagg ttttaattgt tactttcctt tacaatcata tggtttccaa 540

-continued

```
cccactaatg gtgttggtta ccaaccatac agagtagtag tactttcttt tgaacttcta    600

catgcaccag caactgtttg tggacctaaa aagtctacta atttggttaa aaacaaatgt    660

gtcaatttc                                                            669
```